(12) United States Patent
Gray et al.

(10) Patent No.: US 8,993,251 B2
(45) Date of Patent: *Mar. 31, 2015

(54) GENES FROM 20Q13 AMPLICON AND THEIR USES

(75) Inventors: Joe W. Gray, San Francisco, CA (US); Colin Conrad Collins, San Rafael, CA (US); Soo-In Hwang, Berkeley, CA (US); Tony Godfrey, San Francisco, CA (US); David Kowbel, San Francisco, CA (US); Johanna Rommens, Toronto (CA)

(73) Assignees: The Regents of the University of California, Oakland, CA (US); The Hospital for Sick Children, Toronto (CA)

( * ) Notice: Subject to any disclaimer, the term of this patent is extended or adjusted under 35 U.S.C. 154(b) by 0 days.

This patent is subject to a terminal disclaimer.

(21) Appl. No.: 13/328,999

(22) Filed: Dec. 16, 2011

(65) Prior Publication Data

US 2013/0095475 A1    Apr. 18, 2013

Related U.S. Application Data

(63) Continuation of application No. 12/127,774, filed on May 27, 2008, now Pat. No. 8,101,370, which is a continuation of application No. 08/785,532, filed on Jan. 17, 1997, now Pat. No. 7,455,964, which is a continuation-in-part of application No. 08/731,499, filed on Oct. 16, 1996, now Pat. No. 7,049,424, and a continuation-in-part of application No. 08/680,395, filed on Jul. 15, 1996, now Pat. No. 5,892,010.

(51) Int. Cl.
| | |
|---|---|
| *G01N 33/574* | (2006.01) |
| *C12Q 1/68* | (2006.01) |
| *C07K 14/47* | (2006.01) |
| *C07K 14/82* | (2006.01) |
| *C12N 9/12* | (2006.01) |
| *C12N 9/90* | (2006.01) |
| *G01N 33/68* | (2006.01) |

(52) U.S. Cl.
CPC .............. *C12Q 1/6886* (2013.01); *C07K 14/47* (2013.01); *C07K 14/4705* (2013.01); *C07K 14/82* (2013.01); *C12N 9/1205* (2013.01); *C12N 9/90* (2013.01); *G01N 33/6893* (2013.01); *C12Q 2600/112* (2013.01); *C12Q 2600/118* (2013.01)
USPC ...................................................... 435/7.23

(58) Field of Classification Search
None
See application file for complete search history.

(56) References Cited

U.S. PATENT DOCUMENTS

| | | | |
|---|---|---|---|
| 5,472,842 | A | 12/1995 | Stokke et al. |
| 5,633,365 | A | 5/1997 | Stokke et al. |
| 5,801,021 | A | 9/1998 | Gray et al. |
| 5,892,010 | A | 4/1999 | Gray et al. |
| 6,268,184 | B1 | 7/2001 | Gray et al. |
| 6,808,878 | B1 | 10/2004 | Gray et al. |
| 7,049,424 | B2 | 5/2006 | Gray et al. |
| 7,413,899 | B2 | 8/2008 | Gray et al. |
| 7,455,964 | B1 | 11/2008 | Gray et al. |
| 7,811,986 | B2 | 10/2010 | Gray et al. |
| 8,021,837 | B2 | 9/2011 | Pinkel et al. |
| 8,101,370 | B2 | 1/2012 | Gray et al. |
| 2006/0257895 | A1 | 11/2006 | Pinkel et al. |
| 2006/0292591 | A1 | 12/2006 | Gray et al. |
| 2009/0081672 | A1 | 3/2009 | Gray et al. |

FOREIGN PATENT DOCUMENTS

| | | |
|---|---|---|
| AU | 774736 | 10/2004 |
| CA | 2257821 | 7/1997 |
| EP | 0 430402 | 5/1991 |
| EP | 0 492214 | 7/1992 |
| EP | 0 533 006 | 3/1993 |
| EP | 0 571 911 | 12/1993 |
| EP | 960197 | 12/1999 |
| JP | H05-506998 | 10/1993 |
| JP | H07-289297 | 11/1995 |
| JP | H08-092285 | 4/1996 |
| WO | WO 90/05789 | 5/1990 |
| WO | WO 93/18186 | 9/1993 |
| WO | WO 93/24514 | 12/1993 |
| WO | WO 93/25671 | 12/1993 |
| WO | WO 94/01548 | 12/1994 |
| WO | WO 95/14772 | 1/1995 |
| WO | WO 95/09929 | 4/1995 |
| WO | WO 95/33480 | 12/1995 |
| WO | WO 97/14811 | 4/1997 |
| WO | WO 98/02539 | 1/1998 |
| WO | WO 03/027263 | 4/2003 |

OTHER PUBLICATIONS

Tockman et al, Cancer Research vol. 52 p. 2711s (1992).*
Janicke et al Fibrinolysis vol. 4 p. 69 (1990).*
Accession No. H16954 Jun. 29, 1995.
Accession No. G11697 Oct. 19, 1995.
Accession No. G25553 May 31, 1996.
Accession No. G27410 Jun. 28, 1996.
Accession No. H12950 Jun. 27, 1995.
Accession No. H16953 Jun. 29, 1995.
Accession No. N32481 Jan. 10, 1996.
Accession No. H40682 Aug. 16, 1995.
Accession No. N70546 Mar. 14, 1996.
Accession No. N93893 Apr. 5, 1996.
Accession No. Q63862 (Jan. 29, 1995).
Database EST-STS on MPsrch Accession No. G08049, Murray et al., *Cooperative human linkage center*, Aug. 8, 1995.

(Continued)

*Primary Examiner* — Sheela J Huff
(74) *Attorney, Agent, or Firm* — Weaver Austin Villeneuve & Sampson LLP

(57) ABSTRACT

The present invention relates to cDNA sequences from a region of amplification on chromosome 20 associated with disease. The sequences can be used in hybridization methods for the identification of chromosomal abnormalities associated with various diseases. The sequences can also be used for treatment of diseases.

9 Claims, 3 Drawing Sheets

(56) References Cited

OTHER PUBLICATIONS

Genbank Accession No. N78571 (Mar. 29, 1996) Hillier et al.
Genbank Accession No. X17105 (Nov. 9, 1995) Bergsman et al.
ATCC/NIH Repository Catalogue, 1992, p. 113-114.
Beeler et al. (1994) "Prokaryotic Expression Cloning of a Novel Human Tyrosine Kinase," *Molecular and Cellular Biology*, 14: 982-988.
Benz et al., Journal of the National Cancer Institute, Nov. 1989, 81(22):1704-1709.
Bergerheim et al., "Deletion Mapping of Chromosomes 8, 10, and 16 in Human Prostatic Carcinoma," *Genes. Chromosomes & Cancer*, vol. 3, pp. 215-220 (1991).
Berns et al., Gene, 1995, 159:11-18.
Blennow et al. "Complete characterization of a large marker chromosome by reverse and forward chromosome painting" Human Genetics (1992) vol. 90, pp. 371-374 Received: Jun. 15, 1992/Revised: Jul. 6, 1992.
Borg et al., Oncogene, 1991, 6:137-143.
Brinkmann et al., Genome Research, 1996, 6:187-194.
Brown et aL, 1995, *J. BioL Chem.* 279(49):29236-29243.
Brown et aL, 1995, *Protein Expr. Purif.* 6(1):63-71.
Burmer, GC et al, 1991, *Environmental Health perspectives*, 93: 27-31.
Buskens, C et al, *Digesteive Disease Week Abstracts and Itinerary Planner*, 2003, abstract No. 850.
Chromosome 12 map (from www.ncbi.nlm.gov, downloaded Dec. 4, 2008).
Collins, PNAS 95: 8703-8708 (1998).
Courjal et al., British Journal of Cancer, 1996, 74:1984-1989.
Cremer et al., *Hum. Genet.*, v. 80 1988, 235-246.
Deng et al., Breast Cancer Res Treat, 1996;40(3):271-81.
Dutrillaux et al., Cancer Genet Cytogenet, 1990, 49:203-207.
Einhorn, S. et al., Leukemia, vol. 3, pp. 871-874 (1989).
Ferrari, DM et al., 1996, Accession No. X94910 Genebank.
Fu et al., EMBO J. Aug. 15, 1996;15(16):4392-4401.
Glinsjy et al. (2004) J. Clin. Invest, 113: 913-923.
Gorbulev et al., "Organization and chromosomal localization of the gene for the human bombesin receptor subtype expressed in pregnant uterus." FEBS Letters, 340:260-264 (1994).
Guan et al., Advances in Brief, Aug. 1996, 56:3446-3450.
Guan et al: "Identification of cryptic sites of DNA sequence amplifications in human breast cancer by chromosome mi crodissection." Nature Genetics, Oct. 1994, 8(2):155-161.
Gyapay et al., "The 1993-1994 genethon human genetic linkage map." *Nature Genetics*, Jun. 1994, vol. 7, pp. 246-329.
Horowitz, et al., "The Human Glucocerebrosidase Gene and Pseudogene: Structure and Evolution", *Genomics* 4:87-96 (1989).
Jang et al., *Clin Exp Metastasis*, Sep. 1997:15(5):469-83.
Jonson, T. et al., Genes, Chromosomes & Cancer, vol. 29, pp. 192-199 (2000).
Joos et al., "Detection of amplidfied DNA sequences by reverse chromosome painting using genomic tumor DNA as probe" Human Genet (1193) vol. 90, pp. 584-589.
Kallioniemi et al. "Comparative Genomic Hybridization for Molecular Cytogenetic Analysis of Solid Tumors" Science vol. 258, Oct. 30, 1992 pp. 818-821.
Kallioniemi et al. "ERBB2 amplification in breast cancer analyzed by fluorescence in situ hybridization" Proc. Acad. Nat. Sci, 89:5321-5325 (1992).
Kallioniemi et al., "Detection and Mapping of Amplified Dna . . . " *Proc Natl Acad Sci USA*, Mar. 15, 1994;91(6):2156-60.
Lathe (1985) *J. Mol. Biol.* 183:1-12.
Le, F. et al., *Journal of Affective Disorders* 32(3): 187-195 (1994).
Lichter et al., "High Resolution Mapping of Human Chromosome 11 by in Situ Hybridization with Cosmid Clones," *Science*, vol. 247: 64-69 (1990).
Lichter et al., Delineation of individual human chromosomes in metaphase and interphase cells . . . , *Hum Genet* (1988) 80:224-234.
Lidsky, A.S. et al., PNAS USA, vol. 82, pp. 6221-6225 (1985).
Lin., L. et al., Cancer Res., vol. 60, pp. 1341-1347 (2000).

Lindbolm et al., "Deletions on Chromosome 16 in Primary Familial Breast Carcinomas Are Associated with Development of Distant Metatases," *Cancer Research*, vol. 53, pp. 3707-3711, Aug. 15, 1993.
Lucas et al., "Translocations between two specific human chromosomes detected by three-color chromosome painting," *Cytogenet Cell Genet*, vol. 62 pp. 11-12 (1993).
Matthews et al., *Anal. Biochem.*, v. 169, Feb. 1988, 1-25.
Meltzer, P.S. et al., Cell Growth Diff., vol. 2, pp. 495-501 (Oct. 1991).
Montesano et al, 1996, *Intl J Cancer*, 69(3): 225-235.
Morris et al., "Entire ABL Gene is Joined with 5"-BCF in Some Patients With Philadelphia-Positive Leukemia", *Blood*, 78(4): 1078-1084 (1991).
Muleris et al., Genes Chromosomes Cancer, Jul. 1994; 10(3):160-70.
New England Biolabs. Catalog 152-153 (1993-1994).
Oesterreich et al. (1996) Clin Cancer Res, 2: 1199-1206.
Okubo et al., "An Expression Profile of Actiave Genes in Human Colonic Mucosa", *DNA Research* 1:37-45 (1994).
Pawlak et al., "Characterization of a Large Population of mRNAs from Human Testis," *Genomics* 26:151-158 (1995).
Pinkel et al., "Flourescence in situ hybridization with human chromosome-specific libraries. Detection of trisomy 21 and translocation of chromosome 4," *Proc. Acad. Nat. Sci.*, 1988, 85:9138-9142.
Powell et al., *Pharmacogenetics* Oct. 1998:8(5):411-21.
Promega (Provincia Catalog) p. 167; 1994-1995.
Reznikoff et al., Genes & Development, Sep. 1994, 8(18):2227-2240.
Robinson, NJ et al. 1994. Accession No. Z47159 GenBank.
Schable, K. et al. 1993. Accession No. X76070 Genebank.
Shepherd et al: "Preparation and screening of an arrayed human genomic library generated with the P1 cloning system" *Proc National Academy of Science*, Mar. 1994, 91: 2629-2633.
Short et al., "λ ZAP: a bacteriophage λ expression Vector with in vivo excision properties," *Nucleic Acids Research* (1988) 16 (15): 7583-7600.
Smith et al., *Breast Cancer Research and Treatment*, May 1991, 18(1):s51-s54.
Stokke et al. "A Physical Map of Chromosome 20 Established Using Fluorescence in Situ Hybridization and Digital Image Analysis," *Genomics* 26:134-137 (1995).
Tanner et al. (1995) "Amplification of Chromosomal Region 20q13 in Invasive Breast Cancer: Prognostic Implication," *Clinical Cancer Research*, 1:1455-1461.
Tanner et al., "Increased Copy Number on 20q13 in Breast Cancer: Defining the Critical Region and Exclusion of Candidates Genes," *Cancer Research*. Aug. 15, 1994, vol. 54, pp. 4257-4260.
Tanner et al., "Independent amplification and frequest co-amplificatin of three nonsystenic regions on the long arm of chromosome 20 in human breast cancer," *Cancer Research* 56: 3441-3445 (1996).
Tockman et al. (1992) Cancer Res. 52:2711s-2718s.
The American Society of Human Genetics, Supp. No. 3, 1993 *Amer Jrnl of Genet*, 2 pages.
Trent, J. et al., PNAS USA, vol. 83, pp. 470-473 (1986).
Vallejo et al., *Biochimie*, Dec. 2000:82(12):1129-33.
Vandesompele et al. (2003) Oncogene 22(3): 456-60.
Van de Vijver et al., Biochimica et Biophysica Acta, 1991, 1072:33-50.
Wang, A.M. et al., PNAS USA, vol. 86, pp. 9717-9721 (1989).
Wiegant et al., *Nucleic Acids Res.*, 19(12):3237-3241 (1991).
Zakut-Houri, et al., A single gene and a pseudogene for cellular tumour antigen p53, *Nature*, 306:594-597 (1983).
Genbank Accession No. W05407 (Apr. 23, 1996) Hillier et al.
US Notice of Allowance dated Apr. 29, 2010 issued in U.S. Appl. No. 12/177,608.
Hasel et al. (1990) "Nucleotide Sequence of cDNA coding for mouse cyclophilin." Nucleic Acids Research, vol. 18, No. 13, p. 4019.
Sambrook et al. (1989) "Molecular Cloning" *2nd Ed, Cold Spring Harbor*, pp. 9.47-9.62.
Stokke et al. (Sep. 1993) "Genetic characterization of 20q Amplication in human breat cancer," *Abstract sumitted to the 43rd Annual Meeting of the American Society of Human Genectics* (Appendix 2).

* cited by examiner

SEQUENCE LISTING (1) GENERAL INFORMATION:

(iii) NUMBER OF SEQUENCES: 55

(2) INFORMATION FOR SEQ ID NO:1:

(i) SEQUENCE CHARACTERISTICS:
      (A) LENGTH: 3000 base pairs
      (B) TYPE: nucleic acid

```
         (C) STRANDEDNESS: single
         (D) TOPOLOGY: linear (ii) MOLECULE TYPE: cDNA (ix) FEATURE:
         (A) NAME/KEY: -
         (B) LOCATION: 1..3000
         (D) OTHER INFORMATION: /note= "cDNA clone 3bf4 of 3kb
             transcript of tyrosine kinase gene A6"

(xi) SEQUENCE DESCRIPTION: SEQ ID NO:1:

CCGCCGGCCG GGGCGCCTGG CTGCACTCAG CGCCGGAGCC GGGAGCTAGC GGCCGCCGCC      60

ATGTCCCACC AGACCGGCAT CCAAGCAAGT GAAGATGTTA AAGAGATCTT TGCCAGAGCC     120

AGAAATGGAA AGTACAGACT TCTGAAAATA TCTATTGAAA ATGAGCAACT TGTGATTGGA     180

TCATATAGTC AGCCTTCAGA TTCCTGGGAT AAGGATTATG ATTCCTTTGT TTTACCCCTG     240

TTGGAGGACA AACAACCATG CTATATATTA TTCAGGTTAG ATTCTCAGAA TGCCCAGGGA     300

TATGAATGGA TATTCATTGC ATGGTCTCCA GATCATTCTC ATGTTCGTCA AAAAATGTTG     360

TATGCAGCAA CAAGAGCAAC TCTGAAGAAG GAATTTGGAG GTGGCCACAT TAAAGATGAA     420

GTATTTGGAA CAGTAAAGGA AGATGTATCA TTACATGGAT ATAAAAAATA CTTGCTGTCA     480

CAATCTTCCC CTGCCCCACT GACTGCAGCT GAGGAAGAAC TACGACAGAT TAAAATCAAT     540

GAGGTACAGA CTGACGTGGG TGTGGACACT AAGCATCAAA CACTACAAGG AGTAGCATTT     600

CCCATTTCTC GAGAAGCCTT TCAGGCTTTG GAAAAATTGA ATAATAGACA GCTCAACTAT     660

GTGCAGTTGG AAATAGATAT AAAAAATGAA ATTATAATTT TGGCCAACAC AACAAATACA     720

GAACTGAAAG ATTTGCCAAA GAGGATTCCC AAGGATTCAG CTCGTTACCA TTTCTTTCTG     780

TATAAACATT CCCATGAAGG AGACTATTTA GAGTCCATAG TTTTTATTTA TTCAATGCCT     840

GGATACACAT GCAGTATAAG AGAGCGGATG CTGTATTCTA GCTGCAAGAG CCGTCTGCTA     900

GAAATTGTAG AAAGACAACT ACAAATGGAT GTAATTAGAA AGATCGAGAT AGACAATGGG     960

GATGAGTTGA CTGCAGACTT CCTTTATGAA GAAGTACATC CCAAGCAGCA TGCACACAAG    1020

CAAAGTTTTG CAAAACCAAA AGGTCCTGCA GGAAAAAGAG GAATTCGAAG ACTAATTAGG    1080

GGCCCAGCGG AAACTGAAGC TACTACTGAT TAAAGTCATC ACATTAAACA TTGTAATACT    1140

AGTTTTTTAA AAGTCCAGCT TTTAGTACAG GAGAACTGAA ATCATTCCAT GTTGATATAA    1200

AGTAGGGAAA AAAATTGTAC TTTTTGGAAA ATAGCACTTT TCACTTCTGT GTGTTTTTAA    1260

AATTAATGTT ATAGAAGACT CATGATTTCT ATTTTTGAGT TAAAGCTAGA AAAGGGTTCA    1320

ACATAATGTT TAATTTTGTC ACACTGTTTT CATAGCGTTG ATTCCACACT TCAAATACTT    1380

CTTAAAATTT TATACAGTTG GGCCAGTTCT AGAAAGTCTG ATGTCTCAAA GGGTAAACTT    1440

ACTACTTTCT TGTGGGACAG AAAGACCTTA AATATTCAT ATTACTTAAT GAATATGTTA    1500

AGGACCAGGC TAGAGTATTT TCTAAGCTGG AAACTTAGTG TGCCTTGGAA AAGCCGCAAG    1560

TTGCTTACTC CGAGTAGCTG TGCTAGCTCT GTCAGACTGT AGGATCATGT CTGCAACTTT    1620

TAGAAATAGT GCTTTATATT GCAGCAGTCT TTTATATTTG ACTTTTTTTT AATAGCATTA    1680

AAATTGCAGA TCAGCTCACT CTGAAACTTT AAGGGTACCA GATATTTCT ATACTGCAGG    1740

ATTTCTGATG ACATTGAAAG ACTTTAAACA GCCTTAGTAA ATTATCTTTC TAATGCTCTG    1800

TGAGGCCAAA CATTTATGTT CAGATTGAAA TTTAAATTAA TATCATTCAA AAGGAAACAA    1860

AAAATGTTGA GTTTTAAAAA TCAGGATTGA CTTTTTTCTC CAAAACCATA CATTTATGGG    1920

CAAATTGTGT TCTTTATCAC TTCCGAGCAA ATACTCAGAT TTAAAATTAC TTTAAAGTCC    1980
```

-continued

```
TGGTACTTAA CAGGCTAACG TAGATAAACA CCTTAATAAT CTCAGTTAAT ACTGTATTTC    2040

AAAACACATT TAACTGTTTT CTAATGCTTT GCATTATCAG TTACAACCTA GAGAGATTTT    2100

GAGCCTCATA TTTCTTTGAT ACTTGAAATA GAGGGAGCTA AACACTTAA TGTTTAATCT     2160

GTTAAACCTG CTGCAAGAGC CATAACTTTG AGGCATTTTC TAAATGAACT GTGGGGATCC    2220

AGGATTTGTA ATTTCTTGAT CTAAACTTTA TGCTGCATAA ATCACTTATC GGAAATGCAC    2280

ATTTCATAGT GTGAAGCACT CATTTCTAAA CCTTATTATC TAAGGTAATA TATGCACCTT    2340

TCAGAAATTT GTGTTCGAGT AAGTAAAGCA TATTAGAATA ATTGTGGGTT GACAGATTTT    2400

TAAAATAGAA TTTAGAGTAT TTGGGGTTTT GTTTGTTTAC AAATAATCAG ACTATAATAT    2460

TTAAACATGC AAAATAACTG ACAATAATGT TGCACTTGTT TACTAAAGAT ATAAGTTGTT    2520

CCATGGGTGT ACACGTAGAC AGACACACAT ACACCCAAAT TATTGCATTA AGAATCCTGG    2580

AGCAGACCAT AGCTGAAGCT GTTATTTTCA GTCAGGAAGA CTACCTGTCA TGAAGGTATA    2640

AAATAATTTA GAAGTGAATG TTTTTCTGTA CCATCTATGT GCAATTATAC TCTAAATTCC    2700

ACTACACTAC ATTAAAGTAA ATGGACATTC CAGAATATAG ATGTGATTAT AGTCTTAAAC    2760

TAATTATTAT TAAACCAATG ATTGCTGAAA ATCAGTGATG CATTTGTTAT AGAGTATAAC    2820

TCATCGTTTA CAGTATGTTT TAGTTGGCAG TATCATACCT AGATGGTGAA TAACATATTC    2880

CCAGTAAATT TATATAGCAG TGAAGAATTA CATGCCTTCT GGTGGACATT TTATAAGTGC    2940

ATTTTATATC ACAATAAAAA TTTTTTCTCT TTAAAAAAAA AAAACAAGAA AAAAAAAAA     3000
```

(2) INFORMATION FOR SEQ ID NO:2:

(i) SEQUENCE CHARACTERISTICS:
        (A) LENGTH: 723 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: -
        (B) LOCATION: 1..723
        (D) OTHER INFORMATION: /note= "cDNA clone 1b11 of 3.5kb
           transcript"

(xi) SEQUENCE DESCRIPTION: SEQ ID NO:2:

```
TGGAAGCTGT CATGGTTACC GTCTCTAACG TTGGACTCTT AAGAAAATGA TTATTCCTGG      60

TTTCTAGACA GGCCAAATGT AATTCACCTA CGTGGCAGAT TAAAGAGGTG GGCTTACTAG     120

ATTTGATTGG GTATTGAGCA TGCTCTGAAT GACAGTCCCC AAAAAGGACC TCTTATCCGT    180

TCTTCCCCTT GGGGAAGGGC TTTTGCCACT TCCATGTCAA TGTGGCAGTT GAGCTTGGAA    240

ATTGGTGCGT TGTACAACAT AAGCATTACT CTCCAAGAT GTGCCTGTGT AGAAATGGTC     300

ATAGATTCAA AACTGTAGCT ACTATGTGGA CAGGGGGGCA GCAAGGACCC CACTTTGTAA    360

AACATGTTTT GGGGGAATGT TTTGTTTTTC ATTTTCTTAT TACCTGGCAA ATAATCCAG     420

GTGGTGTGTG AGTCACCAGT AGAGATTATA AAGTCCAAGG AAGTAGAATC AGCCTTACAA    480

ACAGTGGACC TCAACGAAGG AGATGCTGCA CCTGAACCCA CWGAAGCGAA ACTCAAAAGA    540

GAAGAAAGCA AACCAAGAAC CTCTCTGATG RCGTTTCTCA GACAAATGGT AAGCCCCTTA    600

CTTCCAGTAT AGGAAACCTA AGATACCTAG AGCGGCTTTT GGGAACAATG GGCTCATGCC    660

ACAGGTAGTA GGAGACATAA TTGTAGCTGG TGTGTATGGA ATGTGAATGG AATATGGATT    720

GCG                                                                   723
```

(2) INFORMATION FOR SEQ ID NO:3:

(i) SEQUENCE CHARACTERISTICS:
        (A) LENGTH: 1507 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: -
        (B) LOCATION: 1..1507
        (D) OTHER INFORMATION: /note= "cDNA clone cc49 of 6-7kb
            transcript with homology to C2H2 zinc
            finger genes"

(xi) SEQUENCE DESCRIPTION: SEQ ID NO:3:

```
GCAGGTTGCT GGGATTGACT TCTTGCTCAA TTGAAACACT CATTCAATGG AGACAAAGAG     60

CACTAATGCT TTGTGCTGAT TCATATTTGA ATCGAGGCAT TGGGAACCCT GTATGCCTTG    120

TTTGTGGAAA GAACCAGTGA CACCATCACT GAGCTTCCTA AAAGTTCGAA GAAGTTAGAG    180

GACTATACAC TTTCTTTTGA ACTTTTATAA TAAATATTTG CTCTGGTTTT GGAACCCAGG    240

ACTGTTAGAG GGTGAGTGAC AGGTCTTACA GTGGCCTTAA TCCAACTCCA GAAATTGCCC    300

AACGGAACTT TGAGATTATA TGCAATCGAA AGTGACAGGA ACATGCCAA CTCAATCCCT     360

CTTAATGTAC ATGGATGGCC AAGAGTGATT GGCAGCTCTC TTGCCAGTCC GATGGAGATG    420

GAGATGCCTT GTCAATGAAA GGGCCCNCTG TTGTCAATTC CGAGCTACAC AAAGAAAAAA    480

ATGTCAATCC GAATCGAGGG GAATATGCCC TTGGATTGCA TGTTCTGCAG CCAGACCTTC    540

ACACATTCAG AAGACCTTAA TAAACATGTC TTAATGCAAC ACCGGCCTAC CCTCTGTGAA    600

CCAGCAGTTC TTCGGGTTGA AGCAGAGTAT CTCAGTCCGC TTGATAAAAG TCAAGTGCGA    660

ACAGAACCTC CCAAGGAAAA GAATTGCAAG GAAAATGAAT TTAGCTGTGA GGTATGTGGG    720

CAGACATTTA GAGTCGCTTT TGATGTTGAG ATCCACATGA GAACACACAA AGATTCTTTC    780

ACTTACGGGT GTAACATGTG CGGAAGAAGA TTCAAGGAGC CTTGGTTTCT TAAAAATCAC    840

ATGCGGACRC ATAATGGCAA ATCGGGGGCC AGAAGCAAAC TGCAGCAAGG CTTGGAGAGT    900

AGTCCAGCAA CGATCAACGA GGTCGTCCAG GTGCACGCGG CCGAGAGCAT CTCCTCTCCT    960

TGCAAAATCT GCATGGTTTG TGGCTTCCTA TTTCCAAATA AAGAAAGTCT AATTGAGCAC   1020

CGCAAGGTGC ACACCAAAAA AACTGCTTTC GGTACCAGCA GCGCGCAGAC AGACTCTCCA   1080

CAAGGAGGAA TGCCGTCCTC GAGGGAGGAC TTCCTGCAGT TGTTCAACTT GAGACCAAAA   1140

TCTCACCCTG AAACGGGGAA GAAGCCTGTC AGATGCATCC CTCAGCTCGA TCCGTTCACC   1200

ACCTTCCAGG CTTGGCAKCT GGCTACCAAA GGAAWAGTTG CCATTTGCCA AGAAGTGAAG   1260

GAATTGGGGC AAGAAGGGAG CACCGACAAC GACGATTCGA GTTCCGAGAA GGAGCTTGGA   1320

GAAACAAATA GAACCATTG TGCAGGCCTC TCGCAAGAGA AAGAGAAGTG CAAACACTCC    1380

CACGGCGAAG CGCCCTCCGT GGACGCGGAT CCCAAGTTAC CCAGTAGCAA GGAGAAGCCC   1440

ACTCACTGCT CCGAGTGCGG CAAAGCTTTC AGAACCTACC ACCAGCTGGT CTTGCACTCC   1500

AGGGTCC                                                            1507
```

(2) INFORMATION FOR SEQ ID NO:4:

(i) SEQUENCE CHARACTERISTICS:
        (A) LENGTH: 2605 base pairs
        (B) TYPE: nucleic acid
        (C) STRANDEDNESS: single

```
            (D) TOPOLOGY: linear (ii) MOLECULE TYPE: cDNA (ix) FEATURE:
            (A) NAME/KEY: -
            (B) LOCATION: 1..2605
            (D) OTHER INFORMATION: /note= "cDNA clone cc43 of 4 kb
                transcript"

(xi) SEQUENCE DESCRIPTION: SEQ ID NO:4:

CAAGCTCGAA ATTAACCCTC ACTAAAGGGA ACAAAAGCTG GAGCTCCACC GCGGTGGCGG      60

CCGCTCTAGA ACTAGTGGAT CCCCCGGGCT GCAGGAATTC GGCACGAGCT GGCTACTAC      120

GATGGCGATG AGTTTCGAGT GGCCGTGGCA GTATCGCTTC CCACCCTTCT TTACGTTACA     180

ACCGAATGTG GACACTCGGC AGAAGCAGCT GGCCGCCTGG TGCTCGCTGG TCCTGTCCTT     240

CTGCCGCCTG CACAAACAGT CCAGCATGAC GGTGATGGAA GCTCAGGAGA GCCCGCTCTT     300

CAACAACGTC AAGCTACAGC GAAAGCTTCC TGTGGAGTCG ATCCAGATTG TATTAGAGGA     360

ACTGAGGAAG AAAGGGAACC TCGAGTGGTT GGATAAGAGC AAGTCCAGCT TCCTGATCAT     420

GTGGCGGAGG CCAGAAGAAT GGGGGAAACT CATCTATCAG TGGGTTTCCA GGAGTGGCCA     480

GAACAACTCC GTCTTTACCC TGTATGAACT GACTAATGGG GAAGACACAG AGGATGAGGA     540

GTTCCACGGG CTGGATGAAG CCACTCTACT GCGGGCTCTG CAGGCCCTAC AGCAGGAGCA     600

CAAGGCCGAG ATCATCACTG TCAGCGATGG CCGAGGCGTC AAGTTCTTCT AGCAGGGACC     660

TGTCTCCCTT TACTTCTTAC CTCCCACCTT TCCAGGGCTT TCAAAAGGAG ACAGACCCAG     720

TGTCCCCCAA AGACTGGATC TGTGACTCCA CCAGACTCAA AAGGACTCCA GTCCTGAAGG     780

CTGGGACCTG GGGATGGGTT TCTCACACCC CATATGTCTG TCCCTTGGAT AGGGTGAGGC     840

TGAAGCACCA GGGAGAAAAT ATGTGCTTCT TCTCGCCCTA CCTCCTTTCC CATCCTAGAC     900

TGTCCTTGAG CCAGGGTCTG TAAACCTGAC ACTTTATATG TGTTCACACA TGTAAGTACA     960

TACACACATG CGCCTGCAGC ACATGCTTCT GTCTCCTCCT CCTCCCACCC CTTTAGCTGC    1020

TGTTGCCTCC CTTCTCAGGC TGGTGCTGGA TCCTTCCTAG GGGATGGGGG AAGCCCTGGC    1080

TGCAGGCAGC CTTCCAGGCA ATATGAAGAT AGGAGGCCCA CGGGCCTGGC AGTGAGAGGT    1140

GTGGCCCCAC ACCGATTTAT GATATTAAAA TCTCAACTCC CAAAAAAAA AAAAAAAAA      1200

CTGAGACTAG TTCTCTCTCT CTCGAGAACT AGTCTCGAGT TTTTTTTTT TTTTTTTTT      1260

TTTTTTTTT TTTTTTTTG GCTTTAAGGA TTTATTTATT GTTTCCTCTT TACAGTGTCC      1320

ACTTTTCTCT ACTTAATACT ACTTTCCAGT CTCAGAAGCC CAGAGGGAAA AAAAAAAGAC    1380

CATGAATCTT CCTCTCCCAG ATTAAAGTAC ACACTTTGGA AAACAGATTG GAAAACCTTT    1440

CTGAAAAAAG TTGACTGAAA CTCCAAACCA ACATGCCATA TTGTTGATGT TGCTCATGAA    1500

AATTGTTAAA AACCTGTTCT AGATAAAGAA CAGTCTCAAG TTTTTGTACA GCCTACACAT    1560

AGTACAAGGG TCCCCTATGA TGATTCTTCT GTAGGACGAA ATAATGTAAT TTTTTCAGTT    1620

TCTGGTTTAT AACTCTCTCG ATCTCAGAGT TGACTGATTA AACACCTAC TCATGCAACA     1680

GAGAATAAAG CACTCATATT TTTATAAATT ATATGGACCA AACTATTTTG GAAATCTTAT    1740

CTATTGGAGA CACAATATGC TGGACTAAAG CAATAATTAT TTTATTCTCA ATGTCTGTGC    1800

TAACCTCAAT GACTTAGAAT GCTTTGCTAT ATTTTGCCTC TATGCCTCAA CCACACTGGC    1860

TTTCTTTTAG CTCTTGAACA AGCCAAACTG CTTCCTGCCT CAGGACCAGA TATTTTGGGA    1920

CTTCTCTTAA GAATTCTATT TCCTTAATTC TTTATCTGGG TAACTTAGTT TTATCCAACA    1980

CTTCAGATCC TGCCGTAAAA ACTCTTCTTA TAGAAGCCTG TCATGACACT GTCTCTCTTC    2040
```

-continued

```
TCCAACATAC TCACCAGCAC ACATGTAGAC TAGATTAGAA CCTCCTGTTT TTCTTTTTCA    2100

TACTTTTCTC TATCATGCTT CCCTCCATTA TAATATTTTT ATTATGTGTG TGAATGTCTG    2160

CCCCAAGTCA GTTTCCTCAC TAAACTATAA ACTCCGTAAA GCTGGGATCC TTCCAATTTT    2220

GATCACCACT TAGTACAGTA GGAACACAGT AAAGATTCAA TTGGTATTTG TGGAATGAAT    2280

GAATGAATTG TTTTGCTAGT AAAGTCTGGG GGAACCCAGG TGAGAAGAGC CTAGAAAGCA    2340

GGTCGAATCC AAGGCTAGAT AGACTTAGTG TTACTCAAGA AAGGGTAGCC TGAAAATAAA    2400

GGTTCAAATT ATAGTCAAGA ATAGTCAAGA CATGGGCAAG ACAAGAGTGC TGCTCGTGCC    2460

GAATTCGATA TCAAGCTTAT CGATACCGTC GACCTCGAGG GGGGGCCCGG TACCCAATTC    2520

GCCCTATAGT GAGTCGTATT ACAATTCACT GGCCGTCGTT TTACAACGTC GTGACTGGGA    2580

AAACCCTGGC GTTACCCAAC TTAAT                                         2605
```

(2) INFORMATION FOR SEQ ID NO:5:

(i) SEQUENCE CHARACTERISTICS:
        (A) LENGTH: 1288 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: -
        (B) LOCATION: 1..1288
        (D) OTHER INFORMATION: /note= "cDNA clone 41.1 with homology
            to homeobox T shirt gene from
            Drosophila"

(xi) SEQUENCE DESCRIPTION: SEQ ID NO:5:

```
GAGGGCAGCG AGAAGGAGAA ACCCCAGCCC CTGGAGCCCA CATCTGCTCT GAGCAATGGG      60

TGCGCCCTCG CCAACCACGC CCCGGCCCTG CCATGCATCA ACCCACTCAG CGCCCTGCAG     120

TCCGTCCTGA ACAATCACTT GGGCAAAGCC ACGGAGCCCT GCGCTCACC TTCCTGCTCC      180

AGCCCAAGTT CAAGCACAAT TTCCATGTTC CACAAGTCGA ATCTCAATGT CATGGACAAG     240

CCGGTCTTGA GTCCTGCCTC CACAAGGTCA GCCAGCGTGT CCAGGCGCTA CCTGTTTGAG     300

AACAGCGATC AGCCCATTGA CCTGACCAAG TCCAAAAGCA AGAAAGCCGA GTCCTCGCAA     360

GCACAATCTT GTATGTCCCC ACCTCAGAAG CACGCTCTGT CTGACATCGC CGACATGGTC     420

AAAGTCCTCC CCAAAGCCAC CACCCCAAAG CCAGCCTCCT CCTCCAGGGT CCCCCCCATG     480

AAGCTGGAAA TGGATGTCAG GCGCTTTGAG GATGTCTCCA GTGAAGTCTC AACTTTGCAT     540

AAAAGAAAAG GCCGGCAGTC CAACTGGAAT CCTCAGCATC TTCTGATTCT ACAAGCCCAG     600

TTTGCCTCGA GCCTCTTCCA GACATCGAG GGCAAATACC TGCTGTCTGA TCTGGGCCCA      660

CAAGAGCGTA TGCAAATCTC TAAGTTTACG GGACTCTCAA TGACCACTAT CAGTCACTGG     720

CTGGCCAACG TCAAGTACCA GCTTAGGAAA ACGGGCGGGA CAAAATTTCT GAAAACATG      780

GACAAAGGCC ACCCCATCTT TTATTGCAGT GACTGTGCCT CCCAGTTCAG AACCCCTTCT     840

ACCTACATCA GTCACTTAGA ATCTCACCTG GGTTTCCAAA TGAAGGACAT GACCCGCTTG     900

TCAGTGGACC AGCAAAGCAA GGTGGAGCAA GAGATCTCCC GGGTATCGTC GGCTCAGAGG     960

TCTCCAGAAA CAATAGCTGC CGAAGAGGAC ACAGACTCTA AATTCAAGTG TAAGTTGTGC    1020

TGTCGGACAT TTGTGAGCAA ACATGCGGTA AAACTCCACC TAAGCAAAAC GCACAGCAAG    1080

TCACCCGAAC ACCATTCACA GTTTGTAACA GACGTGGATG AAGAATAGCT CTGCAGGACG    1140
```

| AATGCCTTAG TTTCCACTTT CCAGCCTGGA TCCCCTCACA CTGAACCCTT CTTCGTTGCA | 1200 |
| CCATCCTGCT TCTGACATTG AACTCATTGA ACTCCTCCTG ACACCCTGGC TCTGAGAAGA | 1260 |
| CTGCCAAAAA AAAAAAAAAA AAAAATTC | 1288 |

(2) INFORMATION FOR SEQ ID NO:6:

(i) SEQUENCE CHARACTERISTICS:
        (A) LENGTH: 2821 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: -
        (B) LOCATION: 1..2821
        (D) OTHER INFORMATION: /note= "cDNA clone GCAP encodes a
            guanino cyclase activating protein
            (GCAP)"

(xi) SEQUENCE DESCRIPTION: SEQ ID NO:6:

| ATCCTAAGAC GCACAGCCTG GGAAGCCAGC ACTGGGGAAG TGGTGCTGAG GGATGTGGGT | 60 |
| CACTGGGGTG AAGGTGGAGC TTTCAGGGTC TCCCGTCAAT GCAGCTGAGT TTTCTTTGGC | 120 |
| AGGGAATTTA CCAGCTGAAG AAAGCCTGCC GGCGAGAGCT ACAAACTGAG CAAGGCCAGC | 180 |
| TGCTCACACC CGAGGAGGTC GTGGACAGGA TCTTCCTCCT GGTGGATGAG AATGGAGATG | 240 |
| GTAAGAGGGG CAGAGATGGG GAGAGTGCTG TCCACTCTGC ATCATCGCCA CTTTCTGGCC | 300 |
| GCACGTCCTT GGGCAAGGCC CTCCACCTTC AACCCTGGG GTCCTCATCT GTGAGAAGGC | 360 |
| TGTGGAGAAG ATGTCATGAA CTAACAAAGG GACTCATGAG CACGTGTTTG TAGGAGTGAC | 420 |
| TAAAAGTCCT ACAGGAGTTG CTGATGGAGG CCAGGCACGC AGAATAGAAA GAATAGGAAC | 480 |
| TTTGGAGTCA GGCAGGGAGT GATATATTGA GCTTCTCGTC CTAGTCTCAA TTTCCTCATC | 540 |
| TGGAAAATGG GGATAATAAT AGTGGTTGAG AGGAATGAAT AGGATAATGT GTTTAAGAGC | 600 |
| AGGCATAGGG TAGACCTCCA TTCAGGCTGC TTGGGCTTTC CTCCCTGTAG CCCAAAGCCC | 660 |
| AGCCTCAGGG CTATGTGGGG AGAGAGCTGG CTTGGAATAC ACACTTGAGC CCTCCAGCTC | 720 |
| TCTCAGCTCC ACCCAGCATT TCCGTGGTAC CATGCGCAAA AGTAAAACTT CAATTCATCA | 780 |
| GCAAAGAAAG CCCCTTAAAG GTGGCAGGAG ACTCCTGGAG ATTCAGACAC CTGACAAGCC | 840 |
| GCAAGCTTGA GGTCTGAGAC TGCAGGATAG TTGGCATAAG ACGTGTAGGC GCATCCTGGG | 900 |
| AGCGAGGTCT CTCCTCCTGC CCCCAGACCC AGGTCTCCCC TTCTTCTACA TGACCACCTC | 960 |
| TCCTCCCCCT TGCTCAGGCC AGCTGTCTCT GAACGAGTTT GTTGAAGGTG CCCGTCGGGA | 1020 |
| CAAGTGGGTG ATGAAGATGC TGCAGATGGA CATGAATCCC AGCAGCTGGC TCGCTCAGCA | 1080 |
| GAGACGGAAA AGTGCCATGT TCTGAGGAGT CTGGGGCCCC TCCACGACTC CAGGCTCACC | 1140 |
| CAGGTTTCCA GGGTAGTAGG AGGGTCCCCT GGCTCAGCCT GCTCATGCCC ACTCTTCCCC | 1200 |
| TGGTGTTGAC TTCCTGGCAC CCCCTGTGCA GGGCTGAGTG GGGATGGGGA AGGGCTGCTG | 1260 |
| GGTTTGAAGT GGCCAACAGG GCATAGTCCA TTTTGGAGGA GTCCCTGGGA TGGTGAAGGG | 1320 |
| AATTCAGTTA CTTTTCCTGT TCAGCCGCTC CTGGAGGAC TGTGCCTTGG CTGGGTGGTT | 1380 |
| GTGGGGCTCC CACAGTTTCT GGGTGTTCTC AGTTGGAAGC AAGAGCCAAC TGAGGGGTGA | 1440 |
| GGGTCCCACA GACCAAATCA GAAATGAGAA CACAAAGACT GGTAGGAGGC AGGGGTGGGA | 1500 |
| GGGTGTTGAG ACTGAAGAAA AGGCAGGAGT TGCCGGGCAC GGTGGCTCAC GCCTGTAATC | 1560 |
| CCAGCACTTT GGGAGGCCGA GGCGGGCAGA TCACGAGGTC AGGAGATCGA GACCATCCTG | 1620 |

```
GCTAACACGG GGTGAAACCC CGTCTCTACT AAAAATACAA AAAATCAGCC GGGTGAGGTG      1680

GCGGGCGCCT GTAGTCCCAG CTACTCAGGA GGCTGAGGCA AGAGAATGGC GTGAACCCCA      1740

GGGGGCCGAG CCTACAGTGA GCCGAGATTG CGCCACTGCA CTCCAGCCTG GACGACAGTG      1800

AGACTCCGTC TCAAAAAAAA AAAAGAAAG AAAAGAAAAG GCAGGAGTTT TGGGGGGCAG       1860

GGGGCAGCAA TAATTCTATA ACTTCCGGGA TGCTGAGGGG CGTTCATGGG GAGGACCCTG      1920

GCCTCCTCCT CCCCAAGGCA TCCTCACCAG TGGTGTCAAC AGGAAAAATG GCAGCAAATA      1980

CGCTGCAGGC TGTGGTCTTT CTGCCTTTGA AAGGGTCAGC TGTACTTAAA GGGACTGTTT      2040

CAGCTCTGCC TGGGTGCTGC TCTGGGACCC CCTGCTGCCA ACCCACCACT CCCCCAACAA      2100

TCCTCTCTTT CCATCCATAT CCCCCAGTAT GGACCTTCCA CAACTCCCAG CCATAAGCTG      2160

AATGTTTCTC TTTAAAGGAT GGAGAAAACT TCTGTCTGTC TCTGGCAAGA ATTGGGGAC      2220

TGTTGACTGG GATTGTGGGC TGGGCTTGGC TTCTAACTGC TGTGTGACCC AAGACAGCCA      2280

CTTCTCCTCC CTAACCTTGG TTATGTCTTG GCAGCACAGT GAGCAGGTCG GACTAGGCGA      2340

ACAGTTTTGG ATTATTGTGT TTTTAGATGT GGAATTATTT TTTGTTATAT AAACTCTTAT      2400

GTGTAACCCC AATATAGAAA CTAGATTAAA AGGGAGTCTC TCTGGTTGAA AGGGGAGCTG      2460

AGTACCCTCT GGAACTGGAG GCACCTCTGA AAAAGCAAA CTGAAAACCA GTGCCCTGGG       2520

TCACTGTTAC TCCTATAAGA CAGTTTAAAG TGAGACCTGG AAAAACATTT GCTTTACCTT      2580

GAATAGATAG GTTTTTATGT TGGTATATAA GAAATAAAAC TAACCTATTA ACCCTGAGAC      2640

TTTACAGGTG TGTTATTTCA TATGATAGTC ATATAAAATT TCCTTTAGAC ATCAATTTTA      2700

GGTAAAAAAT AATTGATTAG AAAAATATTG GCCAGGTGCA GCAGCTCACA CCTGCAATCC      2760

CAGGACTTTG GGAGGCCGAG GCGGGTGGAT CACCTGAGGT CAGGGGTTCA AGACCAGCCT      2820

G                                                                    2821

(2) INFORMATION FOR SEQ ID NO:7:

(i) SEQUENCE CHARACTERISTICS:
        (A) LENGTH: 1205 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: -
        (B) LOCATION: 1..1205
        (D) OTHER INFORMATION: /note= "cDNA clone 1b4 for a serine
            threonine kinase"

(xi) SEQUENCE DESCRIPTION: SEQ ID NO:7:

GCGCGCGTGA GTCCGCCCCC CCAGTCACGT GACCGCTGAC TCGGGGCGTT CTCCACTATC       60

GCTTACCTAC CTCCCTCTGC AGGAACCCGG CGATATGGCT GCCGCTGTGC CCCGCGCCGC      120

ATTTCTCTCC CCGCTGCTTC CCTTCTCCTG GGCTTCCTGC TCCTCTCCGC TCCGCATGGC      180

GGCAGCGGCC TGCACACCAA GGCGCCCTTC CCCTGGATAC GGTCACTTTC TACAAGGTCA      240

TTCCCAAAAG CAAGTTCGTC TGGTGAAGTT CGACACCCAG TACCCCTACG GTGAGAAGCA      300

GGATGAGTTC AAGCGTCTTC TGAAAACTCG GCTTCCAGCG ATGATCTCTT GGTGGCAGAG      360

GTGGGGATCT CAGATTATGT GACAAGCTGA ACATGGAGCT GAGTGAGAAA TACAAGCTGG      420

ACAAAGAGAG CTACCCATCT TCTACCTCTT CCGGGATGGG GACTTTGAGA ACCCAGTCCC      480

ATACACTGGG GCAGTTAGGT TGGAGCCATC CAGCGCTGGC TGAAGGGGCA AGGGGTCTAC      540
```

```
CTAGGTATGC CTGGTGCCTG CCTGTATACG ACGCCCTGGC CGGGGAGTTC ATCAGGGCCT      600

CTGGTGTGGA GGCCGCCAGG CCCTCTTGAA GCAGGGGCAA GATAACCTCT CAAGTGTGAA      660

GGAGACTCAG AAGAGTGGGC CGAGCAATAC CTGAAGATCA TGGGGAAGAT CTTAGACCAA      720

GGGGAGCACT TCCAGCATCA GAGATGACAC GGATCGCCAG GCTGATTGAG AAGAACAAGA      780

TGAGTGACGG CAGAAGGAGG AGCTCCAGAA GAGCTTAAAC ATCCTGACTG CCTTCCAGAA      840

GAAGGGGGCC GAGAAAGAGG AGCTGTAAAA AGGCTGTCTG TGATTTTCCA GGGTTTGGTG      900

GGGGTAGGGA GGGGANAGTT AACCTGCTGG CTGTGANTCC CTTGTGGAAT ATAAGGGGGY      960

MSKGGGAAAA GWGGTACTAA CCCACGATTC TGAGCCCTGA GTATGCCTGG ACATTGATGC     1020

TAACATGACC ATGCTTGGGA TGTCTCTAGC TGGTCTGGGG ATAGCTGGAG CACTTACTCA     1080

GGTGGCTGGT GAAATGACAC CTCAGAAGGA ATGAGTGCTA TAGAGAGGAG AGAGGAGTGT     1140

ACTGCCCAGG TCTTTGACAG ATGTAATTCT CATTCAATTA AAGTTTCAGT GTTTTGGTTA     1200

AGTGG                                                                 1205

(2) INFORMATION FOR SEQ ID NO:8:

(i) SEQUENCE CHARACTERISTICS:
        (A) LENGTH: 455 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: -
        (B) LOCATION: 1..455
        (D) OTHER INFORMATION: /note= "cDNA clone 20sa7 for a homolog
            of rat gene BEM-1"

(xi) SEQUENCE DESCRIPTION: SEQ ID NO:8:

GAAATCAGAA GTTTAATATG ACACAATTAA ATATATTTGT ATATCTCACA CCGGAGNTTC       60

TCTTCAAACA TAAGGAGTTA GAAATTACAA GTAGGCATAT GCTTCCTATA TTCAGATAAA      120

TTCATTTCGA TTAATTAAAT TCCAGATAGA GAGAAGTAAT TTTCGAAAAA GAAATGATAG      180

CTATATTAAA GCAGATATTC ATTACAATAC CATGTAGAGA CATAAGCAAT ATTTTGGCAT      240

CATTCTGTCC GCTCAGTAGG CCGTGTTCCC TCTGGTAGGG CCTTTGGAGA GTACCATCTA      300

TCTAAGATGG AGGAATGCTG TGGGAAGGGC GGGATGGAGG TGCGTTTTCT ACGCTGAACC      360

CCACACAGGA AATCTGCAGC CCACACAGCT GCCTCTGCGC CGCCTTCCAT GTGATCATCC      420

TGGTCAATGA AGTGAATTGT CCTATTTCNG GGGGT                                 455

(2) INFORMATION FOR SEQ ID NO:9:

(i) SEQUENCE CHARACTERISTICS:
        (A) LENGTH: 10365 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: -
        (B) LOCATION: 1..10365
        (D) OTHER INFORMATION: /note= "genomic sequence encoding zinc
            finger amplified in breast cancer
            (ZABC-1) gene"

(xi) SEQUENCE DESCRIPTION: SEQ ID NO:9:
```

```
CCATCATATT TCTTATTTTT TTGGGCGGAG AGGGGAGACT TGCTCTGTTG CCCAGGCTGG    60
ACCAGTGGTG CGATCTTGGC TCACTGCAAC CTCCACCTCC TGGGTTCAAG TGATTCCCAA   120
ATAGCTGGGA TTACAGGTGT GTATTACCAT GCCCAGCTAA TTTTTGTATT TTTAGCAGAT   180
AAGGGGTTTC ACCATGTTGG CCAGGCTGGT CTCCAACTCC TGGCCTCATG TGATCCACCC   240
ACTTCGGCTT CCCAAAGCAT TGGGAGTATA GGTGTGAGCC ACTATACCCG TCCTCACATC   300
ATATTTCTAA TCCCGAGACT GTAGAGCTGG TGTCTCTTTT TCTAAAGGAT GTCAGTAGAG   360
AAGTGGAGTT CCCCAAAATT ACAGTTTCAC GTATTAGTCA AGTTTCTAAA ATACAGTAAT   420
AATGTTGAGA GCTGACATAG GGACTAACTT GGTTTTTTTT TTTTTTTTT TTTTTCAAAT   480
TCTCACTGAA CTTTGATTTT GCTAAATAAG GACATTAAAA AAAAAACCAA AAAACTCCAC   540
TATTGCCTAT TGCCACTATT TGATTTTTTA AAAATAAGC GTATTTTAGC ATCTAAAAGT   600
AGGAAGGACC TCAAATAAAT GAGTCTTTGT TCTTGGCCAG GGAAACAGC GTTGTCAGAA   660
TTTGATAACT GTTTTTCTAG GGTATGTGCT GTTATTCAGT TAAAACCTTG CCTGGGACGC   720
TAGCATTCAG TAAATACTTG TTGAATAAGC AAATGAAACT TAAGCTTCTA TGTATAGAAA   780
CCTAAGTCAC TTCACATTCT GATTAGCAGA GTAATTGAAT ATTCTTTTCA ATGTGTAGCT   840
CTATCCCCAG AACCACAGAA TATTGGAACT GTAAAGGCCA TCCTATAGTT TAACCAACTG   900
CGTTAAAATAG ATAATAGAAA GATGTGGTAT GTGGCAGTGA CAACTTGAAG GTTGTGACTA   960
GAACTCGGGT CTCTGGAGTG TTCTATTATA TCACACCAAG CTGGTCACCA GCCCATGTGT  1020
TGATCCTCCA TTGTGATAGC AACAAAGAAA AGACTTCAGG ACATTCTTTC CTTTACCCTA  1080
ATCCTTGATC TGCAGTCTTA TTTAGAAAAG CTTAATGTTA AAGATCTAGT TTATTCAAAA  1140
CTAAAGATAA CAAGGAGTAT GAGAATTTCT ATTTCGGAGT GTAAAGGAGG AGATGTTTCC  1200
TTGGCTTCTC TGAGCCTGCA GGCCTTCCTT GCTCTTTAAG GAAGTAGAGA GAGGGAGGAA  1260
AGTAAAGTAT GCTTTTGTTT TTTAAGGTTA CTTTGCTGGG AGTAGTTTGC ATGCCTTTTG  1320
GTTTTCTTGG GTGGAATTAA CTGACTTAAG TTTTAAGTAG TTGGGACTAT TTAAAAACAA  1380
TGCCTATCCA ATGTTTGCCA TAAAGGCAGA GGGTATTGGC TTTAGAAGTT AATTCTTCTC  1440
CAGGAGTGAA AATTAGCTTC TAAACCAGAA GCAGCAGAGC TAAATAAAGT AATTTTCCAC  1500
CTGGCCAGTG CATGATGTGA AAGGTAGATT AAAAAAATGA GAGGGCCCAT TTTCTGATGA  1560
AAGACTAAGC CATGTTGAAA CAGCCCTGTT GAGGATTTTA TTTTAAATCT ATACATTCAC  1620
AAAGGAGCTT TGTGTATGTC TTTCCCTATT TGTTGTTTGG ACTAGGAAGC CCCACCCAGT  1680
GCTTGTTGAA GGCAGAAAGT CGTTGAAAGC AAGCTGGGAT TTGAACAGTG GATTGAGGTT  1740
TCGAATATCC AGTGAACCAA AATATATCAG GGTTCCCCTG GCCAAGATGA GTGACCATTC  1800
TGAGGTGTTA AGTATTTCTT GAATGGGGAT TTTAGGAAAA GTTTCTGTAT TTCTGTGCTC  1860
ATTTTGTTGA CCTCTGTATG TGCAAAATCT CTAAGGGGGT GTTTGGGCAC TTAGATTTCT  1920
TGGATGCAGA TTTGTTTGTA TATGAAACAA ATTTTAAATT GTTTTGTATA CACTGGATTT  1980
AAAATAGTTT ACTAAAGTGT TTTAATTTTT TCATCTTAAT TTTCACAGTT CTTATAGTCT  2040
TTAGATTTAG GGAGGCTGTT GATGGCATCC ACATGTGCAT TTTAGTGGCA TTTAAAATGT  2100
ATTCAGCTGA ATTTAACAAT TTCTGACCTA AAACTTGACA TTTTAGATTT AAGTCGGTAA  2160
AGCACTGATT TAAACTGGAT TTTAACTGGA TGAAATTCTG ATTTAATAAG TGTACTGACT  2220
GGATAAAATG CCAATGATTT AATTAACAAG CACGTTAAC AGGATGCCCT ATATATTAGT  2280
TAAAAGTGAA GCAATTGAAT TAGGTACCTT CTCTGCTGCG TGGAAAAGAC CGTATGACTC  2340
```

-continued

```
ACCCACACCA GCCTTCTCTT CGCTCTGAGT GTAGCTAACC GTTTCTGTTT TTTTTCCTCT    2400

AGGGTTTGGA AATCCCTTGT CTCCAGGTTG CTGGGATTGA CTTCTTGCTC AATTGAAACA    2460

CTCATTCAAT GGAGACAAAG AGAACTAATG CTTTGTGCTG ATTCATATTT GAATCGAGGC    2520

ATTGGGAACC CTGTATGCCT TGTTTGTGGA AGAACCAGT GACACCATCA CTGAGCTTCC     2580

TAAAAGTTCG AAGAAGTTAG AGGACTATAC ACTTTCTTTT GAACTTTTAT AATAAATATT    2640

TGCTCTGGTT TTTGGAACCC AGGGCTGTTA GAGGGGTGAG TGACAAGTCT TACAAGTGGC    2700

CTTATTCCAA CTCCAGAAAT TGCCCAACGG AACTTTGAGA TTATATGCAA TCGAAAGTGA    2760

CAGGAAACAT GCCAACTCAA TCCCTCTTAA TGTACATGGA TGGGCCAGAA GTGATTGGCA    2820

GCTCTCTTGG CAGTCCGATG GAGATGGAGG ATGCCTTGTC AATGAAAGGG ACCGCTGTTG    2880

TTCCATTCCG AGCTACACAA GAAAAAAATG TCATCCAAAT CGAGGGGTAT ATGCCCTTGG    2940

ATTGCATGTT CTGCAGCCAG ACCTTCACAC ATTCAGAAGA CCTTAATAAA CATGTCTTAA    3000

TGCAACACCG GCCTACCCTC TGTGAACCAG CAGTTCTTCG GGTTGAAGCA GAGTATCTCA    3060

GTCCGCTTGA TAAAAGTCAA GTGCGAACAG AACCTCCCAA GGAAAAGAAT TGCAAGGAAA    3120

ATGAATTTAG CTGTGAGGTA TGTGGGCAGA CATTTAGAGT CGCTTTTGAT GTTGAGATCC    3180

ACATGAGAAC ACACAAAGAT TCTTTCACTT ACGGGTGTAA CATGTGCGGA AGAAGATTCA    3240

AGGAGCTTTG GTTTCTTAAA AATCACATGC GGACACATAA TGGCAAATCG GGGGCCAGAA    3300

GCAAACTGCA GCAAGGCTTG GAGAGTAGTC CAGCAACGAT CAACGAGGTC GTCCAGGTGC    3360

ACGCGGCCGA GAGCATCTCC TCTCCTTACA AAATCTGCAT GGTTTGTGGC TTCCTATTTC    3420

CAAATAAAGA AAGTCTAATT GAGCACCGCA AGGTGCACAC CAAAAAAACT GCTTTCGGTA    3480

CCAGCAGCGC GCAGACAGAC TCTCCACAAG GAGGAATGCC GTCCTCGAGG GAGGACTTCC    3540

TGCAGTTGTT CAACTTGAGA CCAAAATCTC ACCCTGAAAC GGGGAAGAAG CCTGTCAGAT    3600

GCATCCCTCA GCTCGATCCG TTCACCACCT TCCAGGCTTG GCAGCTGGCT ACCAAAGGAA    3660

AAGTTGCCAT TTGCCAAGAA GTGAAGGAAT CGGGGCAAGA AGGGAGCACC GACAACGACG    3720

ATTCGAGTTC CGAGAAGGAG CTTGGAGAAA CAAATAAGGG CAGTTGTGCA GGCCTCTCGC    3780

AAGAGAAAGA GAAGTGCAAA CACTCCCACG GCGAAGCGCC CTCCGTGGAC GCGGATCCCA    3840

AGTTACCCAG TAGCAAGGAG AAGCCCACTC ACTGCTCCGA GTGCGGCAAA GCTTTCAGAA    3900

CCTACCACCA GCTGGTCTTG CACTCCAGGG TCCACAAGAA GGACCGGAGG GCCGGCGCGG    3960

AGTCGCCCAC CATGTCTGTG GACGGGAGGC AGCCGGGGAC GTGTTCTCCT GACCTCGCCG    4020

CCCCTCTGGA TGAAAATGGA GCCGTGGATC GAGGGGAAGG TGGTTCTGAA GACGGATCTG    4080

AGGATGGGCT TCCCGAAGGA ATCCATCTGG GTAAGCTGCC CTGTCTCCGT CCCGTGCTGT    4140

TCCGCCTGTG TCTGTCTGTC TCCCCGTCTC CCCCTCTCTA TTCCCATCTC CAGACAACGC    4200

TGGCCAGGAA TGGGGTTTGG AGAGCCAGAG TCAAGTCCAG GCTCTTTTTG GTATCACTCT    4260

GTGTAAGTCA TTTAACCTCT CAGGGCCTTA ATTTTCTCAT TTCTGTAATA ACAGGGTTGA    4320

GTTAAGAGGT CTCCTTGTTC TGAAAATATA TATATATTTT TTAAACGTGT ATCGTTTTGC    4380

TCACAAAACA CACTTTAAAA AAAAAATAAC TTGTGCATCC AGCCCAAATG CACTGCTTCT    4440

TAACTGGGGC GATTTTGTTC CCAATCAGTA TCTGGCAATG TCTGGAGGCA TTTTGGTTGT    4500

CATACTGTGT GTGTGGGTGT GCCTGCTGGC ATCCAGTGGG CAGAGGCCAG GGACACTGCT    4560

CAGCATGGTA CAGTGCACAG GACAGCCCCA TCATCAAAGA ATTATCTGGT CCCAAATGTC    4620

AATAGTTTGA GCATTGAGAG ACCCTAGCCT TCACTTAAGT TTTTCTGGCG TTCCTGATCT    4680

TTTTCTGTAG TGAATTTCTA GTGGCCATAA AAGGTACTGG GAGTGATCAA CTAGAGCCAG    4740
```

```
GAATATTATT TGGGCAGCCG TTTGGTGCTG TCCAAAACCT TGTCCTTTCT GTCTGGCAAG      4800

CTAGTATCCA TTTATAGGTA CCTCAGGAAC CCAAATGATT TGTCATAAAA TACAAGGAAT      4860

GTGAGCACAC TGAAGACATT TTTAAGAAGG CTCATTTGCT CAGCAGAATT TTCAGTGTAC      4920

TAGTGGCATT TATAGAAAGA GAAGGTGATC ACTGAAGGCA TGCTCACATA ATATTCCTGA      4980

GCCCTGGTGG GCGTTATCTA GGGCAAAGGA TTCCACCTGT GTTTGGAGTT GCGCCCATCC      5040

TCACTGTAGC CAGAGCTTCT CCTATCAGAG TTTAGTATTT TGTTTGAATA GAGGATCTTG      5100

CTGCTTAAAA CAGTTGAAAA GACCCTGATG GGCAGGCCGT AATTGACAAG CGAATGATGG      5160

GAACATGAAT CGGTCTTAGG GAAGCATCTG TCAAAGTGGT CCTTGGTTAA AACAAGTGCC      5220

TCCTCCTCTC AGTGTCACTT GATTGTGTGC TTGAATTCTT CGGAAAACTG GGTGTATGAG      5280

ACCCACGATG AATTTGCCCA CACGATTGAT TGGACTCTTC CTTCACCTGC TCTTCAGCCA      5340

GTGCCAGTTC CTTTTCTGAT CATGTGATTG ACGTGAGAAC TGTAGTCTGT ATATCAAATC      5400

TTTAGAATGT TTTTGAGTTT CCTGGGACAC AGGAAACCCA GCACTTAGCA TACTACAAAT      5460

CTAATGTCTT AATGGCATCA TAAAAGAGG CTTTAAACAC AGACTCCAGT TAGCTAAGTG       5520

GTTTCTGCTA GTGCCGGTAC TGTTGCAGGG GCCCTGTGAG ATGCCCCAGT TCCCTGAAAG      5580

AAATGAAAAG GCCAGTTACC GGTAGGTGGT GTGGAAAACA TGGGCTAGAT CATCAGGCAG      5640

GACAGAATGC CTGGCTGTGG GTGGGAGCAC CCCAGCTTGG CGTTGAGTTC TGGTTCTACC      5700

ACTGCGTTGT TTTGTGACCA ATTATGAGTT GCTTAACCTT TCTTTGCTAC TATTTCCCTG      5760

TTTGCAAAAT GGTTCATTGA CCCCTGTCTT CCACCTCCCA AGGACAATTT CAACAGCCTA      5820

TTTGTAAAAA GATCACAGTC CTTTAAAAAA TATAACTGTA AAGTCAGAGG TGATGCTTGA      5880

AAGAGCAGGA ACCAGGTAGA TGTGGAAATG TCATGTCCTT TGTTCTAAAG AAAAGGCATT      5940

TCATAGCTTT TTGGATATGA CGCAACATAC CATAAATCCT GACACATAGT TGGGAGTCGG      6000

AAATTGCAAC AACGCCCAGT TATAAACCCA GCTAGTTTGG GTATGATTGT AAGAAAAAAA      6060

AGCTGGCCAT TCTGTATTTG GGGAATTGAT TTTCCTAAAC TTATATTATC TTAGTAGTCT      6120

AGATTTATCA TATTGTACTA TCATCCTGGC TTTTTTAAGA CTTAAGAAGA TCAAGTAAAT      6180

TTTTTTTTCT TTCTTTAGAC ACTATATAGA TCATCAAGGG TGTCTGTCTT ACAGGTGGAT      6240

AGTGATATGA TCTACAGTGA GGGGACATTT ATTTAAAACT TAAACATTCA TGTGTTTTGG      6300

GGGTGGTATT TTAACGGCAG CACCTCTGAT TGTCTTTTGG AGGGCTGGTG TGTGTTTGAA      6360

GTTCTGTCCT CCTTCCAGTG GACTCTAACT TCTCCTGATG CACGTGAGAC ACATTGTCCT      6420

ATTGTCCTGC AGAAACTAAA GCCAAACACT GTCATCTGGG GACAGGTTTT CATTTGTCAG      6480

ATCTCTTTCG CCCACATGAG TGTTTGTGGA CAATACAGCC TGCTTTCCAA AACTTTGCTA      6540

AATTTTGACA GACTTTCCTA GGTGCTTGCC CAATGCCAGA CTTTCTTTTC TGTTGAAGAT      6600

TAAGTTGTGC TTGCTGCCCT CTAGTGGTCA GTTGTTTAAT CCTAACCTTA AACGGCTTAT      6660

TTTTCCCCTG GTGGTTGGGA AGTTGACGGT TTGTAATTGG CTCATTTTTC TAAATTATTC      6720

TGAAGAAGAT AATTTTTCCC GCCAGTATGT ATGTCCACCT TCAGTTTGCC AGATCCTGCC      6780

TGCTCAGAGA CACTGAGAAC CGGAAGCTGC CCGGGCAATT CAGTCTATGA AATGATCTTT      6840

CTTGTGATTA AGGCAAACGA AGAACTGAAT GTTTAATAGT GTACTCTGCT GTACCCAGAA      6900

AAAAACAAAA CAAAATCATG TTATAACACT CTAAAACTTC AAACAACCTC CAACAGCATT      6960

TGGTGTGTGT CTAGCCGTTT TGTTCTAACC CGATGTTATA TAAAAGAATT TTTTCATGCT      7020

TTCCAAAAAT GTTTATGTCA AGAATATTTA AGTCAGCATG CCTTATTCAG GTACTTCAGC      7080
```

```
TACCTTCTTA TATAAATATT TTTGTTTTTC CTTTAAGATA AAAATGATGA TGGAGGAAAA    7140

ATAAAACATC TTACATCTTC AAGAGAGTGT AGTTATTGTG GAAAGTTTTT CCGTTCAAAT    7200

TATTACCTCA ATATTCATCT CAGAACGCAT ACAGGTAAAG AACTTTTATT TTTTTAACCA    7260

TGCATTAGTT AAATTATGTA GTTATCTAAT TTTTTTGTTG TTGTTGTTCA GATACTCTGC    7320

CAGATCCTTG GACTAGCTTA AGGATAAATA TGTAGCATGT TGATTGCAGT GGTTATTTTT    7380

ATTCTTTTAG TGCCATTGTA ACTTGAGCCA TTGTTCTTAT TTGCAGTTCA TTTCTTTTCT    7440

TTCTTTTTTG TTTTTTGAGA CGGAGTCTTG CTCTGTCACC TCGGCTGGAG TGCAGTGGTG    7500

CAATTTCGGC TCACTGCAGC CTCCACCTCC CTGGTTCAAG CAATACTCCT GCCTCAGCCT    7560

CCCCAGTAGT TGGGATTACA GGTACCTGCC ACCACACCCG GCTAATTTCT GTATTTTTAG    7620

TAGAGATGGG GTTTCACCAT GCTGGCCAGG CTGGTTTCGA ACTCCTGACC TCAAGTGATC    7680

CGCTCACCTT GGCCTCCCAT AGTGTTGGCC TCCCATAGTG CTGGGATTAC AGGCGTGAGC    7740

CACCGCGCCC GGACAAAGTT CATTTGTTTA GTTTATGACT GCTATGTCCT GACTCTTATC    7800

TTATTAAAAG CTACAGTATT TTAAAATGCT GCATCTTATG TCTTTATGAT TGAGAATGAA    7860

ATGAGAATCT ATTTAGTAGT CTTGAGATTG TGAAAGGAGC TATGACATCA TGATGTAGGA    7920

GGCTGCGTAG ATTTGAAATT TCATCTCTTC CACTTACTAT CTGTGCACCC TTGGGCAAGT    7980

TATTTAACCT TTTTGTGCTT TTAGTTTTCT TTGCTGTAAA AGTAGAATAA TACATATTTC    8040

CCTAGGGCTG TTAGGAAGAT TAAATAAGTT AGAAGTGTTG CTGTTAATTT TTCTATTGAA    8100

GATAGGCATT CATAATTTCA AATATTCATT ACAGTAAGGA TGATAAAGAA CTGATGAGAA    8160

ATCCTATGTG ATAGTAGATC GAGAAAGCAA AAGGAGGAAA GAAGCCTGTT TTCTTAATAA    8220

ATAGATATTT GATCTATTTC AGTGCTTTTC ATACACTTCT ATAATAAAGT GCCATTTCTT    8280

GCCTTAGGTG AAAAACCATA CAAATGTGAA TTTTGTGAAT ATGCTGCAGC CCAGAAGACA    8340

TCTCTGAGGT ATCACTTGGA GAGACATCAC AAGGAAAAAC AAACCGATGT TGCTGCTGAA    8400

GTCAAGAACG ATGGTAAAAA TCAGGACACT GAAGATGCAC TATTAACCGC TGACAGTGCG    8460

CAAACCAAAA ATTTGAAAAG ATTTTTTGAT GGTGCCAAAG ATGTTACAGG CAGTCCACCT    8520

GCAAAGCAGC TTAAGGAGAT GCCTTCTGTT TTTCAGAATG TTCTGGGCAG CGCTGTCCTC    8580

TCACCAGCAC ACAAAGATAC TCAGGATTTC CATAAAAATG CAGCTGATGA CAGTGCTGAT    8640

AAAGTGAATA AAAACCCTAC CCCTGCTTAC CTGGACCTGT TAAAAAAGAG ATCAGCAGTT    8700

GAAACTCAGG CAAATAACCT CATCTGTAGA ACCAAGGCGG ATGTTACTCC TCCTCCGGAT    8760

GGCAGTACCA CCCATAACCT TGAAGTTAGC CCCAAAGAGA AGCAAACGGA GACCGCAGCT    8820

GACTGCAGAT ACAGGCCAAG TGTGGATTGT CACGAAAAAC CTTTAAATTT ATCCGTGGGG    8880

GCTCTTCACA ATTGCCCGGC AATTTCTTTG AGTAAAAGTT TGATTCCAAG TATCACCTGT    8940

CCATTTGTA CCTTCAAGAC ATTTTATCCA GAAGTTTTAA TGATGCACCA GAGACTGGAG    9000

CATAAATACA ATCCTGACGT TCATAAAAAC TGTCGAAACA AGTCCTTGCT TAGAAGTCGA    9060

CGTACCGGAT GCCCGCCAGC GTTGCTGGGA AAAGATGTGC CTCCCCTCCC TAGTTTCTGT    9120

AAACCCAAGC CCAAGTCTGC TTTCCCGGCG CAGTCCAAAT CCCTGCCATC TGCGAAGGGG    9180

AAGCAGAGCC CTCCTGGGCC AGGCAAGGCC CCTCTGACTT CAGGGATAGA CTCTAGCACT    9240

TTAGCCCCAA GTAACCTGAA GTCCCACAGA CCACAGCAGA ATGTGGGGGT CCAAGGGGCC    9300

GCCACCAGGC AACAGCAATC TGAGATGTTT CCTAAAACCA GTGTTTCCCC TGCACCGGAT    9360

AAGACAAAAA GACCCGAGAC AAAATTGAAA CCTCTTCCAG TAGCTCCTTC TCAGCCCACC    9420

CTCGGCAGCA GTAACATCAA TGGTTCCATC GACTACCCCG CCAAGAACGA CAGCCCGTGG    9480
```

-continued

```
GCACCTCCGG GAAGAGACTA TTTCTGTAAT CGGAGTGCCA GCAATACTGC AGCAGAATTT    9540

GGTGAGCCCC TTCCAAAAAG ACTGAAGTCC AGCGTGGTTG CCCTTGACGT TGACCAGCCC    9600

GGGGCCAATT ACAGAAGAGG CTATGACCTT CCCAAGTACC ATATGGTCAG AGGCATCACA    9660

TCACTGTTAC CGCAGGACTG TGTGTATCCG TCGCAGGCGC TGCCTCCCAA ACCAAGGTTC    9720

CTGAGCTCCA GCGAGGTCGA TTCTCCAAAT GTGCTGACTG TTCAGAAGCC CTATGGTGGC    9780

TCCGGGCCAC TTTACACTTG TGTGCCTGCT GGTAGTCCAG CATCCAGCTC GACGTTAGAA    9840

GGTATTGCAT GAGGGGCGTC GTGTTTAAAT GGCTGCCTAC AGTGATTAAT AGCTAATCCA    9900

GGCATTCTCA GTGGAGATGG TACCACTCCC AAGGGTGGGG GGTAGGCAGC CAGAAGTTCT    9960

TGGGGGTCAC AGAGAGAAGC ATTCTTAGAT ACGGCAGTGG TTTGTGGTCC TCCAAGGCTT   10020

ACTTAACTCT GTGGGTTTAA CTCTTAACCC TGTGTATTTT ATTCTTTTGA TTTGTTTAGT   10080

CTTACTTTAT TTTTAGAGAA AGGGTCTTGC TCCGTCATCT AGATTGGAGT GCAGCGGTGT   10140

AATCATAGCT TACTGTAGTC TTGAATTCCT GAGTTCAAGA GATCCTTCTG CCTCAGCTTC   10200

CCAGGTAGCT GAGACTATAT GTGCTGCTAC CATGCACAGC TGATTTTTAA ATTTTTTTTG   10260

TAGAGATGGA GTTGCCCAGG CTGGTCTTGA ACTCCTGGCC TGAGGTGATC CTCCTGCGTT   10320

GACCTCCCAA GTATCTTAGA CTACAGATGC ACTCCACCAC GCTTG                   10365

(2) INFORMATION FOR SEQ ID NO:10:

(i) SEQUENCE CHARACTERISTICS:
        (A) LENGTH: 3186 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: -
        (B) LOCATION: 1..3186
        (D) OTHER INFORMATION: /note= "ZABC-1 open reading frame"

(xi) SEQUENCE DESCRIPTION: SEQ ID NO:10:

ATGCAATCGA AAGTGACAGG AAACATGCCA ACTCAATCCC TCTTAATGTA CATGGATGGG     60

CCAGAAGTGA TTGGCAGCTC TCTTGGCAGT CCGATGGAGA TGGAGGATGC CTTGTCAATG    120

AAAGGGACCG CTGTTGTTCC ATTCCGAGCT ACACAAGAAA AAAATGTCAT CCAAATCGAG    180

GGGTATATGC CCTTGGATTG CATGTTCTGC AGCCAGACCT TCACACATTC AGAAGACCTT    240

AATAAACATG TCTTAATGCA ACACCGGCCT ACCCTCTGTG AACCAGCAGT TCTTCGGGTT    300

GAAGCAGAGT ATCTCAGTCC GCTTGATAAA AGTCAAGTGC GAACAGAACC TCCCAAGGAA    360

AAGAATTGCA AGGAAAATGA ATTTAGCTGT GAGGTATGTG GCAGACATT TAGAGTCGCT    420

TTTGATGTTG AGATCCACAT GAGAACACAC AAAGATTCTT TCACTTACGG GTGTAACATG    480

TGCGGAAGAA GMTTSRRSSA GCCTTGGTTT CTTAAAAATC ACATGCGGAC ACATAATGGC    540

AAATCGGGGG CCAGAAGCAA ACTGCAGCAA GGCTTGGAGA GTAGTCCAGC AACGATCAAC    600

GAGGTCGTCC AGGTGCACGC GGCCGAGAGC ATCTCCTCTC CTTACAAAAT CTGCATGGTT    660

TGTGGCTTCC TATTTCCAAA TAAAGAAAGT CTAATTGAGC ACCGCAAGGT GCACACCAAA    720

AAAACTGCTT TCGGTACCAG CAGCGCGCAG ACAGACTCTC ACAAGGAGG AATGCCGTCC    780

TCGAGGGAGG ACTTCCTGCA GTTGTTCAAC TTGAGACCAA AATCTCACCC TGAAACGGGG    840

AAGAAGCCTG TCAGATGCAT CCCTCAGCTC GATCCGTTCA CCACCTTCCA GGCTTGGCAG    900
```

```
CTGGCTACCA AAGGAAAAGT TGCCATTTGC CAAGAAGTGA AGGAATCGGG GCAAGAAGGG      960

AGCACCGACA ACGACGATTC GAGTTCCGAG AAGGAGCTTG GAGAAACAAA TAAGGGCAGT     1020

TGTGCAGGCC TCTCGCAAGA GAAAGAGAAG TGCAAACACT CCCACGGCGA AGCGCCCTCC     1080

GTGGACGCGG ATCCCAAGTT ACCCAGTAGC AAGGAGAAGC CCACTCACTG CTCCGAGTGC     1140

GGCAAAGCTT TCAGAACCTA CCACCAGCTG GTCTTGCACT CCAGGGTCCA CAAGAAGGAC     1200

CGGAGGGCCG GCGCGGAGTC GCCCACCATG TCTGTGGACG GGAGGCAGCC GGGGACGTGT     1260

TCTCCTGACC TCGCCGCCCC TCTGGATGAA AATGGAGCCG TGGATCGAGG GGAAGGTGGT     1320

TCTGAAGACG GATCTGAGGA TGGGCTTCCC GAAGGAATCC ATCTGGATAA AAATGATGAT     1380

GGAGGAAAAA TAAAACATCT TACATCTTCA AGAGAGTGTA GTTATTGTGG AAAGTTTTTC     1440

CGTTCAAATT ATTACCTCAA TATTCATCTC AGAACGCATA CAGGTGAAAA ACCATACAAA     1500

TGTGAATTTT GTGAATATGC TGCAGCCCAG AAGACATCTC TGAGGTATCA CTTGGAGAGA     1560

CATCACAAGG AAAAACAAAC CGATGTTGCT GCTGAAGTCA AGAACGATGG TAAAAATCAG     1620

GACACTGAAG ATGCACTATT AACCGCTGAC AGTGCGCAAA CCAAAAATTT GAAAAGATTT     1680

TTTGATGGTG CCAAAGATGT TACAGGCAGT CCACCTGCAA AGCAGCTTAA GGAGATGCCT     1740

TCTGTTTTTC AGAATGTTCT GGGCAGCGCT GTCCTCTCAC CAGCACACAA AGATACTCAG     1800

GATTTCCATA AAAATGCAGC TGATGACAGT GCTGATAAAG TGAATAAAAA CCCTACCCCT     1860

GCTTACCTGG ACCTGTTAAA AAAGAGATCA GCAGTTGAAA CTCAGGCAAA TAACCTCATC     1920

TGTAGAACCA AGGCGGATGT TACTCCTCCT CCGGATGGCA GTACCACCCA TAACCTTGAA     1980

GTTAGCCCCA AGAGAAGCA AACGGAGACC GCAGCTGACT GCAGATACAG GCCAAGTGTG     2040

GATTGTCACG AAAAACCTTT AAATTTATCC GTGGGGCTC TTCACAATTG CCCGGCAATT     2100

TCTTTGAGTA AAAGTTTGAT TCCAAGTATC ACCTGTCCAT TTTGTACCTT CAAGACATTT     2160

TATCCAGAAG TTTTAATGAT GCACCAGAGA CTGGAGCATA AATACAATCC TGACGTTCAT     2220

AAAAACTGTC GAAACAAGTC CTTGCTTAGA AGTCGACGTA CCGGATGCCC GCCAGCGTTG     2280

CTGGGAAAAG ATGTGCCTCC CCTCTCTAGT TTCTGTAAAC CCAAGCCCAA GTCTGCTTTC     2340

CCGGCGCAGT CCAAATCCCT GCCATCTGCG AAGGGGAAGC AGAGCCCTCC TGGGCCAGGC     2400

AAGGCCCCTC TGACTTCAGG GATAGACTCT AGCACTTTAG CCCCAAGTAA CCTGAAGTCC     2460

CACAGACCAC AGCAGAATGT GGGGGTCCAA GGGGCCGCCA CCAGGCAACA GCAATCTGAG     2520

ATGTTTCCTA AAACCAGTGT TTCCCCTGCA CCGGATAAGA CAAAAAGACC CGAGACAAAA     2580

TTGAAACCTC TTCCAGTAGC TCCTTCTCAG CCCACCCTCG GCAGCAGTAA CATCAATGGT     2640

TCCATCGACT ACCCCGCCAA GAACGACAGC CCGTGGGCAC CTCCGGGAAG AGACTATTTC     2700

TGTAATCGGA GTGCCAGCAA TACTGCAGCA GAATTTGGTG AGCCCCTTCC AAAAAGACTG     2760

AAGTCCAGCG TGGTTGCCCT TGACGTTGAC CAGCCCGGGG CCAATTACAG AAGAGGCTAT     2820

GACCTTCCCA AGTACCATAT GGTCAGAGGC ATCACATCAC TGTTACCGCA GGACTGTGTG     2880

TATCCGTCGC AGGCGCTGCC TCCCAAACCA AGGTTCCTGA GCTCCAGCGA GGTCGATTCT     2940

CCAAATGTGC TGACTGTTCA GAAGCCCTAT GGTGGCTCCG GCCACTTTA CACTTGTGTG     3000

CCTGCTGGTA GTCCAGCATC CAGCTCGACG TTAGAAGGTC TTGGTGGATG TCAGTGCTTA     3060

CTCCCCATGA AATTAAATTT TACTTCATCC TTTGAGAAGC GAATGGTGAA AGCTACTGAA     3120

ATAAGCTGTG ATTGTACTGT ACATAAAACA TATGAGGAAT CTGCAAGGAA CACTACAGTT     3180

GTGTAA                                                                3186
```

(2) INFORMATION FOR SEQ ID NO:11:

(i) SEQUENCE CHARACTERISTICS:
        (A) LENGTH: 1061 amino acids
        (B) TYPE: amino acid
        (C) STRANDEDNESS: single
        (D) TOPOLOGY: linear (ii) MOLECULE TYPE: protein (ix) FEATURE:
        (A) NAME/KEY: -
        (B) LOCATION: 1..1061
        (D) OTHER INFORMATION: /note= "ZABC-1 protein"

(xi) SEQUENCE DESCRIPTION: SEQ ID NO:11:

```
Met Gln Ser Lys Val Thr Gly Asn Met Pro Thr Gln Ser Leu Leu Met
1               5                   10                  15

Tyr Met Asp Gly Pro Glu Val Ile Gly Ser Ser Leu Gly Ser Pro Met
            20                  25                  30

Glu Met Glu Asp Ala Leu Ser Met Lys Gly Thr Ala Val Val Pro Phe
        35                  40                  45

Arg Ala Thr Gln Glu Lys Asn Val Ile Gln Ile Glu Gly Tyr Met Pro
    50                  55                  60

Leu Asp Cys Met Phe Cys Ser Gln Thr Phe Thr His Ser Glu Asp Leu
65                  70                  75                  80

Asn Lys His Val Leu Met Gln His Arg Pro Thr Leu Cys Glu Pro Ala
                85                  90                  95

Val Leu Arg Val Glu Ala Glu Tyr Leu Ser Pro Leu Asp Lys Ser Gln
            100                 105                 110

Val Arg Thr Glu Pro Pro Lys Glu Lys Asn Cys Lys Glu Asn Glu Phe
        115                 120                 125

Ser Cys Glu Val Cys Gly Gln Thr Phe Arg Val Ala Phe Asp Val Glu
    130                 135                 140

Ile His Met Arg Thr His Lys Asp Ser Phe Thr Tyr Gly Cys Asn Met
145                 150                 155                 160

Cys Gly Arg Xaa Xaa Xaa Xaa Pro Trp Phe Leu Lys Asn His Met Arg
                165                 170                 175

Thr His Asn Gly Lys Ser Gly Ala Arg Ser Lys Leu Gln Gln Gly Leu
            180                 185                 190

Glu Ser Ser Pro Ala Thr Ile Asn Glu Val Val Gln Val His Ala Ala
        195                 200                 205

Glu Ser Ile Ser Ser Pro Tyr Lys Ile Cys Met Val Cys Gly Phe Leu
    210                 215                 220

Phe Pro Asn Lys Glu Ser Leu Ile Glu His Arg Lys Val His Thr Lys
225                 230                 235                 240

Lys Thr Ala Phe Gly Thr Ser Ser Ala Gln Thr Asp Ser Pro Gln Gly
                245                 250                 255

Gly Met Pro Ser Ser Arg Glu Asp Phe Leu Gln Leu Phe Asn Leu Arg
            260                 265                 270

Pro Lys Ser His Pro Glu Thr Gly Lys Lys Pro Val Arg Cys Ile Pro
        275                 280                 285

Gln Leu Asp Pro Phe Thr Thr Phe Gln Ala Trp Gln Leu Ala Thr Lys
    290                 295                 300

Gly Lys Val Ala Ile Cys Gln Glu Val Lys Glu Ser Gly Gln Glu Gly
305                 310                 315                 320

Ser Thr Asp Asn Asp Asp Ser Ser Ser Glu Lys Glu Leu Gly Glu Thr
                325                 330                 335
```

```
Asn Lys Gly Ser Cys Ala Gly Leu Ser Gln Glu Lys Glu Lys Cys Lys
            340                 345                 350

His Ser His Gly Glu Ala Pro Ser Val Asp Ala Asp Pro Lys Leu Pro
            355                 360                 365

Ser Ser Lys Glu Lys Pro Thr His Cys Ser Glu Cys Gly Lys Ala Phe
    370                 375                 380

Arg Thr Tyr His Gln Leu Val Leu His Ser Arg Val His Lys Lys Asp
385                 390                 395                 400

Arg Arg Ala Gly Ala Glu Ser Pro Thr Met Ser Val Asp Gly Arg Gln
                405                 410                 415

Pro Gly Thr Cys Ser Pro Asp Leu Ala Ala Pro Leu Asp Glu Asn Gly
            420                 425                 430

Ala Val Asp Arg Gly Glu Gly Ser Glu Asp Gly Ser Glu Asp Gly
            435                 440                 445

Leu Pro Glu Gly Ile His Leu Asp Lys Asn Asp Asp Gly Gly Lys Ile
    450                 455                 460

Lys His Leu Thr Ser Ser Arg Glu Cys Ser Tyr Cys Gly Lys Phe Phe
465                 470                 475                 480

Arg Ser Asn Tyr Tyr Leu Asn Ile His Leu Arg Thr His Thr Gly Glu
                485                 490                 495

Lys Pro Tyr Lys Cys Glu Phe Cys Tyr Ala Ala Ala Gln Lys Thr
    500                 505                 510

Ser Leu Arg Tyr His Leu Glu Arg His His Lys Glu Lys Gln Thr Asp
    515                 520                 525

Val Ala Ala Glu Val Lys Asn Asp Gly Lys Asn Gln Asp Thr Glu Asp
    530                 535                 540

Ala Leu Leu Thr Ala Asp Ser Ala Gln Thr Lys Asn Leu Lys Arg Phe
545                 550                 555                 560

Phe Asp Gly Ala Lys Asp Val Thr Gly Ser Pro Pro Ala Lys Gln Leu
            565                 570                 575

Lys Glu Met Pro Ser Val Phe Gln Asn Val Leu Gly Ser Ala Val Leu
            580                 585                 590

Ser Pro Ala His Lys Asp Thr Gln Asp Phe His Lys Asn Ala Ala Asp
            595                 600                 605

Asp Ser Ala Asp Lys Val Asn Lys Asn Pro Thr Pro Ala Tyr Leu Asp
            610                 615                 620

Leu Leu Lys Lys Arg Ser Ala Val Glu Thr Gln Ala Asn Asn Leu Ile
625                 630                 635                 640

Cys Arg Thr Lys Ala Asp Val Thr Pro Pro Asp Gly Ser Thr Thr
            645                 650                 655

His Asn Leu Glu Val Ser Pro Lys Glu Lys Gln Thr Glu Thr Ala Ala
            660                 665                 670

Asp Cys Arg Tyr Arg Pro Ser Val Asp Cys His Glu Lys Pro Leu Asn
    675                 680                 685

Leu Ser Val Gly Ala Leu His Asn Cys Pro Ala Ile Ser Leu Ser Lys
    690                 695                 700

Ser Leu Ile Pro Ser Ile Thr Cys Pro Phe Cys Thr Phe Lys Thr Phe
705                 710                 715                 720

Tyr Pro Glu Val Leu Met Met His Gln Arg Leu Glu His Lys Tyr Asn
            725                 730                 735

Pro Asp Val His Lys Asn Cys Arg Asn Lys Ser Leu Leu Arg Ser Arg
            740                 745                 750
```

```
Arg Thr Gly Cys Pro Pro Ala Leu Leu Gly Lys Asp Val Pro Pro Leu
            755                 760                 765

Ser Ser Phe Cys Lys Pro Lys Pro Lys Ser Ala Phe Pro Ala Gln Ser
770                 775                 780

Lys Ser Leu Pro Ser Ala Lys Gly Lys Gln Ser Pro Pro Gly Pro Gly
785                 790                 795                 800

Lys Ala Pro Leu Thr Ser Gly Ile Asp Ser Ser Thr Leu Ala Pro Ser
            805                 810                 815

Asn Leu Lys Ser His Arg Pro Gln Gln Asn Val Gly Val Gln Gly Ala
            820                 825                 830

Ala Thr Arg Gln Gln Gln Ser Glu Met Phe Pro Lys Thr Ser Val Ser
            835                 840                 845

Pro Ala Pro Asp Lys Thr Lys Arg Pro Glu Thr Lys Leu Lys Pro Leu
850                 855                 860

Pro Val Ala Pro Ser Gln Pro Thr Leu Gly Ser Ser Asn Ile Asn Gly
865                 870                 875                 880

Ser Ile Asp Tyr Pro Ala Lys Asn Asp Ser Pro Trp Ala Pro Pro Gly
            885                 890                 895

Arg Asp Tyr Phe Cys Asn Arg Ser Ala Ser Asn Thr Ala Ala Glu Phe
            900                 905                 910

Gly Glu Pro Leu Pro Lys Arg Leu Lys Ser Ser Val Val Ala Leu Asp
            915                 920                 925

Val Asp Gln Pro Gly Ala Asn Tyr Arg Arg Gly Tyr Asp Leu Pro Lys
            930                 935                 940

Tyr His Met Val Arg Gly Ile Thr Ser Leu Leu Pro Gln Asp Cys Val
945                 950                 955                 960

Tyr Pro Ser Gln Ala Leu Pro Pro Lys Pro Arg Phe Leu Ser Ser Ser
            965                 970                 975

Glu Val Asp Ser Pro Asn Val Leu Thr Val Gln Lys Pro Tyr Gly Gly
            980                 985                 990

Ser Gly Pro Leu Tyr Thr Cys Val Pro Ala Gly Ser Pro Ala Ser Ser
            995                 1000                1005

Ser Thr Leu Glu Gly Leu Gly Gly Cys Gln Cys Leu Leu Pro Met Lys
1010                1015                1020

Leu Asn Phe Thr Ser Ser Phe Glu Lys Arg Met Val Lys Ala Thr Glu
1025                1030                1035                1040

Ile Ser Cys Asp Cys Thr Val His Lys Thr Tyr Glu Glu Ser Ala Arg
            1045                1050                1055

Asn Thr Thr Val Val
            1060

(2) INFORMATION FOR SEQ ID NO:12:

(i) SEQUENCE CHARACTERISTICS:
        (A) LENGTH: 3066 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: -
        (B) LOCATION: 1..3066
        (D) OTHER INFORMATION: /note= "1b1"

(xi) SEQUENCE DESCRIPTION: SEQ ID NO:12:

GGAAACAGCT ATGACCATGA TTACGCCAAG CTCGAAATTA ACCCTCACTA AAGGGAACAA      60
```

```
AAGCTGGAGC TCCACCGCGG TGGCGGCCGC TCTAGAACTA GTGGATCCCC CGGGCTGCAG      120

GAATTCGGCA CGAGGCTCCA CCGACAGCCA GGCACTGGGC AGCACGCACT GGAGACCCAG      180

GACCCTGTGC AGGAGCAGCT CCGGGTGACA CGAGGGGACT GAAGATACTC CCACAGGGGC      240

TCAGCAGGAG CAATGGGTAA CCAAATGAGT GTTCCCCAAA GAGTTGAAGA CCAAGAGAAT      300

GAACCAGAAG CAGAGACTTA CCAGGACAAC GCGTCTGCTC TGAACGGGGT TCCAGTGGTG      360

GTGTCGACCC ACACAGTTCA GCACTTAGAG GAAGTCGACT TGGGAATAAG TGTCAAGACG      420

GATAATGTGG CCACTTCTTC CCCCGAGACA ACGGAGATAA GTGCTGTTGC GGATGCCAAC      480

GGAAAGAATC TTGGGAAAGA GGCCAAACCC GAGGCACCAG CTGCTAAATC TCGTTTTTTC      540

TTGATGCTCT CTCGGCCTGT ACCAGGACGT ACCGGAGACC AAGCCGCAGA TTCATCCCTT      600

GGATCAGTGA AGCTTGATGT CAGCTCCAAT AAAGCTCCAG CGAACAAAGA CCCAAGTGAG      660

AGCTGGACAC TTCCGGTGGC AGCTGGACCG GGGCAGGACA CAGATAAAAC CCCAGGGCAC      720

GCCCCGGCCC AAGACAAGGT CCTCTCTGCC GCCAGGGATC CCACGCTTCT CCCACCTGAG      780

ACAGGGGGAG CAGGAGGAGA AGCTCCCTCC AAGCCCAAGG ACTCCAGCTT TTTTGACAAA      840

TTCTTCAAGC TGGACAAGGG ACAGGAAAAG GTGCCAGGTG ACAGCCAACA GGAAGCCAAG      900

AGGGCAGAGC ATCAAGACAA GGTGGATGAG GTTCCTGGCT TATCAGGGCA GTCCGATGAT      960

GTCCCTGCAG GGAAGGACAT AGTTGACGGC AAGGAAAAAG AAGGACAAGA ACTTGGAACT     1020

GCGGATTGCT CTGTCCCTGG GGACCCAGAA GGACTGGAGA CTGCAAAGGA CGATTCCCAG     1080

GCAGCAGCTA TAGCAGAGAA TAATAATTCC ATCATGAGTT TCTTTAAAAC TCTGGTTTCA     1140

CCTAACAAAG CTGAAACAAA AAAGGACCCA GAAGACACGG GTGCTGAAAA GTCACCCACC     1200

ACTTCAGCTG ACCTTAAGTC AGACAAAGCC AACTTTACAT CCCAGGAGAC CAAGGGGCT      1260

GGCAAGAATT CCAAAGGATG CAACCCATCG GGGCACACAC AGTCCGTGAC AACCCCTGAA     1320

CCTGCGAAGG AAGGCACCAA GGAGAAATCA GGACCCACCT CTCTGCCTCT GGGCAAACTG     1380

TTTTGGAAAA AGTCAGTTAA AGAGGACTCA GTCCCCACAG GTGCGGAGGA GAATGTGGTG     1440

TGTGAGTCAC CAGTAGAGAT TATAAAGTCC AAGGAAGTAG AATCAGCCTT ACAAACAGTG     1500

GACCTCAACG AAGGAGATGC TGCACCTGAA CCCACAGAAG CGAAACTCAA AAGAGAAGAA     1560

AGCAAACCAA GAACCTCTCT GATGGCGTTT CTCAGACAAA TGTCAGTGAA AGGGGATGGA     1620

GGGATCACCC ACTCAGAAGA AATAAATGGG AAAGACTCCA GCTGCCAAAC ATCAGACTCC     1680

ACAGAAAGA CTATCACACC GCCAGAGCCT GAACCAACAG GAGCACCACA GAAGGGTAAA      1740

GAGGGCTCCT CGAAGGACAA GAAGTCAGCA GCCGAGATGA ACAAGCAGAA GAGCAACAAG     1800

CAGGAAGCCA AGAACCAGCC CCAGTGCACA GAGCAGGCCA CGGTGGACAC GAACTCACTG     1860

CAGAATGGGG ACAAGCTCCA AAAGAGACCT GAGAAGCGGC AGCAGTCCCT TGGGGGCTTC     1920

TTTAAAGGCC TGGGACCAAA GCGGATGTTG GATGCTCAAG TGCAAACAGA CCCAGTATCC     1980

ATCGGACCAG TTGGCAAACC CAAGTAAACA AATCAGCACG GTTCCCACCA GGTTCTCCTG     2040

CCACCAAGAT GTGTTCTCCT TACTCCATCT CCTCCCCAAA CACGCTCCAT GTATATATTC     2100

TTCTGATGGC CAGCAAATGA AATTCTGCCT AGAAATTAAG CCCGAGCTGT TGTATATTGA     2160

GGTGTATTAT TTACGTCTCT GGTCCAGTCT TTTCTGGCAA ATAACAGTAA AGATGGTTTA     2220

GCAGGTCACC TAGTTGGGTC AGAAGAGTCG ATGATCACCA AGCAGGAAAG GGAGGGAATA     2280

GAGGAATGTG TTCGGGTTAA GTGATGAAAA TGGCAGTGGT GGCCGGGCGT GGTGGCTCTC     2340

GCCTGTAATC TCAGCACTTT GGGAGGCCGA GGCAGGTGGA TCACCTGAGG TCAGGAGTTC     2400
```

| | |
|---|---|
| AAGACTAGCC TGGCCAACAT CATGAAACCC CGTCTCTACT AAAAATACAA AAATTAGCCA | 2460 |
| GGCATGGTGG CACACACCTG TAGTCCCAGC TACTCGGGAG CCCAACGCAC GAGAACCGCT | 2520 |
| TGTACCCAGG AGGTGGAGGT TGCAGTGAGC CGAAGTTGCA CCATTGCACT CCACCCTGGG | 2580 |
| CGACAGAGCA AGATTCTATC AAAAAAAAAA GGCAGTGGCA AGTAAGTTAT AGAAGAGAAA | 2640 |
| TGCTGCTAGA AGGAATTAAG CGTTGTAGTA AACGCGTGCT CATCCTCTAA GCTTGAAGAA | 2700 |
| GGGAGACGAA AATCCATTTG TTTAAATTCA CATCTCAAGG AGGGAGAACC CGGGCTGTGT | 2760 |
| TGGGTGGTTG CCAATTTCCT AGAACGGAAT GTGTGGGGTA TAGAAAAAGG AATGAATAAG | 2820 |
| CGTTGTTTTT CAAATAGGGT CCTTGTAAGT TATTGATGAG AGGGAAAAGA TTGACTGGGG | 2880 |
| AGGGCTTAAA ATGATTTGGG AAAACAATTG CTTTTGAGGC TCAGTGACAA CGGCAAAGAT | 2940 |
| TACAACTTAA AAAAAAAAAA AAAAAAACTC GAGACTAGTT CTCTCTCTCT CTCGTGCCGA | 3000 |
| ATTCGATATC AAGCTTATCG ATACCGTCGA CCTCGAGGGG GGGCCCGGTA CCCAATTCGC | 3060 |
| CCTATA | 3066 |

(2) INFORMATION FOR SEQ ID NO:13:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:13:

| | |
|---|---|
| TTGGCATTGG TATCAGGTAG CTG | 23 |

(2) INFORMATION FOR SEQ ID NO:14:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:14:

| | |
|---|---|
| TTGGAGCAGA GAGGGGATTG TGTG | 24 |

(2) INFORMATION FOR SEQ ID NO:15:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:15:

| | |
|---|---|
| AATCCCCTCA AACCCTGCTG CTAC | 24 |

(2) INFORMATION FOR SEQ ID NO:16:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:16:

TGGAGCCTGA ACTTCTGCAA TC                                            22

(2) INFORMATION FOR SEQ ID NO:17:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:17:

CCGGGATACC GACATTG                                                  17

(2) INFORMATION FOR SEQ ID NO:18:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:18:

TGCACATAAA ACAGCCAGC                                                19

(2) INFORMATION FOR SEQ ID NO:19:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:19:

TTGGAATCAA TGGAGCAAAA                                               20

(2) INFORMATION FOR SEQ ID NO:20:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:20:

AGCTTTACCC AATGTGGTCC                                               20

(2) INFORMATION FOR SEQ ID NO:21:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:21:

GTGGTGAACA CCAATAAATG G                                             21

(2) INFORMATION FOR SEQ ID NO:22:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:22:

AAGCAAATAA AACCAATAAA CTCG                                24

(2) INFORMATION FOR SEQ ID NO:23:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:23:

CAAGATCTGA CCCCGTCAAT C                                    21

(2) INFORMATION FOR SEQ ID NO:24:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:24:

GACTTCTTCA GGAAAGAGAT CAGTG                              25

(2) INFORMATION FOR SEQ ID NO:25:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:25:

GCCATGTACC CACCTGAAAA ATC                                23

(2) INFORMATION FOR SEQ ID NO:26:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:26:

TCAGAACACC CGTGCAGAAT TAAG                                24

(2) INFORMATION FOR SEQ ID NO:27:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:27:

CCTAAAACTT GGTGCTTAAA TCTA                                              24

(2) INFORMATION FOR SEQ ID NO:28:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:28:

GTCTCACAAG GCAGATGTGG                                                   20

(2) INFORMATION FOR SEQ ID NO:29:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:29:

TTTGTGTATG TTGAGCCATC                                                   20

(2) INFORMATION FOR SEQ ID NO:30:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:30:

CTTCCAATCT CATTCTATGA GG                                                22

(2) INFORMATION FOR SEQ ID NO:31:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:31:

GCTTGTTTAA GTGTCACTAG GG                                                22

(2) INFORMATION FOR SEQ ID NO:32:

(i) SEQUENCE CHARACTERISTICS:
        (A) LENGTH: 23 base pairs
        (B) TYPE: nucleic acid
        (C) STRANDEDNESS: single (D) TOPOLOGY: linear (ii) MOLECULE TYPE: DNA (xi) SEQUENCE DESCRIPTION: SEQ ID NO:32:

CACTCTGGTA AATGACCTTT GTC                                            23

(2) INFORMATION FOR SEQ ID NO:33:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:33:

CCTACACCAT TCCAACTTTG G                                              21

(2) INFORMATION FOR SEQ ID NO:34:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:34:

GCCAGATGTA TGTTTGCTAC GGAAC                                          25

(2) INFORMATION FOR SEQ ID NO:35:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:35:

TCTCAAACCT GTCCACTTCT TG                                             22

(2) INFORMATION FOR SEQ ID NO:36:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:36:

CTGCTGTGGT GGAGAATGG                                                 19

(2) INFORMATION FOR SEQ ID NO:37:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:37:

TGTCCTCCTT CTCCCTCATC CTAC                                    24

(2) INFORMATION FOR SEQ ID NO:38:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:38:

AATGCCTCCA CTCACAGGAA TG                                      22

(2) INFORMATION FOR SEQ ID NO:39:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:39:

CCTCTTCAGT GTCTTCCTAT TGA                                     23

(2) INFORMATION FOR SEQ ID NO:40:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:40:

GGGAGGAGGT TGTAGGCAAC                                         20

(2) INFORMATION FOR SEQ ID NO:41:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:41:

AGCAAAGCAA AGGTGGCACA C                                       21

(2) INFORMATION FOR SEQ ID NO:42:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:42:

TGACATGGGA GAAGACACAC TTCC                                    24

(2) INFORMATION FOR SEQ ID NO:43:

(i) SEQUENCE CHARACTERISTICS:
       (A) LENGTH: 20 base pairs
       (B) TYPE: nucleic acid
       (C) STRANDEDNESS: single
       (D) TOPOLOGY: linear (ii) MOLECULE TYPE: DNA (xi) SEQUENCE DESCRIPTION: SEQ ID NO:43:

```
AGGTTTACCA ATGTGTTTGG                                              20
```

(2) INFORMATION FOR SEQ ID NO:44:

(i) SEQUENCE CHARACTERISTICS:
       (A) LENGTH: 21 base pairs
       (B) TYPE: nucleic acid
       (C) STRANDEDNESS: single
       (D) TOPOLOGY: linear (ii) MOLECULE TYPE: DNA (xi) SEQUENCE DESCRIPTION: SEQ ID NO:44:

```
TCTACATCCC ATTCTCTTCT G                                            21
```

(2) INFORMATION FOR SEQ ID NO:45:

(i) SEQUENCE CHARACTERISTICS:
       (A) LENGTH: 939 base pairs
       (B) TYPE: nucleic acid
       (C) STRANDEDNESS: single
       (D) TOPOLOGY: linear (ii) MOLECULE TYPE: DNA (genomic)

(ix) FEATURE:
       (A) NAME/KEY: -
       (B) LOCATION: 1..939
       (D) OTHER INFORMATION: /note= "putative human cyclophilin gene
            from genomic clone (BAC clone 97) with
            homology to rat cyclophilin cDNA"

(xi) SEQUENCE DESCRIPTION: SEQ ID NO:45:

```
TGTGATATTG ATTCATGCCC TCTTGCACCT TGCCAAACAT CACACGCTTG CCATCCAGTC    60
CACTCGATTT TGGCAGTGCA GATGAAAAAC TGGGAACCAT TTGTGTTGAG TCCAGCAAGA   120
TGCCAGGACC TGCATGTTTC AGAACGAAGT TCTTCATCAT CCAATTTCTC CCTGTATATG   180
GGCTTACCAC NACTGCCGTT AAGTCGTGTN AAGTCACCAC TCAGGTACAT AATGGAATAA   240
TTCTGCAAAG GCAGGAGNCA CTTTCTCTCC AGTGCTCAGA CCATGAAAGT TTTCTGATGT   300
CTTTGGAACT TTGTCTGCAA ATAGCTCGAA GGAGACATGG CCTAAAGGCT CGCCATCTGC   360
GGTGATATTG NAACATGGTA GGGCTGACCG TGGCTGTGGC CATGACTTTT TAGANTNNNN   420
NNNNNNNNNN NNNNNNNNNN NNNNNNNNNN NNNNNNNNNN NNNNNNNNNN NNNNNNNNNN   480
NNNNNNNNNN NNNNNNNNNN NNNNNNNNNN NNNCCCAAT GCGGGACAGA GAATCNAAGA   540
AACTGTATTA GGGAAAGGGT CCTGAGTTTA TGCCAAAGTT TCCCAGATTG GTTTCCATTG   600
AAACGTAGCT CTGTGAGATA CCATCAGGTG TTATGTGAAG AAATGTCTGT GTAGTCAAAT   660
ATGTTTGAGT GAGTGAGCCT GAGCTGAGCA AGACTTTACT GCAAGACTTC CCATCTTCTG   720
TCCCTTTTTA TGCTAATGGG TAACACAAAC TCCAAAAGTG GGGTGTACAG CATGAGGCAT   780
TAACAAAAAT TTATTGGACC CCACACACNN NNNNNNNNNN NNNNNNNNNN NNNNNNNNNN   840
NNNNNNNNNN NNNNNNNNNN NNNNNNNNNN NNNNNNNNNN NNNNNNNNNN NNNNNNNNNN   900
```

NNNNNNNNNN NNNNNNNNNN NNNNNNNNNN NNNNCTCTC                                939

(2) INFORMATION FOR SEQ ID NO:46:

(i) SEQUENCE CHARACTERISTICS:
        (A) LENGTH: 112 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: -
        (B) LOCATION: 1..112
        (D) OTHER INFORMATION: /note= "positions 261-372 of putative
            human cyclophilin gene genomic clone
            (BAC clone 97) complementary strand with
            homology to positions 64-175 of rat
            cyclophilin gene cDNA"

(xi) SEQUENCE DESCRIPTION: SEQ ID NO:46:

GAAAGAGAGG TCACGAGTCT GGTACTTTCA AAAGACTACA GAAACCTTGA AACAGACGTT          60

TATCGAGCTT CCTCTGTACC GGATTTCCGA GCGGTAGACG CCACTATAAC NT                 112

(2) INFORMATION FOR SEQ ID NO:47:

(i) SEQUENCE CHARACTERISTICS:
        (A) LENGTH: 112 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: -
        (B) LOCATION: 1..112
        (D) OTHER INFORMATION: /note= "positions 64-175 of rat
            cyclophilin cDNA with homology to
            positions 261-372 of putative human
            cyclophilin gene genomic clone (BAC
            clone 97) complementary strand"

(xi) SEQUENCE DESCRIPTION: SEQ ID NO:47:

TTCGACATCA CGGCTGATGG CGAGCCCTTG GGTCGCGTCT GCTTCGAGCT GTTTGCAGAC          60

AAAGTTCCAA AGACAGCAGA AAACTTTCGT GCTCTGAGCA CTGGGGAGAA AG                 112

(2) INFORMATION FOR SEQ ID NO:48:

(i) SEQUENCE CHARACTERISTICS:
        (A) LENGTH: 58 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: -
        (B) LOCATION: 1..58
        (D) OTHER INFORMATION: /note= "positions 60-117 of putative
            human cyclophilin gene genomic clone
            (BAC clone 97) complementary strand
            with homology to positions 348-405 of
            rat cyclophilin gene cDNA"

(xi) SEQUENCE DESCRIPTION: SEQ ID NO:48:

GGTGAGCTAA AACCGTCACG TCTACTTTTT GACCCTTGGT AAACACAACT CAGGTCGT           58

(2) INFORMATION FOR SEQ ID NO:49:

(i) SEQUENCE CHARACTERISTICS:
        (A) LENGTH: 58 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: -
        (B) LOCATION: 1..58
        (D) OTHER INFORMATION: /note= "positions 348-405 of rat
            cyclophilin gene cDNA with homology to
            positions 60-117 of putative human
            cyclophilin gene genomic clone (BAC
            clone 97) complementary strand"

(xi) SEQUENCE DESCRIPTION: SEQ ID NO:49:

TGCTGGACCA AACACAAATG GTTCCCAGTT TTTTATCTGC ACTGCCAAGA CTGAGTGG        58

(2) INFORMATION FOR SEQ ID NO:50:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: -
        (B) LOCATION: 1..48
        (D) OTHER INFORMATION: /note= "positions 13-60 of putative
            human cyclophilin gene genomic clone
            (BAC clone 97) complementary strand with
            homology to positions 404-451 of rat
            cyclophilin gene cDNA"

(xi) SEQUENCE DESCRIPTION: SEQ ID NO:50:

AGTACGGGAG AACGTGGAAC GGTTTGTAGT GTGCGAACGG TAGGTCAG        48

(2) INFORMATION FOR SEQ ID NO:51:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: -
        (B) LOCATION: 1..48
        (D) OTHER INFORMATION: /note= "positions 404-451 of rat
            cyclophilin gene cDNA with homology to
            positions 13-60 of putative human
            cyclophilin gene genomic clone (BAC
            clone 97) complementary strand"

(xi) SEQUENCE DESCRIPTION: SEQ ID NO:51:

GGCTGGATGG CAAGCATGTG GTCTTTGGGA AGGTGAAAGA AGGCATGA        48

(2) INFORMATION FOR SEQ ID NO:52:

(i) SEQUENCE CHARACTERISTICS:
        (A) LENGTH: 38 base pairs
        (B) TYPE: nucleic acid
        (C) STRANDEDNESS: single

```
        (D) TOPOLOGY: linear (ii) MOLECULE TYPE: DNA (genomic)

(ix) FEATURE:
        (A) NAME/KEY: -
        (B) LOCATION: 1..38
        (D) OTHER INFORMATION: /note= "positions 116-153 of putative
            human cyclophilin gene genomic clone
            (BAC clone 97) complementary strand with
            homology to positions 299-336 of rat
            cyclophilin gene cDNA"

(xi) SEQUENCE DESCRIPTION: SEQ ID NO:52:

GTTCTACGGT CCTGGACGTA CAAAGTCTTG CTTCAAGA                                    38

(2) INFORMATION FOR SEQ ID NO:53:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: -
        (B) LOCATION: 1..38
        (D) OTHER INFORMATION: /note= "positions 299-336 of rat
            cyclophilin gene cDNA with homology to
            positions 116-153 of putative human
            cyclophilin gene genomic clone (BAC
            clone 97) complementary strand"

(xi) SEQUENCE DESCRIPTION: SEQ ID NO:53:

AGAACTTCAT CCTGAAGCAT ACAGGTCCTG GCATCTTG                                    38

(2) INFORMATION FOR SEQ ID NO:54:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: -
        (B) LOCATION: 1..28
        (D) OTHER INFORMATION: /note= "positions 229-256 of putative
            human cyclophilin gene genomic clone
            (BAC clone 97) complementary strand with
            homology to positions 193-220 of rat
            cyclophilin gene cDNA"

(xi) SEQUENCE DESCRIPTION: SEQ ID NO:54:

TATTACCTTA TTAAGACGTT TCCGTCCT                                               28

(2) INFORMATION FOR SEQ ID NO:55:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: -
        (B) LOCATION: 1..28
```

-continued

```
    (D) OTHER INFORMATION: /note= "positions 193-220 of rat
        cyclophilin gene cDNA with homology to
        positions 229-256 of putative human
        cyclophilin gene genomic clone (BAC
        clone 97) complementary strand"

(xi) SEQUENCE DESCRIPTION: SEQ ID NO:55:

TCCTCCTTTC ACAGAATTAT TCCAGGAT                                           28
```

US 8,993,251 B2

GENES FROM 20Q13 AMPLICON AND THEIR USES

CROSS-REFERENCE TO RELATED APPLICATIONS

This application is a continuation of U.S. Ser. No. 12/127,774, filed on May 27, 2008, now U.S. Pat. No. 8,101,370, which is a continuation of U.S. Ser. No. 08/785,532, filed on Jan. 17, 1997, now U.S. Pat. No. 7,455,964, which is a continuation-in-part of U.S. Ser. No. 08/731,499, filed on Oct. 16, 1996, now U.S. Pat. No. 7,049,424, and is a continuation-in-part of U.S. Ser. No. 08/680,395, filed on Jul. 15, 1996, now U.S. Pat. No. 5,892,010, which is related to U.S. Ser. No. 08/546,130, filed Oct. 20, 1995, now U.S. Pat. No. 5,801,021, each of which is incorporated herein by reference for all purposes.

BACKGROUND OF THE INVENTION

This invention pertains to the field of cytogenetics. More particularly this invention pertains to the identification of genes in a region of amplification at about 20q13 in various cancers. The genes disclosed here can be used as probes specific for the 20q13 amplicon as well as for treatment of various cancers.

Chromosome abnormalities are often associated with genetic disorders, degenerative diseases, and cancer. In particular, the deletion or multiplication of copies of whole chromosomes or chromosomal segments, and higher level amplifications of specific regions of the genome are common occurrences in cancer. See, for example Smith, et al., *Breast Cancer Res. Treat.*, 18: Suppl. 1: 5-14 (1991, van de Vijer & Nusse, *Biochim. Biophys. Acta.* 1072: 33-50 (1991), Sato, et al., *Cancer. Res.*, 50: 7184-7189 (1990). In fact, the amplification and deletion of DNA sequences containing proto-oncogenes and tumor-suppressor genes, respectively, are frequently characteristic of tumorigenesis. Dutrillaux, et al., *Cancer Genet. Cytogenet.*, 49: 203-217 (1990). Clearly, the identification of amplified and deleted regions and the cloning of the genes involved is crucial both to the study of tumorigenesis and to the development of cancer diagnostics.

The detection of amplified or deleted chromosomal regions has traditionally been done by cytogenetics. Because of the complex packing of DNA into the chromosomes, resolution of cytogenetic techniques has been limited to regions larger than about 10 Mb; approximately the width of a band in Giemsa-stained chromosomes. In complex karyotypes with multiple translocations and other genetic changes, traditional cytogenetic analysis is of little utility because karyotype information is lacking or cannot be interpreted. Teyssier, J. R., *Cancer Genet. Cytogenet.*, 37: 103 (1989). Furthermore, conventional cytogenetic banding analysis is time consuming, labor intensive, and frequently difficult or impossible.

More recently, cloned probes have been used to assess the amount of a given DNA sequence in a chromosome by Southern blotting. This method is effective even if the genome is heavily rearranged so as to eliminate useful karyotype information. However, Southern blotting only gives a rough estimate of the copy number of a DNA sequence, and does not give any information about the localization of that sequence within the chromosome.

Comparative genomic hybridization (CGH) is a more recent approach to identify the presence and localization of amplified/deleted sequences. See Kallioniemi, et al., *Science*, 258: 818 (1992). CGH, like Southern blotting, reveals amplifications and deletions irrespective of genome rearrangement. Additionally, CGH provides a more quantitative estimate of copy number than Souther blotting, and moreover also provides information of the localization of the amplified or deleted sequence in the normal chromosome.

Using CGH, the chromosomal 20q13 region has been identified as a region that is frequently amplified in cancers. Initial analysis of this region in breast cancer cell lines identified a region approximately 2 Mb on chromosome 20 that is consistently amplified.

SUMMARY OF THE INVENTION

The present invention relates to the identification of a narrow region (about 600 kb) within a 2 Mb amplicon located at about chromosome 20q13 (more precisely at 20q13.2) that is consistently amplified in primary tumors. In addition, this invention provides cDNA sequences from a number of genes which map to this region. These sequences are useful as probes or as probe targets for monitoring the relative copy number of corresponding sequences from a biological sample such as a tumor cell. Also provided is a contig (a series of clones that contiguously spans this amplicon) which can be used to prepare probes specific for the amplicon. The probes can be used to detect chromosomal abnormalities at 20q13.

Thus, in one embodiment, this invention provides a method of detecting a chromosome abnormality (e.g., an amplification or a deletion) at about position FLpter 0.825 on human chromosome 20 (20q13.2). The method involves contacting a chromosome sample from a patient with a composition consisting essentially of one or more labeled nucleic acid probes each of which binds selectively to a target polynucleotide sequence at about position FLpter 0.825 on human chromosome 20 under conditions in which the probe forms a stable hybridization complex with the target sequence; and detecting the hybridization complex. The step of detecting the hybridization complex can involve determining the copy number of the target sequence. The probe preferably comprises a nucleic acid that specifically hybridizes under stringent conditions to a nucleic acid selected from the nucleic acids disclosed here. Even more preferably, the probe comprises a subsequence selected from sequences set forth in SEQ ID NOs:1-10 and 12. The probe is preferably labeled, and is more preferably labeled with digoxigenin or biotin. In one embodiment, the hybridization complex is detected in interphase nuclei in the sample. Detection is preferably carried out by detecting a fluorescent label (e.g., FITC, fluorescein, or Texas Red). The method can further involve contacting the sample with a reference probe which binds selectively to a chromosome 20 centromere.

This invention also provides for two new genes, ZABC1 and 1b1, in the 20q13.2 region that are both amplified and overexpressed in a variety of cancers. ZABC1 is a putative zinc finger protein. Zinc finger proteins are found in a variety of transcription factors, and amplification or overexpression of transcription factors typically results in cellular mis-regulation. ZABC1 and 1b1 thus appear to play an important role in the etiology of a number of cancers.

This invention provides for a new human cyclophilin nucleic acid (SEQ ID NO:45). Cyclophilin nucleic acids have been implicated in a variety of cellular mprocesses, including signal transduction.

This invention also provides for proteins encoded by nucleic acid sequences in the 20q13 amplicon (SEQ ID NOs: 1-10, 12, and 45) and subsequences, more preferably subsequences of at least 10 amino acids, preferably of at least 20 amino acids and most preferably of at least 30 amino acids in length. Particularly preferred subsequences are epitopes specific to the 20q13 proteins, more preferably epitopes specific to the ZABC1 and 1b1 proteins. Such proteins include, but are not limited to isolated polypeptides comprising at least 20 amino acids from a polypeptide encoded by the nucleic acids of SEQ ID NOs:1-10, 12, 45 or from the polypeptide of SEQ ID NO:11 wherein the polypeptide, when presented as an immunogen, elicits the production of an antibody which specifically binds to a polypeptide selected from the group consisting of a polypeptide encoded by the nucleic acids of SEQ ID NOs:1-10, 12, and 45 or from the polypeptide of SEQ ID NO:11, where the polypeptide does not bind to antisera raised against a polypeptide selected from the group consisting of a polypeptide encoded by the nucleic acids of SEQ ID NOs:1-10, 12, and 45 or from the polypeptide of SEQ ID NO:11 which has been fully immunosorbed with a polypeptide selected from the group consisting of a polypeptide encoded by the nucleic acids of SEQ ID NOs:1-10, 12, and 45 or from the polypeptide of SEQ ID NO:11. In preferred embodiments, the polypeptides of the invention hybridize to antisera raised against a polypeptide encoded by those encoded by SEQ ID NOs:1-10, 12, and 45where the antisera has been immusorbed with the most structurally related previously known polypeptide. For example, a polypeptide of the invention binds to antisera raised against a polypeptide encoded by SEQ ID NOs.45, wherein the antisera has been immusorbed with a rat or mouse cyclophilin polypeptide (Rat cyclophilin nucleic acids are known; see, GenBank™ under accession No. M19533; Mouse cyclophilin nucleic acids are known; see, GenBank™ under accession No. 50620. cDNAs from the mouse and rat cyclophilin cDNAs are about 85% identical to SEQ ID NO:45).

In another embodiment, the method can involve detecting a polypeptide (protein) encoded by a nucleic acid (ORF) in the 20q13 amplicon. The method may include any of a number of well known protein detection methods including, but not limited to, the protein assays disclosed herein.

This invention also provides cDNA sequences from genes in the amplicon (SEQ ID NOs:1-10, 12, and 45). The nucleic acid sequences can be used in therapeutic applications according to known methods for modulating the expression of the endogenous gene or the activity of the gene product. Examples of therapeutic approaches include antisense inhibition of gene expression, gene therapy, monoclonal antibodies that specifically bind the gene products, and the like. The genes can also be used for recombinant expression of the gene products in vitro.

This invention also provides for proteins (e.g., SEQ ID NO:11) encoded by the cDNA sequences from genes in the amplicon (e.g., SEQ ID NOs:1-10, 12, and 45). Where the amplified nucleic acids include cDNA which are expressed, detection and/or quantification of the protein expression product can be used to identify the presence or absence or quantify the amplification level of the amplicon or of abnormal protein products produced by the amplicon.

The probes disclosed here can be used in kits for the detection of a chromosomal abnormality at about position FLpter 0.825 on human chromosome 20. The kits include a compartment which contains a labeled nucleic acid probe which binds selectively to a target polynucleotide sequence at about FLpter 0.825 on human chromosome 20. The probe preferably includes at least one nucleic acid that specifically hybridizes under stringent conditions to a nucleic acid selected from the nucleic acids disclosed here. Even more preferably, the probes comprise one or more nucleic acids selected from the nucleic acids disclosed here. In a preferred embodiment, the probes are labelled with digoxigenin or biotin. The kit may further include a reference probe specific to a sequence in the centromere of chromosome 20.

Definitions

A "chromosome sample" as used herein refers to a tissue or cell sample prepared for standard in situ hybridization methods described below. The sample is prepared such that individual chromosomes remain substantially intact and typically comprises metaphase spreads or interphase nuclei prepared according to standard techniques.

"Nucleic acid" refers to a deoxyribonucleotide or ribonucleotide polymer in either single- or double-stranded form, and unless otherwise limited, would encompass known analogs of natural nucleotides that can function in a similar manner as naturally occurring nucleotides.

An "isolated" polynucleotide is a polynucleotide which is substantially separated from other contaminants that naturally accompany it, e.g., protein, lipids, and other polynucleotide sequences. The term embraces polynucleotide sequences which have been removed or purified from their naturally-occurring environment or clone library, and include recombinant or cloned DNA isolates and chemically synthesized analogues or analogues biologically synthesized by heterologous systems.

"Subsequence" refers to a sequence of nucleic acids that comprise a part of a longer sequence of nucleic acids.

A "probe" or a "nucleic acid probe", as used herein, is defined to be a collection of one or more nucleic acid fragments whose hybridization to a target can be detected. The probe is labeled as described below so that its binding to the target can be detected. The probe is produced from a source of nucleic acids from one or more particular (preselected) portions of the genome, for example one or more clones, an isolated whole chromosome or chromosome fragment, or a collection of polymerase chain reaction (PCR) amplification products. The probes of the present invention are produced from nucleic acids found in the 20q13 amplicon as described herein. The probe may be processed in some manner, for example, by blocking or removal of repetitive nucleic acids or enrichment with unique nucleic acids. Thus the word "probe" may be used herein to refer not only to the detectable nucleic acids, but to the detectable nucleic acids in the form in which they are applied to the target, for example, with the blocking nucleic acids, etc. The blocking nucleic acid may also be referred to separately. What "probe" refers to specifically is clear from the context in which the word is used.

"Hybridizing" refers the binding of two single stranded nucleic acids via complementary base pairing.

"Bind(s) substantially" or "binds specifically" or "binds selectively" or "hybridizes specifically" refer to complementary hybridization between an oligonucleotide and a target sequence and embraces minor mismatches that can be accommodated by reducing the stringency of the hybridization media to achieve the desired detection of the target polynucleotide sequence. These terms also refer to the binding, duplexing, or hybridizing of a molecule only to a particular nucleotide sequence under stringent conditions when that sequence is present in a complex mixture (e.g., total cellular) DNA or RNA. The term "stringent conditions" refers to conditions under which a probe will hybridize to its target subsequence, but to no other sequences. Stringent conditions are sequence-dependent and will be different in different circumstances. "Stringent hybridization" and "Stringent hybridization wash conditions" in the context of nucleic acid hybridization experiments such as CGH, FISH, Southern and northern hybridizations are sequence dependent, and are different under different environmental parameters. An extensive guide to the hybridization of nucleic acids is found in Tijssen (1993) *Laboratory Techniques in Biochemistry and Molecular Biology—Hybridization with Nucleic Acid Probes* part I chapter 2 "overview of principles of hybridization and the strategy of nucleic acid probe assays", Elsevier, N.Y. Generally, highly stringent hybridization and wash conditions are selected to be about 5° C. lower than the thermal melting point ($T_m$) for the specific sequence at a defined ionic strength and ph. The $T_m$ is the temperature (under defined ionic strength and pH) at which 50% of the target sequence hybridizes to a perfectly matched probe. Very stringent conditions are selected to be equal to the $T_m$ for a particular probe.

An example of stringent hybridization conditions for hybridization of complementary nucleic acids which have more than 100 complementary residues on a filter in a Southern or northern blot is 50% formalin with 1 mg of heparin at 42° C., with the hybridization being carried out overnight. An example of stringent wash conditions is a 0.2×SSC wash at 65° C. for 15 minutes (see, Sambrook, supra for a description of SSC buffer). Often, the high stringency wash is preceded by a low stringency wash to remove background probe signal. An example medium stringency wash for a duplex of, e.g., about 100 nucleotides or more, is 1×SSC at 45° C. for 15 minutes. An example low stringency wash for a duplex of, e.g., more than 100 nucleotides, is 4×SSC at 40° C. for 15 minutes. In general, a signal to noise ratio of 2× (or higher) than that observed for an unrelated probe in the particular hybridization assay indicates detection of a specific hybridization.

One of skill will recognize that the precise sequence of the particular probes described herein can be modified to a certain degree to produce probes that are "substantially identical" to the disclosed probes, but retain the ability to bind substantially to the target sequences. Such modifications are specifically covered by reference to the individual probes herein. The term "substantial identity" of polynucleotide sequences means that a polynucleotide comprises a sequence that has at least 90% sequence identity, more preferably at least 95%, compared to a reference sequence using the methods described below using standard parameters.

Two nucleic acid sequences are said to be "identical" if the sequence of nucleotides in the two sequences is the same when aligned for maximum correspondence as described below. The term "complementary to" is used herein to mean that the complementary sequence is identical to all or a portion of a reference polynucleotide sequence. Nucleic acids which do not hybridize to complementary versions of each other under stringent conditions are still substantially identical if the polypeptides which they encode are substantially identical. This occurs, e.g., when a copy of a nucleic acid is created using the maximum codon degeneracy permitted by the genetic code.

Sequence comparisons between two (or more) polynucleotides are typically performed by comparing sequences of the two sequences over a "comparison window" to identify and compare local regions of sequence similarity. A "comparison window", as used herein, refers to a segment of at least about 20 contiguous positions, usually about 50 to about 200, more usually about 100 to about 150 in which a sequence may be compared to a reference sequence of the same number of contiguous positions after the two sequences are optimally aligned.

Optimal alignment of sequences for comparison may be conducted by the local homology algorithm of Smith and Waterman *Adv. Appl. Math.* 2: 482 (1981), by the homology alignment algorithm of Needleman and Wunsch *J. Mol. Biol.* 48:443 (1970), by the search for similarity method of Pearson and Lipman *Proc. Natl. Acad. Sci.* (*U.S.A.*) 85: 2444 (1988), by computerized implementations of these algorithms.

"Percentage of sequence identity" is determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity. Another indication that nucleotide sequences are substantially identical is if two molecules hybridize to the same nucleic acid sequence under stringent conditions.

"Conservatively modified variations" of a particular nucleic acid sequence refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given polypeptide. For instance, the codons CGU, CGC, CGA, CGG, AGA, and AGG all encode the amino acid arginine. Thus, at every position where an arginine is specified by a codon, the codon can be altered to any of the corresponding codons described without altering the encoded polypeptide. Such nucleic acid variations are "silent variations," which are one species of "conservatively modified variations." Every nucleic acid sequence herein which encodes a polypeptide also describes every possible silent variation. One of skill will recognize that each codon in a nucleic acid (except AUG, which is ordinarily the only codon for methionine) can be modified to yield a functionally identical molecule by standard techniques. Accordingly, each "silent variation" of a nucleic acid which encodes a polypeptide is implicit in each described sequence. Furthermore, one of skill will recognize that individual substitutions, deletions or additions which alter, add or delete a single amino acid or a small percentage of amino acids (typically less than 5%, more typically less than 1%) in an encoded sequence are "conservatively modified variations" where the alterations result in the substitution of an amino acid with a chemically similar amino acid. Conservative substitution tables providing functionally similar amino acids are well known in the art. The following six groups each contain amino acids that are conservative substitutions for one another:

1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

The term "20q13 amplicon protein" is used herein to refer to proteins encoded ORFs in the 20q13 amplicon disclosed herein. Assays that detect 20q13 amplicon proteins are intended to detect the level of endogenous (native) 20q13 amplicon proteins present in subject biological sample. However, exogenous 20q13 amplicon proteins (from a source extrinsic to the biological sample) may be added to various assays to provide a label or to compete with the native 20q13 amplicon protein in binding to an anti-20q13 amplicon protein antibody. One of skill will appreciate that a 20q13 amplicon protein mimetic may be used in place of exogenous 20q13 protein in this context. A "20q13 protein", as used herein, refers to a molecule that bears one or more 20q13 amplicon protein epitopes such that it is specifically bound by an antibody that specifically binds a native 20q13 amplicon protein.

As used herein, an "antibody" refers to a protein consisting of one or more polypeptides substantially encoded by immunoglobulin genes or fragments of immunoglobulin genes. The recognized immunoglobulin genes include the kappa, lambda, alpha, gamma, delta, epsilon and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

The basic immunoglobulin (antibody) structural unit is known to comprise a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

Antibodies may exist as intact immunoglobulins or as a number of well characterized fragments produced by digestion with various peptidases. Thus, for example, pepsin digests an antibody below the disulfide linkages in the hinge region to produce F(ab)'$_2$, a dimer of Fab which itself is a light chain joined to $V_H$—$C_H$1 by a disulfide bond. The F(ab)'$_2$ may be reduced under mild conditions to break the disulfide linkage in the hinge region thereby converting the F(ab)'$_2$ dimer into an Fab' monomer. The Fab' monomer is essentially an Fab with part of the hinge region (see, *Fundamental Immunology*, W. E. Paul, ed., Raven Press, N.Y. (1993) for a more detailed description of other antibody fragments). While various antibody fragments are defined in terms of the digestion of an intact antibody, one of skill will appreciate that such Fab' fragments may be synthesized de novo either chemically or by utilizing recombinant DNA methodology. Thus, the term antibody, as used herein also includes antibody fragments either produced by the modification of whole antibodies or synthesized de novo using recombinant DNA methodologies.

The phrase "specifically binds to a protein" or "specifically immunoreactive with", when referring to an antibody refers to a binding reaction which is determinative of the presence of the protein in the presence of a heterogeneous population of proteins and other biologics. Thus, under designated immunoassay conditions, the specified antibodies bind to a particular protein and do not bind in a significant amount to other proteins present in the sample. Specific binding to a protein under such conditions may require an antibody that is selected for its specificity for a particular protein. For example, antibodies can be raised to the a 20q13 amplicon protein that bind the 20q13 amplicon protein and not to any other proteins present in a biological sample. A variety of immunoassay formats may be used to select antibodies specifically immunoreactive with a particular protein. For example, solid-phase ELISA immunoassays are routinely used to select monoclonal antibodies specifically immunoreactive with a protein. See Harlow and Lane (1988) *Antibodies, A Laboratory Manual*, Cold Spring Harbor Publications, New York, for a description of immunoassay formats and conditions that can be used to determine specific immunoreactivity.

DETAILED DESCRIPTION

This invention provides a number of cDNA sequences which can be used as probes for the detection of chromosomal abnormalities at 20q13. Studies using comparative genomic hybridization (CGH) have shown that a region at chromosome 20q13 is increased in copy number frequently in cancers of the breast (~30%), ovary (~15%), bladder (~30%), head and neck (~75%) and colon (~80%). This suggests the presence of one or more genes that contribute to the progression of several solid tumors are located at 20q13.

Gene amplification is one mechanism by which dominantly acting oncogenes are overexpressed, allowing tumors to acquire novel growth characteristics and/or resistance to chemotherapeutic agents. Loci implicated in human breast cancer progression and amplified in 10-25% of primary breast carcinomas include the erbB-2 locus (Lupu et al., *Breast Cancer Res. Treat.*, 27: 83 (1993), Slamon et al. *Science*, 235: 177-182 (1987), Heiskanen et al. *Biotechniques*, 17: 928 (1994)) at 17q12, cyclin-D (Mahadevan et al., *Science*, 255: 1253-1255 (1993), Gillett et al., *Canc. Res.*, 54: 1812 (1994)) at 11q13 and MYC (Gaffey et al., *Mod. Pathol.*, 6: 654 (1993)) at 8q34.

Pangenomic surveys using comparative genomic hybridization (CGH) recently identified about 20 novel regions of increased copy number in breast cancer (Kallioniemi et al., *Genomics*, 20: 125-128 (1994)). One of these loci, band 20q13, was amplified in 18% of primary tumors and 40% of cell lines (Kallioniemi et al., *Genomics*, 20: 125-128 (1994)). More recently, this same region was found amplified in 15% of ovarian, 80% of bladder and 80% of colorectal tumors. The resolution of CGH is limited to 5-10 Mb. Thus, FISH was performed using locus specific probes to confirm the CGH data and precisely map the region of amplification.

The 20q13 region has been analyzed in breast cancer at the molecular level and a region, approximately 600 kb wide, that is consistently amplified was identified, as described herein. Moreover, as shown herein, the importance of this amplification in breast cancer is indicated by the strong association between amplification and decreased patient survival and increased tumor proliferation (specifically, increased fraction of cells in S-phase).

Figure 1A:
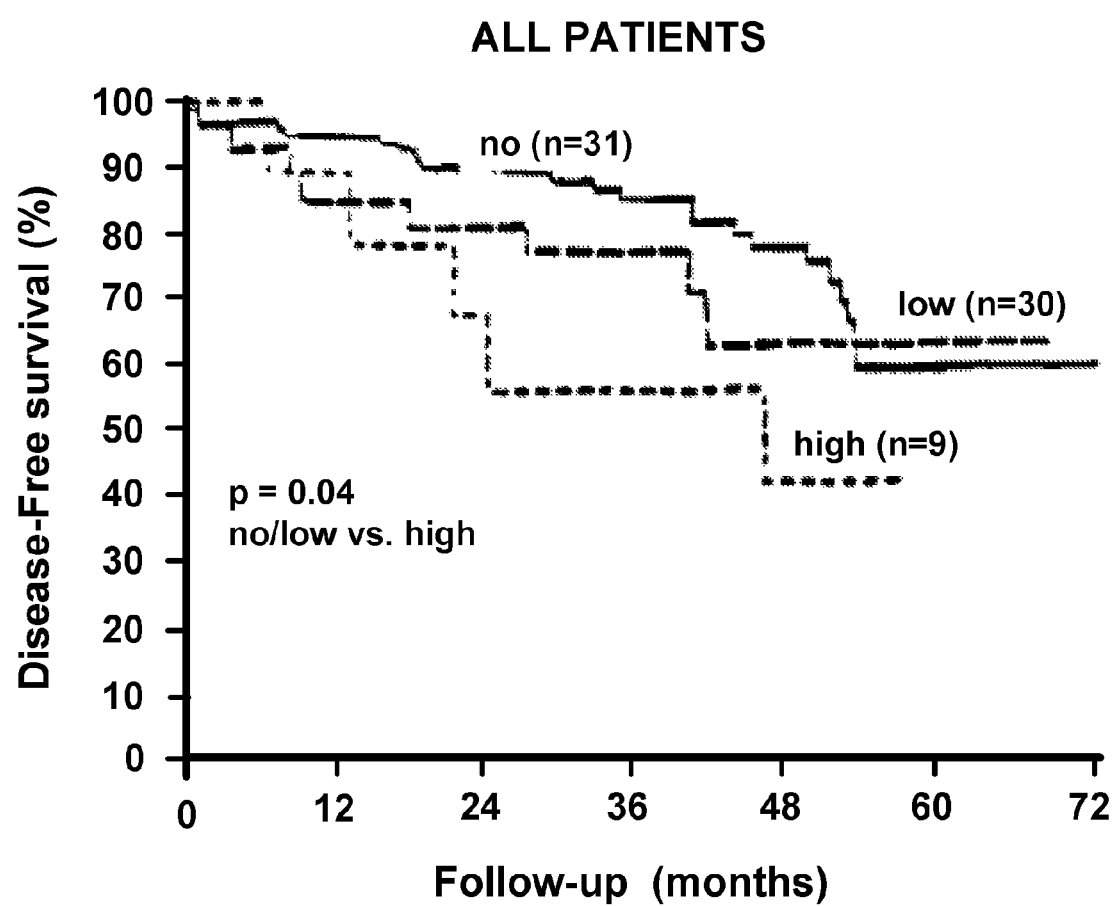
FIG. 1(A) shows disease-free survival of 129 breast cancer patients according to the level of 20q13 amplification. Patients with tumors having high level 20q13 amplification have a shorter disease-free survival (p=0.04 by Mantel-Cox test) compared to those having no or low level amplification.
Figure 1B:
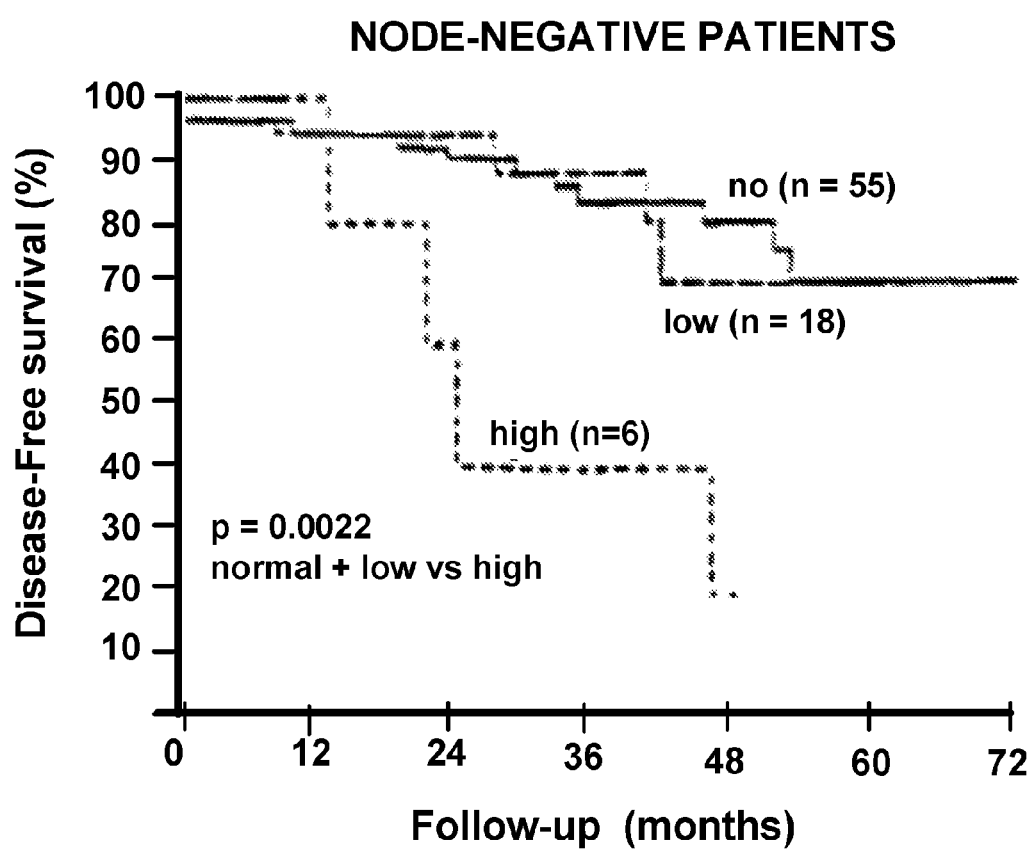
FIG. 1(B) Shows the disease-free survival difference in the sub-group of 79 axillary node-negative patients (p=0.0022 by Mantel-Cox test).
Figure 2:
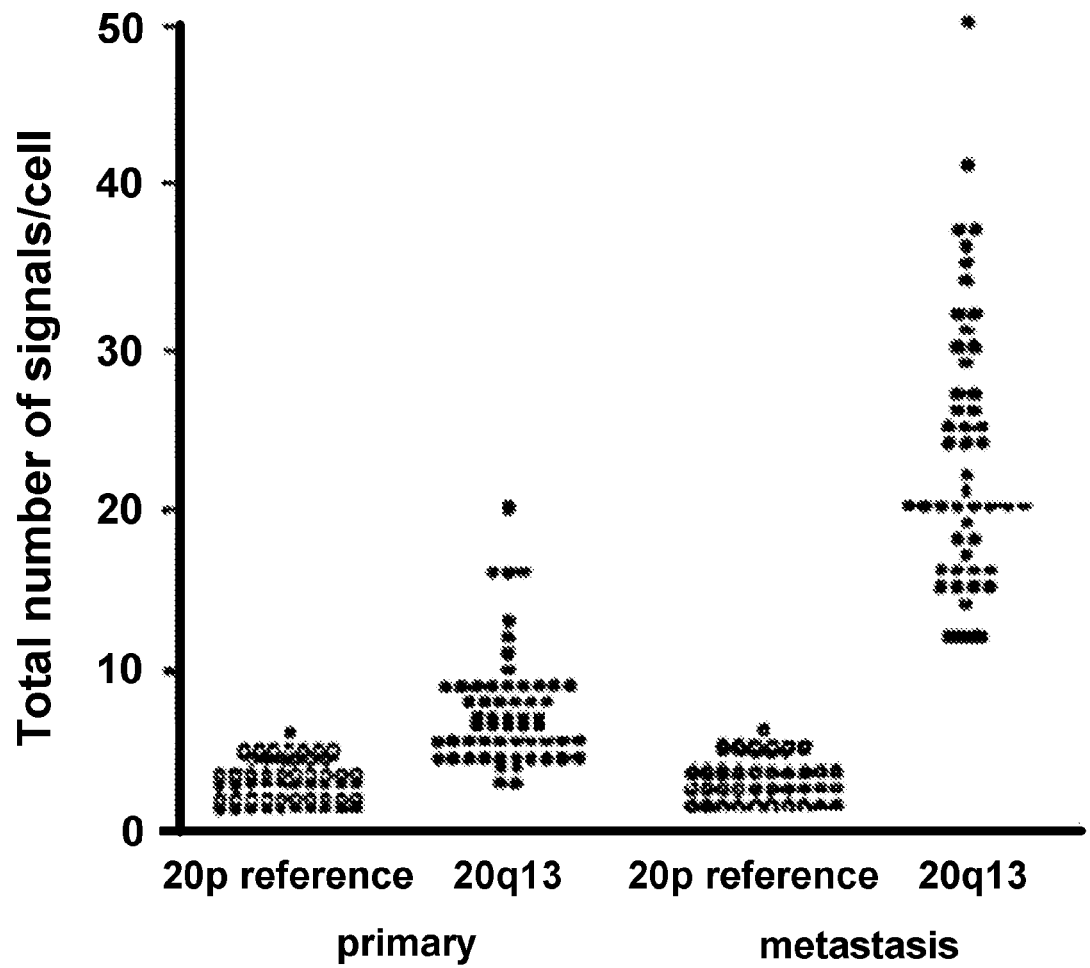
FIG. 2 shows a comparison of 20q13 amplification detected by FISH in a primary breast carcinoma and its metastasis from a 29-year patient. A low level amplification of 20q13 (20q13 compared to 20p reference probe) was found in the primary tumor. The metastasis, which appeared 8 months after mastectomy, shows a high level amplification of the chromosome 20q13 region. The overall copy number of chromosome 20 (20p reference probe) remained unchanged. Each data point represents gene copy numbers in individual tumor cells analyzed.

In particular, as explained in detail in Example 1, high-level 20q13 amplification was associated (p=0.0022) with poor disease free survival in node-negative patients, compared to cases with no or low-level amplification (FIG. 1).

Survival of patients with moderately amplified tumors did not differ significantly from those without amplification. Without being bound to a particular theory, it is suggested that an explanation for this observation may be that low level amplification precedes high level amplification. In this regard, it may be significant that one patient developed a local metastasis with high-level 20q13.2 amplification 8 month after resection of a primary tumor with low level amplification.

The 20q13 amplification was associated with high histologic grade of the tumors. This correlation was seen in both moderately and highly amplified tumors. There was also a correlation (p=0.0085) between high level amplification of a region complementary to a particular probe, RMC20C001 (Tanner et al., *Cancer Res.*, 54: 4257-4260 (1994)), and cell proliferation, measured by the fraction of cells in S-phase. This finding is important because it identifies a phenotype that can be scored in functional assays, without knowing the mechanism underlying the increased S-phase fraction. The 20q13 amplification did not correlate with the age of the patient, primary tumor size, axillary nodal or steroid hormone-receptor status.

This work localized the 20q13.2 amplicon to an interval of approximately 2 Mb. Furthermore, it suggests that high-level amplification, found in 7% of the tumors, confers an aggressive phenotype on the tumor, adversely affecting clinical outcome. Low level amplification (22% of primary tumors) was associated with pathological features typical of aggressive tumors (high histologic grade, aneuploidy and cell proliferation) but not patient prognosis.

In addition, it is shown herein that the 20q13 amplicon (more precisely the 20q13.2 amplicon) is one of three separate co-amplified loci on human chromosome 20 that are packaged together throughout the genomes of some primary tumors and breast cancer cell lines. No known oncogenes map in the 20q13.2 amplicon.

Identification of 20q13 Amplicon Probes

Initially, a paucity of available molecular cytogenetic probes dictated that FISH probes be generated by the random selection of cosmids from a chromosome 20 specific library, LA20NC01, and map them to chromosome 20 by digital imaging microscopy. Approximately 46 cosmids, spanning the 70 Mb chromosome, were isolated for which fractional length measurements (FLpter) and band assignments were obtained. Twenty six of the cosmids were used to assay copy number in the breast cancer cell line BT474 by interphase FISH analysis. Copy number was determined by counting hybridization signals in interphase nuclei. This analysis revealed that cosmid RMC20C001 (Flpter, 0.824; 20q13.2), described by Stokke et al., *Genomics*, 26: 134-137 (1995), defined the highest-level amplification (~60 copies/cell) in BT474 cells (Tanner et al., *Cancer Res.*, 54: 4257-4260 (1994)).

P1 clones containing genetically mapped sequences were selected from 20q13.2 and used as FISH probes to confirm and further define the region of amplification. Other P1 clones were selected for candidate oncogenes broadly localized to the 20q13.2 region (Flpter, 0.81-0.84). These were selected from the DuPont P1 library (Shepherd, et al., *Proc. Natl. Acad. Sci. USA*, 92: 2629 (1994), available commercially from Genome Systems), by PCR (Saiki et al, *Science*, 230: 1350 (1985)) using primer pairs developed in the 3' untranslated region of each candidate gene. Gene specific P1 clones were obtained for, protein tyrosine phosphatase (PTPN1, Flpter 0.78), melanocortin 3 receptor (MC3R, Flpter 0.81), phosphoenolpyruvate carboxy kinase (PCK1, Flpter 0.85), zinc finger protein 8 (ZNF8, Flpter 0.93), guanine nucleotide-binding protein (GNAS 1, Flpter 0.873), src-oncogene (SRC, Flpter 0.669), topoisomerase 1 (TOP1, Flpter 0.675), the bcl-2 related gene bcl-x (Flpter 0.526) and the transcription factor E2F-1 (FLpter 0.541). Each clone was mapped by digital imaging microscopy and assigned Flpter values. Five of these genes (SRC, TOPO1, GNAS1, E2F-1 and BC1-x) were excluded as candidate oncogenes in the amplicon because they mapped well outside the critical region at Flpter 0.81-0.84. Three genes (PTPNR1, PCK-1 and MC3R) localized close enough to the critical region to warrant further investigation.

Interphase FISH on 14 breast cancer cell lines and 36 primary tumors using 24 cosmid and 3 gene specific P1 (PTPNRL, PCK-1 and MC3R) probes found high level amplification in 35% (5/14) of breast cancer cell lines and 8% (3/36) of primary tumors with one or more probe. The region with the highest copy number in 4/5 of the cell lines and 3/3 primary tumors was defined by the cosmid RMC20C001. This indicated that PTPNR1, PCK1 and MC3R could also be excluded as candidates for oncogenes in the amplicon and, moreover, narrowed the critical region from 10 Mb to 1.5-2.0 Mb (see, Tanner et al., *Cancer Res.*, 54: 4257-4260 (1994).

Because probe RMC20C001 detected high-level (3 to 10-fold) 20q13.2 amplification in 35% of cell lines and 8% of primary tumors it was used to (1) define the prevalence of amplification in an expanded tumor population, (2) assess the frequency and level of amplification in these tumors, (3) evaluate the association of the 20q13.2 amplicon with pathological and biological features, (4) determine if a relationship exists between 20q13 amplification and clinical outcome and (5) assess 20q13 amplification in metastatic breast tumors.

As detailed in Example 1, fluorescent in situ hybridization (FISH) with RMC20C001 was used to assess 20q13.2 amplification in 132 primary and 11 recurrent breast tumors. The absolute copy number (mean number of hybridization signals per cell) and the level of amplification (mean number of signals relative to the p-arm reference probe) were determined. Two types of amplification were found: Low level amplification (1.5-3 fold with FISH signals dispersed throughout the tumor nuclei) and high level amplification (>3 fold with tightly clustered FISH signals). Low level 20q13.2 amplification was found in 29 of the 132 primary tumors (22%), whereas nine cases (6.8%) showed high level amplification.

RMC20C001 and four flanking P1 probes (MC3R, PCK, RMC20C026, and RMC20C030) were used to study the extent of DNA amplification in highly amplified tumors. Only RMC20C001 was consistently amplified in all tumors. This finding confirmed that the region of common amplification is within a 2 Mb interval flanked by but not including PCK-1 and MC3R.

A physical map was assembled to further localize the minimum common region of amplification and to isolate the postulated oncogene(s). The DuPont P1 library (Shepherd et al. *Proc. Natl. Acad. Sci. USA*, 91: 2629 (1994) was screened for STSs likely to map in band 20q 13.2. P1 clones at the loci D20S102, D20S100, D20S120, D20S183, D20S480, D20S211 were isolated, and FISH localized each to 20q13.2. Interphase FISH analysis was then performed in the breast cancer cell line BT474 to assess the amplification level at each locus. The loci D20S100-D20S120-D20S183-D20S480-D20S211 were highly amplified in the BT474 cell line, whereas D20S102 detected only low level amplification. Therefore, 5 STSs, spanning 5 cM, were localized within the 20q13.2 amplicon and were utilized to screen the CEPH megaYAC library.

CEPH megaYAC library screening and computer searches of public databases revealed D20S120-D20S183-D20S480-D20S211 to be linked on each of three megaYAC clones y820f5, 773h10, and 931h6. Moreover, screening the CEPH megaYAC library with STSs generated from the ends of cosmids RMC20C001, RMC20C30 and RMC20C028 localized RMC20C001 to each of the same three YAC clones. It was estimated, based on the size of the smallest of these YAC clones, that D20S120-D20S 183-RMC20C001-D20S480-D20S211 map into an interval of less than 1.1 Mb. D20S100 was localized 300 kb distal to D20S120 by interphase FISH and to YAC901b12 by STS mapping. The combined STS data made it possible to construct a 12 member YAC contig which spans roughly 4 Mb encompassing the 1.5 Mb amplicon and containing the loci RMC20C030-PCK1-RMC20C001-MC3R-RMC20 O26. Each YAC was mapped by FISH to confirm localization to 20q13.2 and to check for chimerism. Five clonal isolates of each YAC were sized by pulsed field gel electrophoresis (PFGE). None of the YACs are chimeric, however, several are highly unstable.

The YAC contig served as a framework from which to construct a 2 Mb P1 contig spanning the 20Q13 amplicon. P1 clones offered numerous advantages over YAC clones including (1) stability, (2) a chimeric frequency of less than 1%, (3) DNA isolation by standard miniprep procedures, (4) they make ideal FISH probes, (5) the ends can be sequenced directly, (6) engineered γδ transposons carrying bidirectional primer binding sites can be integrated at any position in the cloned DNA (Strathmann et al., *Proc. Natl. Acad. Sci. USA*, 88: 1247 (1991)) (7) P1 clones are the templates for sequencing the human and Drosophila genomes at the LBNL HGC (Palazzolo et al. *DOE Human Genome Program, Contractor-Grantee Workshop IV. Santa Fe, N.M.*, Nov. 13-17, 1994).

About 90 P1 clones were isolated by screening the DuPont P1 library either by PCR or filter hybridization. For PCR based screening, more than 22 novel STSs were created by two methods. In the first method, the ends of P1 clones localized to the amplicon were sequenced, STSs developed, and the P1 library screened for walking clones. In the second approach inter-Alu PCR (Nelson et al., 86: 6686-6690 (1989)) was performed on YACs spanning the amplicon and the products cloned and sequenced for STS creation. In the filter based hybridization scheme P1 clones were obtained by performing inter-Alu PCR on YACs spanning the amplicon, radio-labeling the products and hybridizing these against filters containing a gridded array of the P1 library. Finally, to close gaps a human genomic bacterial artificial chromosome (BAC) library (Shizuya et al. *Proc. Natl. Acad. Sci. USA*, 89: 8794 (1992), commercially available from Research Genetics, Huntsville, Ala., USA) was screened by PCR. These methods combined to produce more than 100 P1 and BAC clones were localized to 20q13.2 by FISH. STS content mapping, fingerprinting, and free-chromatin fish (Heiskanen et al., *BioTechniques*, 17: 928 (1994)) were used to construct the 2 Mb contig.

Fine Mapping the 20q13.2 Amplicon in BT474

Clones from the 2 Mb P1 contig were used with FISH to map the level of amplification at 20q13.2 in the breast cancer cell line BT474. 35 P1 probes distributed at regular intervals along the contig were used. The resulting data indicated that the region of highest copy number increase in BT474 occurs between D20S100 and D20S211, an interval of approximately 1.5 Mb. P1 FISH probes, in this interval, detect an average of 50 signals per interphase nuclei in BT474, while no, or only low level amplification, was detected with the P1 clones outside this region. Thus, both the proximal and distal boundaries of the amplicon were cloned.

Fine Mapping the 20q13.2 Amplicon in Primary Tumors

Fine mapping the amplicon in primary tumors revealed the minimum common region of high amplification that is of pathobiological significance. This process is analogous to screening for informative meiosis in the narrowing of genetic intervals encoding heritable disease genes. Analysis of 132 primary tumors revealed thirty-eight primary tumors that are amplified at the RMC20C001 locus. Nine of these tumors have high level amplification at the RMC20C001 locus and were further analyzed by interphase FISH with 8 P1s that span the ≈2 Mb contig. The minimum common region of amplification was mapped to a ≈600 kb interval flanked by P1 clones #3 and #12 with the highest level of amplification detected by P1 clone #38 corresponding to RMC20C001.

The P1 and BAC clones spanning the 600 kb interval of the 20q13 amplicon are listed in Table 1 which provides a cross-reference to the DuPont P1 library described by Shepherd, et al., *Proc. Natl. Acad. Sci. USA*, 92: 2629 (1994). These P1

TABLE 1

Cross reference to probes of the DuPont P1 library (Shepherd, et al., Proc. Natl. Acad. Sci. USA, 92:2629 (1994) which is commercially available from Genomic Systems, St. Louis, Missouri, USA). PCR primers are illustrated for amplification of Sequence tag sites for each clone. In addition, PCR conditions (Mg concentration and annealing temperature), as well as PCR product size, is provided.

| PRIMER NAME | SIZE (bp) | mM MgCl | Ann. | P1 | PC | SCA | SEQ-forward | SEQ-backward | SEQ ID NO:- forward | SEQ ID NO:- backward |
|---|---|---|---|---|---|---|---|---|---|---|
| 352.32 | 136 | 1.5 | 52 | 20 | 103-e5 | 1228e | TTGGCATTGGTAT CAGGTAGCTG | TTGGAGCAGAGA GGGGATTGTGTG | 13 | 14 |
| 388.13 F1/B1 | 201 | 1.5 | 52 | 17 | 69g6 | 821 | AATCCCCCTCAAA CCCTGCTGCTAC | TGGAGCCTGAAC TTCTGCAATC | 15 | 16 |
|  |  |  |  | 19 | 98F4 | 1167f | " | " | " | " |
| D20S183 | 270 | 3 | 48 | 30 |  | 124g6 | CCGGGATACCGAC ATTG | TGCACATAAAAC AGCCAGC | 17 | 18 |
|  |  |  |  | 40 | 24h1 | 276h | " | " | " | " |
| D20S211 1/2 | 135 | 1.5 | 52 | 29 | 119f4 | 1418f | TTGGAATCAATGG AGCAAAA | AGCTTTACCCAA TGTGGTCC | 19 | 20 |
| D20S480 | 300 | 3 | 55 | 68 | 100d12 | 1199d2 | GTGGTGAACACCA ATAAATGG | AAGCAAATAAAA CCAATAAACTCG | 21 | 22 |
|  |  |  |  | 41 | 86c1 | 1020c | " | " | " | " |
|  |  |  |  | 42 | 103d9 | 1232d | " | " | " | " |
|  |  |  |  | 67 | 91b2 | 1081b9 | " | " | " | " |

TABLE 1 -continued

Cross reference to probes of the DuPont P1 library (Shepherd, et al., *Proc. Natl. Acad. Sci. USA*, 92:2629 (1994) which is commercially available from Genomic Systems, St. Louis, Missouri, USA). PCR primers are illustrated for amplification of Sequence tag sites for each clone. In addition, PCR conditions (Mg concentration and annealing temperature), as well as PCR product size, is provided.

| PRIMER NAME | SIZE (bp) | mM MgCl | Ann. | P1 | PC | SCA | SEQ-forward | SEQ-backward | SEQ ID NO:- forward | SEQ ID NO:- backward |
|---|---|---|---|---|---|---|---|---|---|---|
| 9X-SP6 hmF/hmB | 165 | 1.5 | 55 | 7 | 31d11 | 370d | CAAGATCTGACCC GTCAATC | GACTTCTTCAGGA AAGAGATCAGTG | 23 | 24 |
|  |  |  |  | 9 | 3519 | 416f | " | " | " | " |
| 11S-17 F2/B4 | 146 | 3 | 58 | 11 | 41b1 | 480b | GCCATGTACCCAC CTGAAAAATC | TCAGAACACCCG TGCAGAATTAAG | 25 | 26 |
| 12T-T7 F2/B1 | 153 | 3 | 58 | 12 | 42c2 | 493c | CCTAAAACTTGGT GCTTAAATCTA | GTCTCACAAGGC AGATGTGG | 27 | 28 |
| 28T F1/B1 | 219 | 1.5 | 52 | 74 |  | 888f2 | TTTGTGTATGTTG AGCCATC | CTTCCAATCTCA TTCTATGAGG | 29 | 30 |
|  |  |  |  | 2 | 12c6 | 137c | " | " | " | " |
|  |  |  |  | 25 | 118c11 | 1413c | " | " | " | " |
|  |  |  |  | 26 | 118c11 | 1413c | " | " | " | " |
| 28S F1/B3 | 214 | 1.5 | 55 | 28 | 118g11 | 1413g | GCTTGTTTAAGTG TCACTAGGG | CACTCTGGTAAA TGACCTTTGTC | 31 | 32 |
|  |  |  |  | 25 | 118c11 | 1413c | " | " | " | " |
|  |  |  |  | 27 | 118g11 | 1413g | " | " | " | " |
|  |  |  |  | 10 | 36f10 | 429f | " | " | " | " |
| 69S | 100 | 3 | 55 | 69 |  | 412b5 | CCTACACCTTCCA ACTTTGG | GCCAGATGTATGT TTGCTACGGAAC | 33 | 34 |
|  |  |  |  | 5 | 23c1 | 264c | " | " | " | " |
| HSCOFH032 F/B | 129 | 1.5 | 55 | 3 | 12-e11 | 142e | TCTCAAACCTGTC CACTTCTTG | CTGCTGTGGTGG AGAATGG | 35 | 36 |
|  |  |  |  | 18 | 77a10 | 921a | " | " | " | " |
| 60A1 | 191 | 1.5 | 58 | 36 | 112g8 | 1139g | TGTCCTCCTTCTC CCTCATCCTAC | AATGCCTCCACT CACAGGAATG | 37 | 38 |
|  |  |  |  | 39 | 34a6 | 401a | " | " | " | " |
| 820F5A1T F1/B1 | 175 | 1.5 | 48 | 15 | 53c7 | 630c | CCTCTTCAGTGTC TTCCTATTGA | GGGAGGAGGTTG TAGGCAAC | 39 | 40 |
|  |  |  |  | 16 | 58b9 | 692b | " | " | " | " |

Size: PCR product Size;
mM MgCl: Mg concentration;
Ann.: Annealing temperature;
P1: P1 probe ID number;
PC: DuPont Library Plate Coordinates;
SCA: DuPont Library Single Clone address;
SEQ-forward and SEQ-backward: forward and backward PCR primers, respectively;
SEQ ID NO:-forward and SEQ ID NO:-backward: Sequence Listing SEQ ID NO: for forward and backward primers, respectively.

TABLE 2

Cross reference to probes of the BAC library. Clone # refers to the clone number provided, e.g., in FIG. 4, while the plate coordinates are the plate coordinates in the Research Genetics BAC library.

| PRIMER NAME | SIZE (bp) | mM MgCl | Ann. | BAC # | BAC Plate Coordinates | SEQ-forward | SEQ-backward | SEQ ID NO:- forward | SEQ ID NO:- backward |
|---|---|---|---|---|---|---|---|---|---|
| 18T F1/B1 | 156 | 3 | 62 | 99 | L11 plate 146 | AGCAAAGCAAA GGTGGCACAC | TGACATGGGAGAA GACACACTTCC | 41 | 42 |
| 9S F1/B1 | 214 | 1.5 | 55 | 97 | E8 plate 183 | AGGTTTACCAA TGTGTTTGG | TCTACATCCCATT CTCTTCTG | 43 | 44 |
| D20S480 | 300 | 3 | 55 | 95 | H15 plate 140 | GTGGTGAACAC CAATAAATGG | AAGCAAATAAAAC CAATAAACTCG | 21 | 22 |
| D20S211 1/2 | 135 | 1.5 | 52 | 103 | A15 plate 188 | TTGGAATCAAT GGAGCAAAA | AGCTTTACCCAAT GTGGTCC | 19 | 20 |
|  |  |  |  | 102 | A1 plate 46 | " | " | " | " |

TABLE 2 -continued

Cross reference to probes of the BAC library. Clone # refers to the clone number provided, e.g., in FIG. 4, while the plate coordinates are the plate coordinates in the Research Genetics BAC library.

| PRIMER NAME | SIZE (bp) | mM MgCl | Ann. | BAC # | BAC Plate Coordinates | SEQ-forward | SEQ-backward | SEQ ID NO:- forward | SEQ ID NO:- backward |
|---|---|---|---|---|---|---|---|---|---|
| 11S-17 F2/B4 | 146 | 3 | 58 | 100 | E4 plate 43 | GCCATGTACCCA CCTGAAAAATC | TCAGAACACCCGT GCAGAATTAAG | 25 | 26 |
|  |  |  |  | 101 | J5 plate 118 | " | " | " | " |

Size: PCR product Size;
mM MgClL: Mg concentration;
Ann.: Annealing temperature;
BAC #: BAC probe ID number;
SEQ-forward and SEQ-backward: forward and backward PCR primers, respectively;
SEQ ID NO:-forward and SEQ ID NO:-backward: Sequence Listing SEQ ID NO: for forward and backward primers, respectively.

and BAC probes are available commercially from Genetic Systems, and Research Genetics, respectively).

cDNA Sequences from the 20q13 Amplicon

Exon trapping (see, e.g., Duyk et al., *Proc. Natl. Acad. Sci. USA*, 87: 8995-8999 (1990) and Church et al., *Nature Genetics*, 6: 98-105 (1994)) was performed on the P1 and BAC clones spanning the ≈600 kb minimum common region of amplification and has isolated more than 200 exons.

Analysis of the exons DNA sequence revealed a number of sequence similarities (85% to 96%) to partial CDNA sequences in the expressed sequence data base (dbest) and to a *S. cerevisiae* chromosome XIV open reading frame. Each P1 clone subjected to exon trapping has produced multiple exons consistent with at least a medium density of genes. Over 200 exons have been trapped and analyzed as well as 200 clones isolated by direct selection from a BT474 cDNA library. In addition a 0.6 Mb genomic interval spanning the minimal amplicon described below is being sequenced. Exon prediction and gene modeling are carried out with XGRAIL, SORFIND, and BLAST programs. Gene fragments identified by these approaches have been analyzed by RT-PCR, Northern and Southern blots. Fifteen unique genes were identified in this way (see, Table 3.

In addition two other genes ZABC1 (SEQ ID NOs:9 and 10) and 1b1 (SEQ ID NO:12) were also were shown to be overexpressed in a variety of different cancer cells.

Sequence information from various cDNA clones are provided below. They are as follows:

3bf4 (SEQ ID NO:1)—3 kb transcript with sequence identity to a tyrosine kinase gene, termed A6, disclosed in Beeler et al. *Mol. Cell. Biol.* 14:982-988 (1994) and WO 95/19439. These references, however, do not disclose that the gene is located in the chromosome 20 amplicon.

1b11 (SEQ ID NO:2)—an approximately 3.5 kb transcript whose expression shows high correlation with the copy number of the amplicon. The sequence shows no homology with sequences in the databases searched.

cc49 (SEQ ID NO:3)—a 6-7 kb transcript which shows homology to C2H2 zinc finger genes.

cc43 (SEQ ID NO:4)—an approximately 4 kb transcript which is expressed in normal tissues, but whose expression in the breast cancer cell line has not been detected.

41.1 (SEQ ID NO:5)—shows homology to the homeobox T shirt gene in Drosophila.

GCAP (SEQ ID NO:6)—encodes a guanino cyclase activating protein which is involved in the biosynthesis of cyclic AMP. As explained in detail below, sequences from this gene can also be used for treatment of retinal degeneration.

1b4 (SEQ ID NO:7)—a serine threonine kinase.

20sa7 (SEQ ID NO:8)—a homolog of the rat gene, BEM-1.

In addition, the entire nucleotide sequence is provided for ZABC-1. ZABC-1 stands for zinc finger amplified in breast cancer. This gene maps to the core of the 20q13.2 amplicon and is overexpressed in primary tumors and breast cancer cell lines having 20q13.2 amplification. The genomic sequence (SEQ ID NO:9) includes roughly 2 kb of the promoter region. SEQ ID NO:10 provides the cDNA sequence derived open reading frame and SEQ ID NO:11 provides the predicted protein sequence. Zinc finger containing genes are often transcription factors that function to modulate the expression of down stream genes. Several known oncogenes are in fact zinc finger containing genes.

This invention also provides the full length cDNA sequence for a cDNA designated 1b1 (SEQ ID NO:12) which is also overexpressed in numerous breast cancer cell lines and some primary tumors.

SEQ ID NO: 45 provides sequence from a genomic clone which is similar to known rat and mouse cyclophilin cDNAs. Rat cyclophilin nucleic acids (e.g., cDNAs) are known; see, GenBank™ under accession No. M19533; Mouse cyclophilin nucleic acids (e.g., cDNAs) are known; see, GenBank™ under accession No. 50620. Accordingly, SEQ ID NO:45 is a putative human cyclophilin gene. The sequence is also associated with amplified sequences from 20q13, and can be used as a probe or probe hybridization target to detect DNA amplification, or RNA overexpression of the corresponding gene.

TABLE 3

Gene fragments identified by exon trapping and analyzed by RT-PCR, Northern and Southern blots.

| Map # | Gene ID | Transcript Size (kb) | EST Identity (>95%) | Cloned Sequence (kb) | Protein Homologies | Map Location |
|---|---|---|---|---|---|---|
| 1 | 20sa7 | — | Yes | 3 | PTP | 3, 18, 99 |
| 2 | 1b11 | 3.5 | No | 1.5 | novel | 18, 3, 99, 69 |
| 3 | 200.1 | — | — | — | — | — |
| 4 | 132.1 | — | — | — | novel | 132 |
| 5 | 132.2 | — | — | — | — | 132 |
| 6 | 3bf4 | 3 | Yes | 3 | PTK | ambiguous |
| 7 | 7.1 | — | — | — | — | 7, 11, 97 |
| 8 | 7.2 | 2.4 | — | — | — | 7, 11, 97 |
| 9 | cc49 | 7, 4 | Yes | 3.6 | Kruppel | 97, 103 |
| 10 | cc43 | 1.4 | Yes | 1.8 | hypothetical yeast protein | 97, 7, 11 |
| 11 | et1807 | 2.5 | Yes | 0.7 | novel | 97, 9 |

TABLE 3-continued

Gene fragments identified by exon trapping and analyzed by RT-PCR, Northern and Southern blots.

| Map # | Gene ID | Transcript Size (kb) | EST Identity (>95%) | Cloned Sequence (kb) | Protein Homologies | Map Location |
|---|---|---|---|---|---|---|
| 12 | et2106 | None detected | Yes | — | — | 95, 39, 38 |
| 13 | 41.1 | 7, 8, 11 | Yes | 3 | homeotic gene | 95, 41, 42 |
| 14 | 67.1 | — | Yes | 2 Kb | | 67 |
| 15 | 67.2 | 0 | Yes | — | cGMP reg. protein | 67 |

20q13 Amplicon Proteins

As indicated above, this invention also provides for proteins encoded by nucleic acid sequences in the 20q13 amplicon (e.g., SEQ ID NOs:1-10, 12, and 45) and subsequences more preferably subsequences of at least 10 amino acids, preferably of at least 20 amino acids, and most preferably of at least 30 amino acids in length. Particularly preferred subsequences are epitopes specific to the 20q13 proteins more preferably epitopes specific to the ZABC1 and 1b1 proteins. Such proteins include, but are not limited to isolated polypeptides comprising at least 10 contiguous amino acids from a polypeptide encoded by the nucleic acids of SEQ ID NOs:1-10, 12, and 45 or from the polypeptide of SEQ ID NO:11 wherein the polypeptide, when presented as an immunogen, elicits the production of an antibody which specifically binds to a polypeptide selected from the group consisting of a polypeptide encoded by the nucleic acids of SEQ ID NOs:1-10, 12, and 45 or from the polypeptide of SEQ ID. NO:11 and the polypeptide does not bind to antisera raised against a polypeptide selected from the group consisting of a polypeptide encoded by the nucleic acids of SEQ ID NOs:1-10, 12, and 45 or from the polypeptide of SEQ ID NO:11 which has been fully immunosorbed with a polypeptide selected from the group consisting of a polypeptide encoded by the nucleic acids of SEQ ID NOs:1-10, 12, and 45 or from the polypeptide of SEQ ID NO:11.

A protein that specifically binds to or that is specifically immunoreactive with an antibody generated against a defined immunogen, such as an immunogen consisting of the amino acid sequence of SEQ ID NO:11 is determined in an immunoassay. The immunoassay uses a polyclonal antiserum which was raised to the protein of SEQ ID NO:11 (the immunogenic polypeptide). This antiserum is selected to have low crossreactivity against other similar known polypeptides and any such crossreactivity is removed by immunoabsorbtion prior to use in the immunoassay (e.g., by immunosorbtion of the antisera with the related polypeptide).

In order to produce antisera for use in an immunoassay, the polypeptide e.g., the polypeptide of SEQ ID NO:11 is isolated as described herein. For example, recombinant protein can be produced in a mammalian or other eukaryotic cell line. An inbred strain of mice is immunized with the protein of SEQ ID NO:11 using a standard adjuvant, such as Freund's adjuvant, and a standard mouse immunization protocol (see Harlow and Lane, supra). Alternatively, a synthetic polypeptide derived from the sequences disclosed herein and conjugated to a carrier protein is used as an immunogen. Polyclonal sera are collected and tittered against the immunogenic polypeptide in an immunoassay, for example, a solid phase immunoassay with the immunogen immobilized on a solid support. Polyclonal antisera with a titer of $10^4$ or greater are selected and tested for their cross reactivity against known polypeptides using a competitive binding immunoassay such as the one described in Harlow and Lane, supra, at pages 570-573. Preferably more than one known polypeptide is used in this determination in conjunction with the immunogenic polypeptide.

The known polypeptides can be produced as recombinant proteins and isolated using standard molecular biology and protein chemistry techniques as described herein.

Immunoassays in the competitive binding format are used for crossreactivity determinations. For example, the immunogenic polypeptide is immobilized to a solid support. Proteins added to the assay compete with the binding of the antisera to the immobilized antigen. The ability of the a proteins to compete with the binding of the antisera to the immobilized protein is compared to the immunogenic polypeptide. The percent crossreactivity for the protein is calculated, using standard calculations. Those antisera with less than 10% crossreactivity to known polypeptides are selected and pooled. The cross-reacting antibodies are then removed from the pooled antisera by immunoabsorbtion with known polypeptide.

The immunoabsorbed and pooled antisera are then used in a competitive binding immunoassay as described herein to compare a "target" polypeptide to the immunogenic polypeptide. To make this comparison, the two polypeptides are each assayed at a wide range of concentrations and the amount of each polypeptide required to inhibit 50% of the binding of the antisera to the immobilized protein is determined using standard techniques. If the amount of the target polypeptide required is less than twice the amount of the immunogenic polypeptide that is required, then the target polypeptide is said to specifically bind to an antibody generated to the immunogenic protein. As a final determination of specificity, the pooled antisera is fully immunosorbed with the immunogenic polypeptide until no binding to the polypeptide used in the immunosorbtion is detectable. The fully immunosorbed antisera is then tested for reactivity with the test polypeptide. If no reactivity is observed, then the test polypeptide is specifically bound by the antisera elicited by the immunogenic protein.

Similarly, in a reciprocal experiment, the pooled antisera is immusorbed with the test polypeptide. If the antisera which remains after the immunosorbtion does not bind to the immunogenic polypeptide (i.e., the polypeptide of SEQ ID NO: 11 used to elicit the antisera) then the test polypeptide is specifically bound by the antisera elicited by the immunogenic peptide.

Detection of 20q13 Abnormalities

One of skill in the art will appreciate that the clones and sequence information provided herein can be used to detect amplifications, or other chromosomal abnormalities, at 20q13 in a biological sample. Generally the methods involve hybridization of probes that specifically bind one or more nucleic acid sequences of the target amplicon with nucleic acids present in a biological sample or derived from a biological sample.

As used herein, a biological sample is a sample of biological tissue or fluid containing cells desired to be screened for chromosomal abnormalities (e.g. amplifications of deletions). In a preferred embodiment, the biological sample is a cell or tissue suspected of being cancerous (transformed). Methods of isolating biological samples are well known to those of skill in the art and include, but are not limited to, aspirations, tissue sections, needle biopsies, and the like. Frequently the sample will be a "clinical sample" which is a sample derived from a patient. It will be recognized that the term "sample" also includes supernatant (containing cells) or the cells themselves from cell cultures, cells from tissue culture and other media in which it may be desirable to detect chromosomal abnormalities.

In a preferred embodiment, a biological sample is prepared by depositing cells, either as single cell suspensions or as tissue preparation, on solid supports such as glass slides and fixed by choosing a fixative which provides the best spatial resolution of the cells and the optimal hybridization efficiency.

Making Probes

Any of the P1 probes listed in Table 1, the BAC probes listed in Table 2, or the cDNAs disclosed here are suitable for use in detecting the 20q13 amplicon. Methods of preparing probes are well known to those of skill in the art (see, e.g. Sambrook et al., *Molecular Cloning: A Laboratory Manual* (2nd ed.), Vols. 1-3, Cold Spring Harbor Laboratory, (1989) or *Current Protocols in Molecular Biology*, F. Ausubel et al., ed. Greene Publishing and Wiley-Interscience, New York (1987))

Given the strategy for making the nucleic acids of the present invention, one of skill can construct a variety of vectors and nucleic acid clones containing functionally equivalent nucleic acids. Cloning methodologies to accomplish these ends, and sequencing methods to verify the sequence of nucleic acids are well known in the art. Examples of appropriate cloning and sequencing techniques, and instructions sufficient to direct persons of skill through many cloning exercises are found in Berger and Kimmel, *Guide to Molecular Cloning Techniques, Methods in Enzymology* volume 152 Academic Press, Inc., San Diego, Calif. (Berger); Sambrook et al. (1989) *Molecular Cloning-A Laboratory Manual* (2nd ed.) Vol. 1-3, Cold Spring Harbor Laboratory, Cold Spring Harbor Press, NY, (Sambrook); and *Current Protocols in Molecular Biology*, F. M. Ausubel et al., eds., Current Protocols, a joint venture between Greene Publishing Associates, Inc. and John Wiley & Sons, Inc., (1994 Supplement) (Ausubel). Product information from manufacturers of biological reagents and experimental equipment also provide information useful in known biological methods. Such manufacturers include the SIGMA chemical company (Saint Louis, Mo.), R&D systems (Minneapolis, Minn.), Pharmacia LKB Biotechnology (Piscataway, N.J.), CLONTECH Laboratories, Inc. (Palo Alto, Calif.), Chem Genes Corp., Aldrich Chemical Company (Milwaukee, Wis.), Glen Research, Inc., GIBCO BRL Life Technologies, Inc. (Gaithersberg, Md.), Fluka Chemica-Biochemika Analytika (Fluka Chemie AG, Buchs, Switzerland), Invitrogen, San Diego, Calif., and Applied Biosystems (Foster City, Calif.), as well as many other commercial sources known to one of skill.

The nucleic acids provided by this invention, whether RNA, cDNA, genomic DNA, or a hybrid of the various combinations, are isolated from biological sources or synthesized in vitro. The nucleic acids and vectors of the invention are present in transformed or transfected whole cells, in transformed or transfected cell lysates, or in a partially purified or substantially pure form.

In vitro amplification techniques suitable for amplifying sequences to provide a nucleic acid, or for subsequent analysis, sequencing or subcloning are known. Examples of techniques sufficient to direct persons of skill through such in vitro amplification methods, including the polymerase chain reaction (PCR) the ligase chain reaction (LCR), Qβ-replicase amplification and other RNA polymerase mediated techniques (e.g., NASBA) are found in Berger, Sambrook, and Ausubel, as well as Mullis et al., (1987) U.S. Pat. No. 4,683, 202; *PCR Protocols A Guide to Methods and Applications* (Innis et al. eds) Academic Press Inc. San Diego, Calif. (1990) (Innis); Arnheim & Levinson (Oct. 1, 1990) C&EN 36-47; *The Journal Of NIH Research* (1991) 3, 81-94; (Kwoh et al. (1989) *Proc. Natl. Acad. Sci. USA* 86, 1173; Guatelli et al. (1990) *Proc. Natl. Acad. Sci. USA* 87, 1874; Lomell et al. (1989) *J. Clin. Chem* 35, 1826; Landegren et al., (1988) *Science* 241, 1077-1080; Van Brunt (1990) *Biotechnology* 8, 291-294; Wu and Wallace, (1989) *Gene* 4, 560; Barringer et al. (1990) *Gene* 89, 117, and Sooknanan and Malek (1995) *Biotechnology* 13: 563-564. Improved methods of cloning in vitro amplified nucleic acids are described in Wallace et al., U.S. Pat. No. 5,426,039. Improved methods of amplifying large nucleic acids are summarized in Cheng et al. (1994) *Nature* 369: 684-685 and the references therein.

Nucleic Acids (e.g., oligonucleotides) for in vitro amplification methods or for use as gene probes, for example, are typically chemically synthesized according to the solid phase phosphoramidite triester method described by Beaucage and Caruthers (1981), *Tetrahedron Letts.*, 22 (20):1859-1862, e.g., using an automated synthesizer, as described in Needham-VanDevanter et al. (1984) *Nucleic Acids Res.*, 12:6159-6168. Purification of oligonucleotides, where necessary, is typically performed by either native acrylamide gel electrophoresis or by anion-exchange HPLC as described in Pearson and Regnier (1983) *J. Chrom.* 255:137-149. The sequence of the synthetic oligonucleotides can be verified using the chemical degradation method of Maxam and Gilbert (1980) in Grossman and Moldave (eds.) Academic Press, New York, *Methods in Enzymology* 65:499-560.

The probes are most easily prepared by combining and labeling one or more of the constructs listed in Tables 1 and 2. Prior to use, the constructs are fragmented to provide smaller nucleic acid fragments that easily penetrate the cell and hybridize to the target nucleic acid. Fragmentation can be by any of a number of methods well known to hose of skill in the art. Preferred methods include treatment with a restriction enzyme to selectively cleave the molecules, or alternatively to briefly heat the nucleic acids in the presence of $Mg^{2+}$. Probes are preferably fragmented to an average fragment length ranging from about 50 bp to about 2000 bp, more preferably from about 100 bp to about 1000 bp and most preferably from about 150 bp to about 500 bp.

Alternatively, probes can be produced by amplifying (e.g. via PCR) selected subsequences from the 20q13 amplicon disclosed herein. The sequences provided herein permit one of skill to select primers that amplify sequences from one or more exons located within the 20q13 amplicon.

Particularly preferred probes include nucleic acids from probes 38, 40, and 79, which corresponds to RMC20C001. In addition, the cDNAs are particularly useful for identifying cells that have increased expression of the corresponding genes, using for instance, Northern blot analysis.

One of skill will appreciate that using the sequence information and clones provided herein, one of skill in the art can isolate the same or similar probes from other human genomic libraries using routine methods (e.g. Southern or Northern Blots).

Similarly, the polypeptides of the invention can be synthetically prepared in a wide variety of well-know ways. For instance, polypeptides of relatively short length can be synthesized in solution or on a solid support in accordance with conventional techniques. See, e.g., Merrifield (1963) *J. Am. Chem. Soc.* 85:2149-2154. Various automatic synthesizers are commercially available and can be used in accordance with known protocols. See, e.g., Stewart and Young (1984) *Solid Phase Peptide Synthesis*, 2d. ed., Pierce Chemical Co. As described in more detail herein, the polypeptide of the invention are most preferably made using recombinant techniques, e.g., by expressing the polypeptides in host cells and purifying the expressed proteins.

In a preferred embodiment, the polypeptides, or subsequences thereof, are synthesized using recombinant DNA methodology. Generally this involves creating a DNA sequence that encodes the protein, through recombinant, synthetic, or in vitro amplification techniques, placing the DNA in an expression cassette under the control of a particular promoter, expressing the protein in a host cell, isolating the expressed protein and, if required, renaturing the protein.

Labeling Probes

Methods of labeling nucleic acids are well known to those of skill in the art. Preferred labels are those that are suitable for use in in situ hybridization. The nucleic acid probes may be detectably labeled prior to the hybridization reaction. Alternatively, a detectable label which binds to the hybridization product may be used. Such detectable labels include any material having a detectable physical or chemical property and have been well-developed in the field of immunoassays.

As used herein, a "label" is any composition detectable by spectroscopic, photochemical, biochemical, immunochemical, or chemical means. Useful labels in the present invention include radioactive labels (e.g. $^{32}P$, $^{125}I$, $^{14}C$, $^{3}H$, and $^{35}S$), fluorescent dyes (e.g. fluorescein, rhodamine, Texas Red, etc.), electron-dense reagents (e.g. gold), enzymes (as commonly used in an ELISA), colorimetric labels (e.g. colloidal gold), magnetic labels (e.g. Dynabeads™), and the like. Examples of labels which are not directly detected but are detected through the use of directly detectable label include biotin and dioxigenin as well as haptens and proteins for which labeled antisera or monoclonal antibodies are available.

The particular label used is not critical to the present invention, so long as it does not interfere with the in situ hybridization of the stain. However, stains directly labeled with fluorescent labels (e.g. fluorescein-12-dUTP, Texas Red-5-dUTP, etc.) are preferred for chromosome hybridization.

A direct labeled probe, as used herein, is a probe to which a detectable label is attached. Because the direct label is already attached to the probe, no subsequent steps are required to associate the probe with the detectable label. In contrast, an indirect labeled probe is one which bears a moiety to which a detectable label is subsequently bound, typically after the probe is hybridized with the target nucleic acid.

In addition the label must be detectible in as low copy number as possible thereby maximizing the sensitivity of the assay and yet be detectible above any background signal. Finally, a label must be chosen that provides a highly localized signal thereby providing a high degree of spatial resolution when physically mapping the stain against the chromosome. Particularly preferred fluorescent labels include fluorescein-12-dUTP and Texas Red-5-dUTP.

The labels may be coupled to the probes in a variety of means known to those of skill in the art. In a preferred embodiment the nucleic acid probes will be labeled using nick translation or random primer extension (Rigby, et al. *J. Mol. Biol.*, 113: 237 (1977) or Sambrook, et al., *Molecular Cloning-A Laboratory Manual*, Cold Spring Harbor Laboratory, Cold Spring Harbor, N.Y. (1985)).

One of skill in the art will appreciate that the probes of this invention need not be absolutely specific for the targeted 20q13 region of the genome. Rather, the probes are intended to produce "staining contrast". "Contrast" is quantified by the ratio of the probe intensity of the target region of the genome to that of the other portions of the genome. For example, a DNA library produced by cloning a particular chromosome (e.g. chromosome 7) can be used as a stain capable of staining the entire chromosome. The library contains both sequences found only on that chromosome, and sequences shared with other chromosomes. Roughly half the chromosomal DNA falls into each class. If hybridization of the whole library were capable of saturating all of the binding sites on the target chromosome, the target chromosome would be twice as bright (contrast ratio of 2) as the other chromosomes since it would contain signal from the both the specific and the shared sequences in the stain, whereas the other chromosomes would only be stained by the shared sequences. Thus, only a modest decrease in hybridization of the shared sequences in the stain would substantially enhance the contrast. Thus contaminating sequences which only hybridize to non-targeted sequences, for example, impurities in a library, can be tolerated in the stain to the extent that the sequences do not reduce the staining contrast below useful levels.

Detecting the 20q13 Amplicon

As explained above, detection of amplification in the 20q13 amplicon is indicative of the presence and/or prognosis of a large number of cancers. These include, but are not limited to breast, ovary, bladder, head and neck, and colon.

In a preferred embodiment, a 20q13 amplification is detected through the hybridization of a probe of this invention to a target nucleic acid (e.g. a chromosomal sample) in which it is desired to screen for the amplification. Suitable hybridization formats are well known to those of skill in the art and include, but are not limited to, variations of Southern Blots, in situ hybridization and quantitative amplification methods such as quantitative PCR (see, e.g. Sambrook, supra., Kallioniemi et al., *Proc. Natl Acad Sci USA*, 89: 5321-5325 (1992), and *PCR Protocols, A Guide to Methods and Applications*, Innis et al., Academic Press, Inc. N.Y., (1990)).

In situ Hybridization

In a preferred embodiment, the 20q13 amplicon is identified using in situ hybridization. Generally, in situ hybridization comprises the following major steps: (1) fixation of tissue or biological structure to analyzed; (2) prehybridization treatment of the biological structure to increase accessibility of target DNA, and to reduce nonspecific binding; (3) hybridization of the mixture of nucleic acids to the nucleic acid in the biological structure or tissue; (4) posthybridization washes to remove nucleic acid fragments not bound in the hybridization and (5) detection of the hybridized nucleic acid fragments. The reagent used in each of these steps and their conditions for use vary depending on the particular application.

In some applications it is necessary to block the hybridization capacity of repetitive sequences. In this case, human genomic DNA is used as an agent to block such hybridization. The preferred size range is from about 200 bp to about 1000 bases, more preferably between about 400 to about 800 bp for double stranded, nick translated nucleic acids.

Hybridization protocols for the particular applications disclosed here are described in Pinkel et al. *Proc. Natl. Acad. Sci. USA*, 85: 9138-9142 (1988) and in EPO Pub. No. 430,402. Suitable hybridization protocols can also be found in *Methods o\in Molecular Biology Vol.* 33: *In Situ Hybridization Protocols*, K. H. A. Choo, ed., Humana Press, Totowa, N.J., (1994). In a particularly preferred embodiment, the hybridization protocol of Kallioniemi et al., *Proc. Natl Acad Sci USA*, 89: 5321-5325 (1992) is used.

Typically, it is desirable to use dual color FISH, in which two probes are utilized, each labelled by a different fluorescent dye. A test probe that hybridizes to the region of interest is labelled with one dye, and a control probe that hybridizes to a different region is labelled with a second dye. A nucleic acid that hybridizes to a stable portion of the chromosome of interest, such as the centromere region, is often most useful as the control probe. In this way, differences between efficiency of hybridization from sample to sample can be accounted for.

The FISH methods for detecting chromosomal abnormalities can be performed on nanogram quantities of the subject nucleic acids. Paraffin embedded tumor sections can be used, as can fresh or frozen material. Because FISH can be applied to the limited material, touch preparations prepared from uncultured primary tumors can also be used (see, e.g., Kallioniemi, A. et al., *Cytogenes. Cell Genet.* 60: 190-193 (1992)). For instance, small biopsy tissue samples from tumors can be used for touch preparations (see, e.g., Kallioniemi, A. et al., *Cytogenet. Cell Genet.* 60: 190-193 (1992)). Small numbers of cells obtained from aspiration biopsy or cells in bodily fluids (e.g., blood, urine, sputum and the like) can also be analyzed. For prenatal diagnosis, appropriate samples will include amniotic fluid and the like.

Southern Blots

In a Southern Blot, a genomic or cDNA (typically fragmented and separated on an electrophoretic gel) is hybridized to a probe specific for the target region. Comparison of the intensity of the hybridization signal from the probe for the target region (e.g., 20q13) with the signal from a probe directed to a control (non amplified) such as centromeric DNA, provides an estimate of the relative copy number of the target nucleic acid.

Detecting Mutations in Genes from the 20q13 Amplicon

The cDNA sequences disclosed here can also be used for detecting mutations (e.g., substitutions, insertions, and deletions) within the corresponding endogenous genes. One of skill will recognize that the nucleic acid hybridization techniques generally described above can be adapted to detect such much mutations. For instance, oligonucleotide probes that distinguish between mutant and wild-type forms of the target gene can be used in standard hybridization assays. In some embodiments, amplification (e.g., using PCR) can be used to increase copy number of the target sequence prior to hybridization.

Assays for Detecting 20q13 Amplicon Proteins

As indicated above, this invention identifies protein products of genes in the 20q13 amplicon that are associated with various cancers. In particular, it was shown that 20q13 proteins were overexpressed in various cancers. The presence or absence and/or level of expression of 20q13 proteins can be indicative of the presence, absence, or extent of a cancer. Thus, 20q13 proteins can provide useful diagnostic markers.

The 20q13 amplicon proteins (e.g., ZABC1 or 1b1) can be detected and quantified by any of a number of means well known to those of skill in the art. These may include analytic biochemical methods such as electrophoresis, capillary electrophoresis, high performance liquid chromatography (HPLC), thin layer chromatography (TLC), hyperdiffusion chromatography, and the like, or various immunological methods such as fluid or gel precipitin reactions, immunodiffusion (single or double), immunoelectrophoresis, radioimmunoassay (RIA), enzyme-linked immunosorbent assays (ELISAs), immunofluorescent assays, western blotting, and the like.

In one preferred embodiment, the 20q13 amplicon proteins are detected in an electrophoretic protein separation such as a one dimensional or two-dimensional electrophoresis, while in a most preferred embodiment, the 20q13 amplicon proteins are detected using an immunoassay.

As used herein, an immunoassay is an assay that utilizes an antibody to specifically bind to the analyte (e.g., ZABC1 or 1b1 proteins). The immunoassay is thus characterized by detection of specific binding of a 20q13 amplicon protein to an anti-20q13 amplicon antibody (e.g., anti-ZABC1 or anti-1b1) as opposed to the use of other physical or chemical properties to isolate, target, and quantify the analyte.

The collection of biological sample and subsequent testing for 20q13 amplicon protein(s) is discussed in more detail below.

A) Sample Collection and Processing

The 20q13 amplicon proteins are preferably quantified in a biological sample derived from a mammal, more preferably from a human patient or from a porcine, murine, feline, canine, or bovine. As used herein, a biological sample is a sample of biological tissue or fluid that contains a 20q13 amplicon protein concentration that may be correlated with a 20q13 amplification. Particularly preferred biological samples include, but are not limited to biological fluids such as blood or urine, or tissue samples including, but not limited to tissue biopsy (e.g., needle biopsy) samples.

The biological sample may be pretreated as necessary by dilution in an appropriate buffer solution or concentrated, if desired. Any of a number of standard aqueous buffer solutions, employing one of a variety of buffers, such as phosphate, Tris, or the like, at physiological pH can be used.

B) Electrophoretic Assays.

As indicated above, the presence or absence of 20q13 amplicon proteins in a biological tissue may be determined using electrophoretic methods. Means of detecting proteins using electrophoretic techniques are well known to those of skill in the art (see generally, R. Scopes (1982) *Protein Purification*, Springer-Verlag, N.Y.; Deutscher, (1990) *Methods in Enzymology Vol.* 182: *Guide to Protein Purification.*, Academic Press, Inc., N.Y.). In a preferred embodiment, the 20q13 amplicon proteins are detected using one-dimensional or two-dimensional electrophoresis. A particularly preferred two-dimensional electrophoresis separation relies on isoelectric focusing (IEF) in immobilized pH gradients for one dimension and polyacrylamide gels for the second dimension. Such assays are described in the cited references and by Patton et al. (1990) *Biotechniques* 8: 518.

C) Immunological Binding Assays.

In a preferred embodiment, the 20q13 amplicon are detected and/or quantified using any of a number of well recognized immunological binding assays (see, e.g., U.S. Pat. Nos. 4,366,241; 4,376,110; 4,517,288; and 4,837,168). For a review of the general immunoassays, see also *Methods in Cell Biology Volume* 37: *Antibodies in Cell Biology*, Asai, ed. Academic Press, Inc. New York (1993); *Basic and Clinical Immunology* 7th Edition, Stites & Terr, eds. (1991).

Immunological binding assays (or immunoassays) typically utilize a "capture agent" to specifically bind to and often immobilize the analyte (in this case 20q13 amplicon). The capture agent is a moiety that specifically binds to the analyte. In a preferred embodiment, the capture agent is an antibody that specifically binds 20q13 amplicon protein(s).

The antibody (e.g., anti-ZABC1 or anti-1b1) may be produced by any of a number of means well known to those of skill in the art (see, e.g. *Methods in Cell Biology Volume* 37: *Antibodies in Cell Biology*, Asai, ed. Academic Press, Inc. New York (1993); and *Basic and Clinical Immunology* 7th Edition, Stites & Terr, eds. (1991)). The antibody may be a whole antibody or an antibody fragment. It may be polyclonal or monoclonal, and it may be produced by challenging an organism (e.g. mouse, rat, rabbit, etc.) with a 20q13 amplicon protein or an epitope derived therefrom. Alternatively, the antibody may be produced de novo using recombinant DNA methodology. The antibody can also be selected from a phage display library screened against 20q13 amplicon (see, e.g. Vaughan et al. (1996) *Nature Biotechnology,* 14: 309-314 and references therein).

Immunoassays also often utilize a labeling agent to specifically bind to and label the binding complex formed by the capture agent and the analyte. The labeling agent may itself be one of the moieties comprising the antibody/analyte complex. Thus, the labeling agent may be a labeled 20q13 amplicon protein or a labeled anti-20q13 amplicon antibody. Alternatively, the labeling agent may be a third moiety, such as another antibody, that specifically binds to the antibody/20q13 amplicon protein complex.

In a preferred embodiment, the labeling agent is a second human 20q13 amplicon protein antibody bearing a label. Alternatively, the second 20q13 amplicon protein antibody may lack a label, but it may, in turn, be bound by a labeled third antibody specific to antibodies of the species from which the second antibody is derived. The second can be modified with a detectable moiety, such as biotin, to which a third labeled molecule can specifically bind, such as enzyme-labeled streptavidin.

Other proteins capable of specifically binding immunoglobulin constant regions, such as protein A or protein G may also be used as the label agent. These proteins are normal constituents of the cell walls of streptococcal bacteria. They exhibit a strong non-immunogenic reactivity with immunoglobulin constant regions from a variety of species. See, generally Kronval, et al., *J. Immunol.,* 111:1401-1406 (1973), and Akerstrom, et al., *J. Immunol.,* 135:2589-2542 (1985).

Throughout the assays, incubation and/or washing steps may be required after each combination of reagents. Incubation steps can vary from about 5 seconds to several hours, preferably from about 5 minutes to about 24 hours. However, the incubation time will depend upon the assay format, analyte, volume of solution, concentrations, and the like. Usually, the assays will be carried out at ambient temperature, although they can be conducted over a range of temperatures, such as 10° C. to 40° C.

1) Non-Competitive Assay Formats.

Immunoassays for detecting 20q13 amplicon proteins may be either competitive or noncompetitive. Noncompetitive immunoassays are assays in which the amount of captured analyte (in this case 20q13 amplicon) is directly measured. In one preferred "sandwich" assay, for example, the capture agent (anti-20q13 amplicon protein antibodies) can be bound directly to a solid substrate where they are immobilized. These immobilized antibodies then capture 20q13 amplicon protein present in the test sample. The 20q13 amplicon protein thus immobilized is then bound by a labeling agent, such as a second human 20q13 amplicon protein antibody bearing a label. Alternatively, the second 20q13 amplicon protein antibody may lack a label, but it may, in turn, be bound by a labeled third antibody specific to antibodies of the species from which the second antibody is derived. The second can be modified with a detectable moiety, such as biotin, to which a third labeled molecule can specifically bind, such as enzyme-labeled streptavidin.

2. Competitive Assay Formats.

In competitive assays, the amount of analyte (20q13 amplicon protein) present in the sample is measured indirectly by measuring the amount of an added (exogenous) analyte (20q13 amplicon proteins such as ZABC1 or 1b1 protein) displaced (or competed away) from a capture agent (e.g., anti-ZABC1 or anti-1b1 antibody) by the analyte present in the sample. In one competitive assay, a known amount of, in this case, 20q13 amplicon protein is added to the sample and the sample is then contacted with a capture agent, in this case an antibody that specifically binds 20q13 amplicon protein. The amount of 20q13 amplicon protein bound to the antibody is inversely proportional to the concentration of 20q13 amplicon protein present in the sample.

In a particularly preferred embodiment, the anti-20q13 protein antibody is immobilized on a solid substrate. The amount of 20q13 amplicon protein bound to the antibody may be determined either by measuring the amount of 20q13 amplicon present in an 20q13 amplicon protein/antibody complex, or alternatively by measuring the amount of remaining uncomplexed 20q13 amplicon protein. The amount of 20q13 amplicon protein may be detected by providing a labeled 20q13 amplicon protein.

A hapten inhibition assay is another preferred competitive assay. In this assay a known analyte, in this case 20q13 amplicon protein is immobilized on a solid substrate. A known amount of anti-20q13 amplicon protein antibody is added to the sample, and the sample is then contacted with the immobilized 20q13 amplicon protein. In this case, the amount of anti-20q13 amplicon protein antibody bound to the immobilized 20q13 amplicon protein is inversely proportional to the amount of 20q13 amplicon protein present in the sample. Again the amount of immobilized antibody may be detected by detecting either the immobilized fraction of antibody or the fraction of the antibody that remains in solution. Detection may be direct where the antibody is labeled or indirect by the subsequent addition of a labeled moiety that specifically binds to the antibody as described above.

3. Other Assay Formats

In a particularly preferred embodiment, Western blot (immunoblot) analysis is used to detect and quantify the presence of 20q13 amplicon protein in the sample. The technique generally comprises separating sample proteins by gel electrophoresis on the basis of molecular weight, transferring the separated proteins to a suitable solid support, (such as a nitrocellulose filter, a nylon filter, or derivatized nylon filter), and incubating the sample with the antibodies that specifically bind 20q13 amplicon protein. The anti-20q13 amplicon protein antibodies specifically bind to 20q13 amplicon protein on the solid support. These antibodies may be directly labeled or alternatively may be subsequently detected using labeled antibodies (e.g., labeled sheep anti-mouse antibodies) that specifically bind to the anti-20q13 amplicon protein.

Other assay formats include liposome immunoassays (LIA), which use liposomes designed to bind specific molecules (e.g., antibodies) and release encapsulated reagents or markers. The released chemicals are then detected according to standard techniques (see, Monroe et al. (1986) *Amer. Clin. Prod. Rev.* 5:34-41).

D) Reduction of Non-Specific Binding.

One of skill in the art will appreciate that it is often desirable to reduce non-specific binding in immunoassays. Particularly, where the assay involves an antigen or antibody immobilized on a solid substrate it is desirable to minimize the amount of non-specific binding to the substrate. Means of reducing such non-specific binding are well known to those of skill in the art. Typically, this involves coating the substrate with a proteinaceous composition. In particular, protein compositions such as bovine serum albumin (BSA), nonfat powdered milk, and gelatin are widely used with powdered milk being most preferred.

E) Labels.

The particular label or detectable group used in the assay is not a critical aspect of the invention, so long as it does not significantly interfere with the specific binding of the antibody used in the assay. The detectable group can be any material having a detectable physical or chemical property.

Such detectable labels have been well-developed in the field of immunoassays and, in general, most any label useful in such methods can be applied to the present invention. Thus, a label is any composition detectable by spectroscopic, photochemical, biochemical, immunochemical, electrical, optical or chemical means. Useful labels in the present invention include magnetic beads (e.g. Dynabeads™), fluorescent dyes (e.g., fluorescein isothiocyanate, texas red, rhodamine, and the like), radiolabels (e.g., $^3H$, $^{125}I$, $^{35}S$, $^{14}C$, or $^{32}P$), enzymes (e.g., horse radish peroxidase, alkaline phosphatase and others commonly used in an ELISA), and colorimetric labels such as colloidal gold or colored glass or plastic (e.g. polystyrene, polypropylene, latex, etc.) beads.

The label may be coupled directly or indirectly to the desired component of the assay according to methods well known in the art. As indicated above, a wide variety of labels may be used, with the choice of label depending on sensitivity required, ease of conjugation with the compound, stability requirements, available instrumentation, and disposal provisions.

Non-radioactive labels are often attached by indirect means. Generally, a ligand molecule (e.g., biotin) is covalently bound to the molecule. The ligand then binds to an anti-ligand (e.g., streptavidin) molecule which is either inherently detectable or covalently bound to a signal system, such as a detectable enzyme, a fluorescent compound, or a chemiluminescent compound. A number of ligands and anti-ligands can be used. Where a ligand has a natural anti-ligand, for example, biotin, thyroxine, and cortisol, it can be used in conjunction with the labeled, naturally occurring anti-ligands. Alternatively, any haptenic or antigenic compound can be used in combination with an antibody.

The molecules can also be conjugated directly to signal generating compounds, e.g., by conjugation with an enzyme or fluorophore. Enzymes of interest as labels will primarily be hydrolases, particularly phosphatases, esterases and glycosidases, or oxidoreductases, particularly peroxidases. Fluorescent compounds include fluorescein and its derivatives, rhodamine and its derivatives, dansyl, umbelliferone, etc. Chemiluminescent compounds include luciferin, and 2,3-dihydrophthalazinediones, e.g., luminol. For a review of various labeling or signal producing systems which may be used, see, U.S. Pat. No. 4,391,904).

Means of detecting labels are well known to those of skill in the art. Thus, for example, where the label is a radioactive label, means for detection include a scintillation counter or photographic film as in autoradiography. Where the label is a fluorescent label, it may be detected by exciting the fluorochrome with the appropriate wavelength of light and detecting the resulting fluorescence. The fluorescence may be detected visually, by means of photographic film, by the use of electronic detectors such as charge coupled devices (CCDs) or photomultipliers and the like. Similarly, enzymatic labels may be detected by providing the appropriate substrates for the enzyme and detecting the resulting reaction product. Finally simple colorimetric labels may be detected simply by observing the color associated with the label. Thus, in various dipstick assays, conjugated gold often appears pink, while various conjugated beads appear the color of the bead.

Some assay formats do not require the use of labeled components. For instance, agglutination assays can be used to detect the presence of the target antibodies. In this case, antigen-coated particles are agglutinated by samples comprising the target antibodies. In this format, none of the components need be labeled and the presence of the target antibody is detected by simple visual inspection.

G) Substrates.

As mentioned above, depending upon the assay, various components, including the antigen, target antibody, or anti-human antibody, may be bound to a solid surface. Many methods for immobilizing biomolecules to a variety of solid surfaces are known in the art. For instance, the solid surface may be a membrane (e.g., nitrocellulose), a microtiter dish (e.g., PVC, polypropylene, or polystyrene), a test tube (glass or plastic), a dipstick (e.g. glass, PVC, polypropylene, polystyrene, latex, and the like), a microcentrifuge tube, or a glass or plastic bead. The desired component may be covalently bound or noncovalently attached through nonspecific bonding.

A wide variety of organic and inorganic polymers, both natural and synthetic may be employed as the material for the solid surface. Illustrative polymers include polyethylene, polypropylene, poly(4-methylbutene), polystyrene, polymethacrylate, poly(ethylene terephthalate), rayon, nylon, poly(vinyl butyrate), polyvinylidene difluoride (PVDF), silicones, polyformaldehyde, cellulose, cellulose acetate, nitrocellulose, and the like. Other materials which may be employed, include paper, glasses, ceramics, metals, metalloids, semiconductive materials, cements or the like. In addition, are included substances that form gels, such as proteins (e.g., gelatins), lipopolysaccharides, silicates, agarose and polyacrylamides can be used. Polymers which form several aqueous phases, such as dextrans, polyalkylene glycols or surfactants, such as phospholipids, long chain (12-24 carbon atoms) alkyl ammonium salts and the like are also suitable. Where the solid surface is porous, various pore sizes may be employed depending upon the nature of the system.

In preparing the surface, a plurality of different materials may be employed, particularly as laminates, to obtain various properties. For example, protein coatings, such as gelatin can be used to avoid non-specific binding, simplify covalent conjugation, enhance signal detection or the like.

If covalent bonding between a compound and the surface is desired, the surface will usually be polyfunctional or be capable of being polyfunctionalized. Functional groups which may be present on the surface and used for linking can include carboxylic acids, aldehydes, amino groups, cyano groups, ethylenic groups, hydroxyl groups, mercapto groups and the like. The manner of linking a wide variety of compounds to various surfaces is well known and is amply illustrated in the literature. See, for example, *Immobilized Enzymes*, Ichiro Chibata, Halsted Press, New York, 1978, and Cuatrecasas (1970) *J. Biol. Chem.* 245 3059).

In addition to covalent bonding, various methods for non-covalently binding an assay component can be used. Noncovalent binding is typically nonspecific absorption of a compound to the surface. Typically, the surface is blocked with a second compound to prevent nonspecific binding of labeled assay components. Alternatively, the surface is designed such that it nonspecifically binds one component but does not significantly bind another. For example, a surface bearing a lectin such as Concanavalin A will bind a carbohydrate containing compound but not a labeled protein that lacks glycosylation. Various solid surfaces for use in noncovalent attachment of assay components are reviewed in U.S. Pat. Nos. 4,447,576 and 4,254,082.

Kits Containing 20q13 Amplicon Probes

This invention also provides diagnostic kits for the detection of chromosomal abnormalities at 20q13. In a preferred embodiment, the kits include one or more probes to the 20q13 amplicon and/or antibodies to a 20q13 amplicon (e.g., anti-ZABC1 or anti-1b1) described herein. The kits can additionally include blocking probes, instructional materials describing how to use the kit contents in detecting 20q13 amplicons. The kits may also include one or more of the following: various labels or labeling agents to facilitate the detection of the probes, reagents for the hybridization including buffers, a metaphase spread, bovine serum albumin (BSA) and other blocking agents, sampling devices including fine needles, swabs, aspirators and the like, positive and negative hybridization controls and so forth.

Expression of cDNA Clones

One may express the desired polypeptides encoded by the cDNA clones disclosed here, or by subcloning cDNA portions of genomic sequences in a recombinantly engineered cell such as bacteria, yeast, insect (especially employing baculoviral vectors), or mammalian cell. It is expected that those of skill in the art are knowledgeable in the numerous expression systems available for expression of the cDNAs. No attempt to describe in detail the various methods known for the expression of proteins in prokaryotes or eukaryotes will be made.

In brief summary, the expression of natural or synthetic nucleic acids encoding polypetides of the invention will typically be achieved by operably linking the DNA or cDNA to a promoter (which is either constitutive or inducible), followed by incorporation into an expression vector. The vectors can be suitable for replication and integration in either prokaryotes or eukaryotes. Typical expression vectors contain transcription and translation terminators, initiation sequences, and promoters useful for regulation of the expression of the DNA encoding the polypeptides. To obtain high level expression of a cloned gene, it is desirable to construct expression plasmids which contain, at the minimum, a strong promoter to direct transcription, a ribosome binding site for translational initiation, and a transcription/translation terminator.

Examples of regulatory regions suitable for this purpose in *E. coli* are the promoter and operator region of the *E. coli* tryptophan biosynthetic pathway as described by Yanofsky, C., 1984, J. Bacteriol., 158:1018-1024 and the leftward promoter of phage lambda ($P_L$) as described by Herskowitz, I. and Hagen, D., 1980, Ann. Rev. Genet., 14:399-445. The inclusion of selection markers in DNA vectors transformed in *E. coli* is also useful. Examples of such markers include genes specifying resistance to ampicillin, tetracycline, or chloramphenicol. Expression systems are available using *E. coli, Bacillus* sp. (Palva, I et al., 1983, Gene 22:229-235; Mosbach, K. et al. Nature, 302:543-545 and *Salmonella. E. coli* systems are preferred.

The polypeptides produced by prokaryote cells may not necessarily fold properly. During purification from *E. coli*, the expressed polypeptides may first be denatured and then renatured. This can be accomplished by solubilizing the bacterially produced proteins in a chaotropic agent such as guanidine HCl and reducing all the cysteine residues with a reducing agent such as beta-mercaptoethanol. The polypeptides are then renatured, either by slow dialysis or by gel filtration. U.S. Pat. No. 4,511,503.

A variety of eukaryotic expression systems such as yeast, insect cell lines and mammalian cells, are known to those of skill in the art. As explained briefly below, the polypeptides may also be expressed in these eukaryotic systems.

Synthesis of heterologous proteins in yeast is well known and described. *Methods in Yeast Genetics*, Sherman, F., et al., Cold Spring Harbor Laboratory, (1982) is a well recognized work describing the various methods available to produce the polypeptides in yeast. A number of yeast expression plasmids like YEp6, YEp13, YEp4 can be used as vectors. A gene of interest can be fused to any of the promoters in various yeast vectors. The above-mentioned plasmids have been fully described in the literature (Botstein, et al., 1979, Gene, 8:17-24; Broach, et al., 1979, Gene, 8:121-133).

Illustrative of cell cultures useful for the production of the polypeptides are cells of insect or mammalian origin. Mammalian cell systems often will be in the form of monolayers of cells although mammalian cell suspensions may also be used. Illustrative examples of mammalian cell lines include VERO and HeLa cells, Chinese hamster ovary (CHO) cell lines, W138, BHK, Cos-7 or MDCK cell lines.

As indicated above, the vector, e. g., a plasmid, which is used to transform the host cell, preferably contains DNA sequences to initiate transcription and sequences to control the translation of the antigen gene sequence. These sequences are referred to as expression control sequences. When the host cell is of insect or mammalian origin illustrative expression control sequences are often obtained from the SV-40 promoter (Science, 222:524-527, 1983), the CMV I.E. Promoter (Proc. Natl. Acad. Sci. 81:659-663, 1984) or the metallothionein promoter (Nature 296:39-42, 1982). The cloning vector containing the expression control sequences is cleaved using restriction enzymes and adjusted in size as necessary or desirable and ligated with the desired DNA by means well known in the art.

As with yeast, when higher animal host cells are employed, polyadenlyation or transcription terminator sequences from known mammalian genes need to be incorporated into the vector. An example of a terminator sequence is the polyadenlyation sequence from the bovine growth hormone gene. Sequences for accurate splicing of the transcript may also be included. An example of a splicing sequence is the VP1 intron from SV40 (Sprague, J. et al., 1983, J. Virol. 45: 773-781).

Additionally, gene sequences to control replication in the host cell may be incorporated into the vector such as those found in bovine papilloma virus type-vectors. Saveria-Campo, M., 1985, "Bovine Papilloma virus DNA a Eukaryotic Cloning Vector" in DNA Cloning Vol. II a Practical Approach Ed. D.M. Glover, IRL Press, Arlington, Va. pp. 213-238.

Therapeutic and Other Uses of cDNAs and Their Gene Products

The cDNA sequences and the polypeptide products of the invention can be used to modulate the activity of the gene products of the endogenous genes corresponding to the cDNAs. By modulating activity of the gene products, pathological conditions associated with their expression or lack of expression can be treated. Any of a number of techniques well known to those of skill in the art can be used for this purpose.

The cDNAs of the invention are particularly used for the treatment of various cancers such as cancers of the breast, ovary, bladder, head and neck, and colon. Other diseases may also be treated with the sequences of the invention. For instance, as noted above, GCAP (SEQ. ID. No: 6) encodes a guanino cyclase activating protein which is involved in the biosynthesis of cyclic AMP. Mutations in genes involved in the biosynthesis of cyclic AMP are known to be associated with hereditary retinal degenerative diseases. These diseases are a group of inherited conditions in which progressive, bilateral degeneration of retinal structures leads to loss of retinal function. These diseases include age-related macular degeneration, a leading cause of visual impairment in the elderly; Leber's congenital amaurosis, which causes its victims to be born blind; and retinitis pigmentosa ("RP"), one of the most common forms of inherited blindness. RP is the name given to those inherited retinopathies which are characterized by loss of retinal photoreceptors (rods and cones), with retinal electrical responses to light flashes (i.e. eletroretinograms, or "ERGs") that are reduced in amplitude.

The mechanism of retinal photoreceptor loss or cell death in different retinal degenerations is not fully understood. Mutations in a number of different genes have been identified as the primary genetic lesion in different forms of human RP. Affected genes include rhodopsin, the alpha and beta subunits of cGMP photodiesterase, and peripherin-RDS (Dryja, T. P. et al., *Invest. Ophthalmol. Vis. Sci.* 36, 1197-1200 (1995)). In all cases the manifestations of the disorder regardless of the specific primary genetic mutation is similar, resulting in photoreceptor cell degeneration and blindness.

Studies on animal models of retinal degeneration have been the focus of many laboratories during the last decade. The mechanisms that are altered in some of the mutations leading to blindness have been elucidated. This would include the inherited disorders of the rd mouse. The rd gene encodes the beta subunit of cGMP-phosphodiesterase (PDE) (Bowes, C. et al., *Nature* 347, 677-680 (1990)), an enzyme of fundamental importance in normal visual function because it is a key component in the cascade of events that takes place in phototransduction.

The polypeptides encoded by the cDNAs of the invention can be used as immunogens to raise antibodies either polyclonal or monoclonal. The antibodies can be used to detect the polypeptides for diagnostic purposes, as therapeutic agents to inhibit the polypeptides, or as targeting moieties in immunotoxins. The production of monoclonal antibodies against a desired antigen is well known to those of skill in the art and is not reviewed in detail here.

Those skilled in the art recognize that there are many methods for production and manipulation of various immunoglobulin molecules. As used herein, the terms "immunoglobulin" and "antibody" refer to a protein consisting of one or more polypeptides substantially encoded by immunoglobulin genes. Immunoglobulins may exist in a variety of forms besides antibodies, including for example, Fv, Fab, and $F(ab)_2$, as well as in single chains. To raise monoclonal antibodies, antibody-producing cells obtained from immunized animals (e.g., mice) are immortalized and screened, or screened first for the production of the desired antibody and then immortalized. For a discussion of general procedures of monoclonal antibody production see Harlow and Lane, *Antibodies, A Laboratory Manual* Cold Spring Harbor Publications, N.Y. (1988).

The antibodies raised by these techniques can be used in immunodiagnostic assays to detect or quantify the expression of gene products from the nucleic acids disclosed here. For instance, labeled monoclonal antibodies to polypeptides of the invention can be used to detect expression levels in a biological sample. For a review of the general procedures in diagnostic immunoassays, see *Basic and Clinical Immunology* 7th Edition D. Stites and A. Terr ed. (1991).

The polynucleotides of the invention are particularly useful for gene therapy techniques well known to those skilled in the art. Gene therapy as used herein refers to the multitude of techniques by which gene expression may be altered in cells. Such methods include, for instance, introduction of DNA encoding ribozymes or antisense nucleic acids to inhibit expression as well as introduction of functional wild-type genes to replace mutant genes (e.g., using wild-type GCAP genes to treat retinal degeneration). A number of suitable viral vectors are known. Such vectors include retroviral vectors (see Miller, *Curr. Top. Microbiol. Immunol.* 158: 1-24 (1992); Salmons and Gunzburg, *Human Gene Therapy* 4: 129-141 (1993); Miller et al., *Methods in Enzymology* 217: 581-599, (1994)) and adeno-associated vectors (reviewed in Carter, *Curr. Opinion Biotech.* 3: 533-539 (1992); Muzcyzka, *Curr. Top. Microbiol. Immunol.* 158: 97-129 (1992)). Other viral vectors that may be used within the methods include adenoviral vectors, herpes viral vectors and Sindbis viral vectors, as generally described in, e.g., Jolly, *Cancer Gene Therapy* 1:51-64 (1994); Latchman, *Molec. Biotechnol.* 2:179-195 (1994); and Johanning et al., *Nucl. Acids Res.* 23:1495-1501 (1995).

Delivery of nucleic acids linked to a heterologous promoter-enhancer element via liposomes is also known (see, e.g., Brigham, et al. (1989) *Am. J. Med. Sci.,* 298:278-281; Nabel, et al. (1990) *Science,* 249:1285-1288; Hazinski, et al. (1991) *Am. J. Resp. Cell Molec.* Biol., 4:206-209; and Wang and Huang (1987) *Proc. Natl. Acad. Sci.* (USA), 84:7851-7855); coupled to ligand-specific, cation-based transport systems (Wu and Wu (1988) *J. Biol. Chem.,* 263:14621-14624). Naked DNA expression vectors have also been described (Nabel et al. (1990), supra); Wolff et al. (1990) *Science,* 247:1465-1468).

The nucleic acids and encoded polypeptides of the invention can be used directedly to inhibit the endogenous genes or their gene products. For instance, Inhibitory nucleic acids may be used to specifically bind to a complementary nucleic acid sequence. By binding to the appropriate target sequence, an RNA-RNA, a DNA-DNA, or RNA-DNA duplex is formed. These nucleic acids are often termed "antisense" because they are usually complementary to the sense or coding strand of the gene, although approaches for use of "sense" nucleic acids have also been developed. The term "inhibitory nucleic acids" as used herein, refers to both "sense" and "antisense" nucleic acids. Inhibitory nucleic acid methods encompass a number of different approaches to altering expression of specific genes that operate by different mechanisms.

In brief, inhibitory nucleic acid therapy approaches can be classified into those that target DNA sequences, those that target RNA sequences (including pre-mRNA and mRNA), those that target proteins (sense strand approaches), and those that cause cleavage or chemical modification of the target nucleic acids (ribozymes). These different types of inhibitory nucleic acid technology are described, for instance, in Helene, C. and Toulme, J. (1990) *Biochim. Biophys. Acta.,* 1049:99-125. Inhibitory nucleic acid complementary to regions of c-myc mRNA has been shown to inhibit c-myc protein expression in a human promyelocytic leukemia cell line, HL60, which overexpresses the c-myc protoncogene. See Wickstrom E. L., et al., (1988) *PNAS* (USA), 85:1028-1032 and Harel-Bellan, A., et al., (1988) *Exp. Med.,* 168: 2309-2318.

The encoded polypeptides of the invention can also be used to design molecules (peptidic or nonpeptidic) that inhibit the endogenous proteins by, for instance, inhibiting interaction between the protein and a second molecule specifically recognized by the protein. Methods for designing such molecules are well known to those skilled in the art.

For instance, polypeptides can be designed which have sequence identity with the encoded proteins or may comprise modifications (conservative or non-conservative) of the sequences. The modifications can be selected, for example, to alter their in vivo stability. For instance, inclusion of one or more D-amino acids in the peptide typically increases stability, particularly if the D-amino acid residues are substituted at one or both termini of the peptide sequence.

The polypeptides can also be modified by linkage to other molecules. For example, different N- or C-terminal groups may be introduced to alter the molecule's physical and/or chemical properties. Such alterations may be utilized to affect, for example, adhesion, stability, bio-availability, localization or detection of the molecules. For diagnostic purposes, a wide variety of labels may be linked to the terminus, which may provide, directly or indirectly, a detectable signal. Thus, the polypeptides may be modified in a variety of ways for a variety of end purposes while still retaining biological activity.

EXAMPLES

The following examples are offered to illustrate, but not to limit the present invention.

Example 1

Prognostic Implications of Amplification of Chromosomal Region 20q13 in Breast Cancer
Patients and Tumor Material.

Tumor samples were obtained from 152 women who underwent surgery for breast cancer between 1987 and 1992 at the Tampere University or City Hospitals. One hundred and forty-two samples were from primary breast carcinomas and 11 from metastatic tumors. Specimens from both the primary tumor and a local metastasis were available from one patient. Ten of the primary tumors that were either in situ or mucinous carcinomas were excluded from the material, since the specimens were considered inadequate for FISH studies. Of the remaining 132 primary tumors, 128 were invasion ductal and 4 lobular carcinomas. The age of the patients ranged from 29 to 92 years (mean 61). Clinical follow-up was available from 129 patients. Median follow-up period was 45 months (range 1.4-1.77 months). Radiation therapy was given to 77 of the 129 patients (51 patients with positive and 26 with negative lymph nodes), and systemic adjuvant therapy to 36 patients (33 with endocrine and 3 with cytotoxic chemotherapy). Primary tumor size and axillary node involvement were determined according to the tumor-node metastasis (TNM) classification. The histopathological diagnosis was evaluated according to the World Health Organization (11). The carcinomas were graded on the basis of the tubular arrangement of cancer cells, nuclear atypia, and frequency of mitotic or hyperchromatic nuclear figures according to Bloom and Richardson, *Br. J. Cancer,* 11: 359-377 (1957).

Surgical biopsy specimens were frozen at −70° C. within 15 minutes of removal. Cryostat sections (5-6 µm) were prepared for intraoperative histopathological diagnosis, and additional thin sections were cut for immunohistochemical studies. One adjacent 200 µm thick section was cut for DNA flow cytometric and FISH studies.
Cell Preparation for FISH.

After histological verification that the biopsy specimens contained a high proportion of tumor cells, nuclei were isolated from 200 µm frozen sections according to a modified Vindelov procedure for DNA flow cytometry, fixed and dropped on slides for FISH analysis as described by Hyytinen et al., *Cytometry* 16: 93-99 (1994). Foreskin fibroblasts were used as negative controls in amplification studies and were prepared by harvesting cells at confluency to obtain G1 phase enriched interphase nuclei. All samples were fixed in methanol-acetic-acid (3:1).
Probes.

Five probes mapping to the 20q13 region were used (see Stokke, et al., *Genomics,* 26: 134-137 (1995)). The probes included P1-clones for melanocortin-3-receptor (probe MC3R, fractional length from p-arm telomere (Flpter 0.81) and phosphoenolpyruvate carboxy kinase (PCK, Flpter 0.84), as well as anonymous cosmid clones RMC20CO26 (Flpter 0.79). In addition, RMC20C001 (Flpter 0.825) and RMC20C030 (Flpter 0.85) were used. Probe RMC20C001 was previously shown to define the region of maximum amplification (Tanner et al., *Cancer Res,* 54: 4257-4260 (1994)). One cosmid probe mapping to the proximal p-arm, RMC20C038 (FLpter 0.237) was used as a chromosome-specific reference probe. Test probes were labeled with biotin-14-dATP and the reference probe with digoxigenin-11-dUTP using nick translation (Kallioniemi et al., *Proc. Natl Acad Sci USA,* 89: 5321-5325 (1992)).
Fluorescence in Situ Hybridization.

Two-color FISH was performed using biotin-labeled 20q13-specific probes and digoxigenin-labelled 20p reference probe essentially as described (Id.). Tumor samples were postfixed in 4% paraformaldtheyde/phosphate-buffered saline for 5 min at 4 C prior to hybridization, dehydrated in 70%, 85% and 100% ethanol, air dried, and incubated for 30 min at 80° C. Slides were denatured in a 70% formamide/2× standard saline citrate solution at 72-74° C. for 3 min, followed by a proteinase K digestion (0.5 µg/ml). The hybridization mixture contained 18 ng of each of the labeled probes and 10 µg human placental DNA. After hybridization, the probes were detected immunochemically with avidin-FITC and anti-digoxigenin Rhodamine. Slides were counterstained with 0.2 µM 4,6-diamidino-2-phenylindole (DAPI) in an antifade solution.
Fluorescence Microscopy and Scoring of Signals in Interphase Nuclei.

A Nikon fluorescence microscope equipped with double band-bass filters (Chromatechnology, Brattleboro, Vt., USA) and 63× objective (NA 1.3) was used for simultaneous visualization of FITC and Rhodamine signals. At least 50 non-overlapping nuclei with intact morphology based on the DAPI counterstaining were scored to determine the number of test and reference probe hybridization signals. Leukocytes infiltrating the tumor were excluded from analysis. Control hybridizations to normal fibroblast interphase nuclei were done to ascertain that the probes recognized a single copy target and that the hybridization efficiencies of the test and reference probes were similar.

The scoring results were expressed both as the mean number of hybridization signals per cell and as mean level of amplification (=mean of number of signals relative to the number of reference probe signals).
DNA Flow Cytometry and Steroid Receptor Analyses.

DNA flow cytometry was performed from frozen 200 µm sections as described by Kallioniemi, *Cytometry* 9: 164-169 (1988). Analysis was carried out using an EPICS C flow cytometer (Coulter Electronics Inc., Hialeah, Fla., USA) and the MultiCycle program (Phoenix Flow Systems, San Diego, Calif., USA). DNA-index over 1.07 (in over 20% of cells) was used as a criterion for DNA aneuploidy. In DNA aneuploid histograms, the S-phase was analyzed only from the aneuploid clone. Cell cycle evaluation was successful in 86% (108/126) of the tumors.

Estrogen (ER) and progesterone (PR) receptors were detected immunohistochemically. from cryostat sections as previously described (17). The staining results were semi-quantitatively evaluated and a histoscore greater than or equal to 100 was considered positive for both ER and PR (17).
Statistical Methods.

Contingency tables were analyzed with Chi square test for trend. Association between S-phase fraction (continuous variable) and 20q13 amplification was analyzed with Kruskal-Wallis test. Analysis of disease-free survival was performed using the BMDPIL program and Mautel-Cox test and Cox's proportional hazards model (BMDP2L program) was used in multivariate regression analysis (Dixon *BMDP*

Statistical Software. London, Berkeley, Los Angeles: University of California Press, (1981)).
Amplification of 20q13 in Primary Breast Carcinomas by Fluorescence in Situ Hybridization.

The minimal region probe RMC20C001 was used in FISH analysis to assess the 20q13 amplification. FISH was used to analyze both the total number of signals in individual tumor cells and to determine the mean level of amplification (mean copy number with the RMC20C001 probe relative to a 20p-reference probe). In addition, the distribution of the number of signals in the tumor nuclei was also assessed. Tumors were classified into three categories: no. low and high level of amplification. Tumors classified as not amplified showed less than 1.5 than 1.5 fold-copy number of the RMC20C001 as compared to the p-arm control. Those classified as having low-level amplification had 1.5-3-fold average level of amplification. Tumors showing over 3-fold average level of amplification were classified as highly amplified.

The highly amplified tumors often showed extensive intratumor heterogeneity with up to 40 signals in individual tumor cells. In highly amplified tumors, the RMC20C001 probe signals were always arranged in clusters by FISH, which indicates location of the amplified DNA sequences in close proximity to one another e.g. in a tandem array. Low level 20q13 amplification was found in 29 of the 132 primary tumors (22%), whereas nine cases (6.8%) showed high level amplification. The overall prevalence of increased copy number in 20q13 was thus 29% (38/132).

Defining the Minimal Region of Amplification.

The average copy number of four probes flanking RMC20C001 was determined in the nine highly amplified tumors. The flanking probes tested were malanocortin-3-receptor (MC3R, FLpter 0.81), phosphoenolpyruvate carboxykinase (PCK, 0.84), RMC20C026 (0.79) and RMC20C030 (0.85). The amplicon size and location varied slightly from one tumor to another but RMC20C001 was the only probe consistently highly amplified in all nine cases.

Association of 20q13 Amplification with Pathological and Biological Features.

The 20q13 amplification was significantly associated with high histologic grade of the tumors (p=0.01). This correlation was seen both in moderately and highly amplified tumors (Table 4). Amplification of 20q13 was also significantly associated with aneuploidy as determined by DNA flow cytometry (p=0.01, Table 4) The mean cell proliferation activity, measured as the percentage of cells in the S-phase fraction, increased (p=0.0085 by Kruskal-Wallis test) with the level of amplification in tumors with no, low and high levels of amplification (Table 4). No association was found with the age of the patient, primary tumor size, axillary nodal or steroid hormone-receptor status (Table 4).

TABLE 4

Clinicopathological correlations of amplification at chromosomal region 20q13 in 132 primary breast cancers.

| Pathobiologic feature | 20q13 amplification status | | | p-value[1] |
|---|---|---|---|---|
| | NO Number of patients (%) | LOW LEVEL Number of patients (%) | HIGH LEVEL Number of patients (%) | |
| All primary tumors | 94 (71%) | 29 (22%) | 9 (6.8%) | |
| Age of patients | | | | |
| <50 years | 17 (65%) | 6 (23%) | 3 (12%) | .39 |
| ≥50 years | 77 (73%) | 23 (22%) | 6 (5.7%) | |
| Tumor size | | | | |
| <2 cm | 33 (79%) | 7 (17%) | 2 (4.8%) | .16 |
| ≥2 cm | 58 (67%) | 22 (25%) | 7 (8.0%) | |
| Nodal status | | | | |
| Negative | 49 (67%) | 19 (26%) | 5 (6.8%) | .41 |
| Positive | 41 (75%) | 10 (18%) | 4 (7.3%) | |
| Histologic grade | | | | |
| I-II | 72 (76%) | 18 (19%) | 5 (5.3%) | .01 |
| III | 16 (52%) | 11 (35%) | 4 (13%) | |
| Estrogen receptor status | | | | |
| Negative | 30 (67%) | 10 (22%) | 5 (11%) | .42 |
| Positive | 59 (72%) | 19 (23%) | 4 (4.9%) | |
| Progesterone receptor status | | | | |
| Negative | 57 (69%) | 20 (24%) | 6 (7.2%) | .53 |
| Positive | 32 (74%) | 8 (19%) | 3 (7.0%) | |
| DNA ploidy | | | | |
| Diploid | 45 (82%) | 8 (14.5%) | 2 (3.6%) | .01 |
| Aneuploid | 44 (62%) | 20 (28%) | 7 (10%) | |
| S-phase fraction (%) | mean ± SD 9.9 ± 7.2 | mean ± SD 12.6 ± 6.7 | mean ± SD 19.0 ± 10.5 | .0085[1] |

[1]Kruskal-Wallis Test.

Relationship Between 20q13 Amplification and Disease-Free Survival.

Disease-free survival of patients with high-level 20q13 amplification was significantly shorter than for patients with no or only low-level amplification (p-0.04). Disease-free survival of patients with moderately amplified tumors did not differ significantly from that of patients with no amplification. Among the node-negative patients (n=79), high level 20q13 amplification was a highly significant prognostic factor for shorter disease-free survival (p=0.002), even in multivariate Cox's regression analysis (p=0.026) after adjustment for tumor size ER, PR grade, ploidy and S-phase fraction.

20q13 Amplification in Metastatic Breast Tumors.

Two of 11 metastatic breast tumors had low level and one high level 20q13 amplification. Thus, the overall prevalence (27%) of increased 20q13 copy number in metastatic tumors was a similar to that observed in the primary tumors. Both a primary and a metastatic tumor specimens were available from one of the patients. This 29-year old patient developed a pectoral muscle infiltrating metastasis eight months after total mastectomy. The patient did not receive adjuvant or radiation therapy after mastectomy. The majority of tumor cells in the primary tumor showed a low level amplification, although individual tumor cells (less than 5% of total) contained 8-20 copies per cell by FISH. In contrast, all tumor cells from metastasis showed high level 20q13 amplification (12-50 copies per cell). The absolute copy number of the reference probe remained the same suggesting that high level amplification was not a result of an increased degree of aneuploidy.

Diagnostic and Prognostic Value of the 20q13 Amplification.

The present findings suggest that the newly-discovered 20q13 amplification may be an important component of the genetic progression pathway of certain breast carcinomas. Specifically, the foregoing experiments establish that: 1) High-level 20q13 amplification, detected in 7% of the tumors, was significantly associated with decreased disease-free survival in node-negative breast cancer patients, as well as with indirect indicators of high-malignant potential, such as high grade and S-phase fraction. 2) Low-level amplification, which was much more common, was also associated with clinicopathological features of aggressive tumors, but was not prognostically significant. 3) The level of amplification of RMC20C001 remains higher than amplification of nearby candidate genes and loci indicating that a novel oncogene is located in the vicinity of RMC20C001.

High-level 20q13 amplification was defined by the presence of more than 3-fold higher copy number of the 20q13 amplification is somewhat lower than the amplification frequencies reported for some of the other breast cancer oncogenes, such as ERBB2 (17q12) and Cyclin-D (11q13) (Borg et al., Oncogene, 6: 137-143 (1991), Van de Vijver et al. Adv. Canc. Res., 61: 25-56 (1993)). However, similar to what has been previously found with these other oncogenes (Swab, et al., Genes Chrom. Canc., 1: 181-193 (1990), Borg et al., supra.), high-level 20q13 amplification was more common in tumors with high grade or high S-phase fraction and in cases with poor prognosis. Although only a small number of node-negative patients was analyzed, our results suggest that 20q13 amplification might have independent role as a prognostic indicator. Studies to address this question in large patient materials are warranted. Moreover, based on these survival correlations, the currently unknown, putative oncogene amplified in this locus may confer an aggressive phenotype. Thus, cloning of this gene is an important goal. Based on the association of amplification with highly proliferative tumors one could hypothesize a role for this gene in the growth regulation of the cell.

The role of the low-level 20q13 amplification as a significant event in tumor progression appears less clear. Low-level amplification was defined as 1.5-3-fold increased average copy number of the 20q13 probe relative to the p-arm control. In addition, these tumors characteristically lacked individual tumor cells with very high copy numbers, and showed a scattered, not clustered, appearance of the signals. Accurate distinction between high and low level 20q13 amplification can only be reliably done by FISH, whereas Southern and slot blot analyses are likely to be able to detect only high-level amplification, in which substantial elevation of the average gene copy number takes place. This distinction is important, because only the high amplified tumors were associated with adverse clinical outcome. Tumors with low-level 20q13 amplification appeared to have many clinicopathological features that were in between of those found for tumors with no and those with high level amplification. For example, the average tumor S-phase fraction was lowest in the non-amplified tumors and highest in the highly amplified tumors. One possibility is that low-level amplification precedes the development of high level amplification. This has been shown to be the case, e.g., in the development of drug resistance-gene amplification in vitro (Stark, Adv. Canc. Res., 61: 87-113 (1993)). Evidence supporting this hypothesis was found in one of our patients, whose local metastasis contained a much higher level of 20q13 amplification than the primary tumor operated 8 months earlier.

Finally, our previous paper reported a 1.5 Mb critical region defined by RMC20C001 probe and exclusion of candidate genes in breast cancer cell lines and in a limited number of primary breast tumors. Results of the present study confirm these findings by showing conclusively in a larger set of primary tumors that the critical region of amplification is indeed defined by this probe.

The present data thus suggest that the high-level 20q13 amplification may be a significant step in the progression of certain breast tumors to a more malignant phenotype. The clinical and prognostic implications of 20q13 amplification are striking and location of the minimal region of amplification at 20q13 has now been defined.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference for all purposes.

Discussion of the Accompanying Sequence Listing

SEQ ID NOs:1-10, 12, and 45 provide nucleic acid sequences. In each case, the information is presented as a DNA sequence. One of skill will readily understand that the sequence also describes the corresponding RNA (i.e., by substitution of the T residues with U residues) and a variety of conservatively modified variations thereof. The complementary sequence is fully described by comparison to the existing sequence, i.e., the complementary sequence is obtained by using standard base pairing rules for DNA (e.g., A to T, C to G). In addition, the nucleic acid sequence provides the corresponding amino acid sequence by translating the given DNA sequence using the genetic code.

For SEQ ID NO: 11, the information is presented as a polypeptide sequence. One of skill will readily understand that the sequence also describes all of the corresponding RNA and DNA sequences which encode the polypeptide, by conversion of the amino acid sequence into the corresponding nucleotide sequence using the genetic code, by alternately assigning each possible codon in each possible codon position. Similarly, each nucleic acid sequence which is provided also inherently provides all of the nucleic acids which encode the same protein, since one of skill simply translates a selected nucleic acid into a protein and then uses the genetic code to reverse translate all possible nucleic acids from the amino acid sequence.

The sequences also provide a variety of conservatively modified variations by substituting appropriate residues with the exemplar conservative amino acid substitutions provided, e.g., in the Definitions section above.

---

SEQUENCE LISTING

SEQ. ID. No. 1
3bf4 3000 bp
CCGCCGGCCGGGGCGCCTGGCTGCACTCAGCGCCGGAGCCGGGAGCTAGCGGCCGCCGCCATGTCCCACCAGAC
CGGCATCCAAGCAAGTGAAGATGTTAAAGAGATCTTTGCCAGAGCCAGAAATGGAAAGTACAGACTTCTGAAAA
TATCTATTGAAAATGAGCAACTTGTGATTGGATCATATAGTCAGCCTTCAGATTCCTGGGATAAGGATTATGAT
TCCTTTGTTTTACCCCTGTTGGAGGACAAACAACCATGCTATATATTATTCAGGTTAGATTCTCAGAATGCCCA
GGGATATGAATGGATATTCATTGCATGGTCTCCAGATCATTCTCATGTTCGTCAAAAAATGTTGTATGCAGCAA

SEQUENCE LISTING

```
CAAGAGCAACTCTGAAGAAGGAATTTGGAGGTGCCACATTAAAGATGAAGTATTTGGAACAGTAAAGGAAGAT
GTATCATTACATGGATATAAAAAATACTTGCTGTCACAATCTTCCCCTGCCCCACTGACTGCAGCTGAGGAAGA
ACTACGACAGATTAAAATCAATGAGGTACAGACTGACGTGGGTGTGGACACTAAGCATCAAACACTACAAGGAG
TAGCATTTCCCATTTCTCGAGAAGCCTTTCAGGCTTTGGAAAAATTGAATAATAGACAGCTCAACTATGTGCAG
TTGGAAATAGATATAAAAAATGAAATTATAATTTTGGCCAACACAACAAATACAGAACTGAAAGATTTGCCAAA
GAGGATTCCCAAGGATTCAGCTCGTTACCATTTCTTTCTGTATAAACATTCCCATGAAGGAGACTATTTAGAGT
CCATAGTTTTTATTTATTCAATGCCTGGATACACATGCAGTATAAGAGAGCGGATGCTGTATTCTAGCTGCAAG
AGCCGTCTGCTAGAAATTGTAGAAAGACAACTACAAATGGATGTAATTAGAAAGATCGAGATAGACAATGGGGA
TGAGTTGACTGCAGACTTCCTTTATGAAGAAGTACATCCCAAGCAGCATGCACACAAGCAAAGTTTTGCAAAAC
CAAAAGGTCCTGCAGGAAAAAGAGGAATTCGAAGACTAATTAGGGGCCCAGCGGAAACTGAAGCTACTACTGAT
TAAAGTCATCACATTAAACATTGTAATACTAGTTTTTTAAAAGTCCAGCTTTTAGTACAGGAGAACTGAAATCA
TTCCATGTTGATATAAAGTAGGGAAAAAAATTGTACTTTTTGGAAAATAGCACTTTTCACTTCTGTGTGTTTTT
AAAATTAATGTTATAGAAGACTCATGATTTCTATTTTTGAGTTAAAGCTAGAAAAGGGTTCAACATAATGTTTA
ATTTTGTCACACTGTTTTCATAGCGTTGATTCCACACTTCAAATACTTCTTAAAATTTTATACAGTTGGGCCAG
TTCTAGAAAGTCTGATGTCTCAAAGGGTAAACTTACTACTTTCTTGTGGGACAGAAGACCTTAAAATATTCAT
ATTACTTAATGAATATGTTAAGGACCAGGCTAGAGTATTTTCTAAGCTGGAAACTTAGTGTGCCTTGGAAAAGC
CGCAAGTTGCTTACTCCGAGTAGCTGTGCTAGCTCTGTCAGACTGTAGGATCATGTCTGCAACTTTTAGAAATA
GTGCTTTATATTGCAGCAGTCTTTTATATTTGACTTTTTTTAATAGCATTAAAATTGCAGATCAGCTCACTCT
GAAACTTTAAGGGTACCAGATATTTTCTATACTGCAGGATTTCTGATGACATTGAAAGACTTTAAACAGCCTTA
GTAAATTATCTTTCTAATGCTCTGTGAGGCCAAACATTTATGTTCAGATTGAAATTTAAATTAATATCATTCAA
AAGGAAACAAAAAATGTTGAGTTTTAAAAATCAGGATTGACTTTTTTCTCCAAAACCATACATTTATGGGCAAA
TTGTGTTCTTTATCACTTCCGAGCAAATACTCAGATTTAAAATTACTTTAAAGTCCTGGTACTTAACAGGCTAA
CGTAGATAAACACCTTAATAATCTCAGTTAATACTGTATTTCAAAACACATTTAACTGTTTTCTAATGCTTTGC
ATTATCAGTTACAACCTAGAGAGATTTTGAGCCTCATATTTCTTTGATACTTGAAATAGAGGGAGCTAGAACAC
TTAATGTTTAATCTGTTAAACCTGCTGCAAGAGCCATAACTTTGAGGCATTTTCTAAATGAACTGTGGGGATCC
AGGATTTGTAATTTCTTGATCTAAACTTTATGCTGCATAAATCACTTATCGGAAATGCACATTTCATAGTGTGA
AGCACTCATTTCTAAACCTTATTATCTAAGGTAATATATGCACCTTTCAGAAATTTGTGTTCGAGTAAGTAAAG
CATATTAGAATAATTGTGGGTTGACAGATTTTTAAAATAGAATTTAGAGTATTTGGGGTTTTGTTTGTTTACAA
ATAATCAGACTATAATATTTAAACATGCAAATAACTGACAATAATGTTGCACTTGTTTACTAAAGATATAAGT
TGTTCCATGGGTGTACACGTAGACAGACACACATACACCCAAATTATTGCATTAAGAATCCTGGAGCAGACCAT
AGCTGAAGCTGTTATTTTCAGTCAGGAAGACTACCTGTCATGAAGGTATAAAATAATTTAGAAGTGAATGTTTT
TCTGTACCATCTATGTGCAATTATACTCTAAATTCCACTACACTACATTAAAGTAAATGGACATTCCAGAATAT
AGATGTGATTATAGTCTTAAACTAATTATTATTAAACCAATGATTGCTGAAAATCAGTGATGCATTTGTTATAG
AGTATAACTCATCGTTTACAGTATGTTTTAGTTGGCAGTATCATACCTAGATGGTGAATAACATATTCCCAGTA
AATTTATATAGCAGTGAAGAATTACATGCCTTCTGGTGGACATTTTATAAGTGCATTTTATATCACAATAAAA
TTTTTTCTCTTTAAAAAAAAAAAACAAGAAAAAAAAAAA

SEQ. ID. No. 2
1b11 723 bp
TGGAAGCTGTCATGGTTACCGTCTCTAACGTTGGACTCTTAAGAAAATGATTATTCCTGGTTTCTAGACAGGCC
AAATGTAATTCACCTACGTGGCAGATTAAAGAGGTGGGCTTACTAGATTTGATTGGGTATTGAGCATGCTCTGA
ATGACAGTCCCCAAAAGGACCTCTTATCCGTTCTTCCCCTTGGGGAAGGGCTTTTGCCACTTCCATGTCAATG
TGGCAGTTGAGCTTGGAAATTGGTGCGTTGTACAACATAAGCATTACTTCTCCAAGATGTGCCTGTGTAGAAAT
GGTCATAGATTCAAAACTGTAGCTACTATGTGGACAGGGGGGCAGCAAGGACCCCACTTTGTAAAACATGTTTT
GGGGGAATGTTTTGTTTTTCATTTTCTTATTACCTGGCAAAATAATCCAGGTGGTGTGTGAGTCACCAGTAGAG
ATTATAAAGTCCAAGGAAGTAGAATCAGCCTTACAAACAGTGGACCTCAACGAAGGAGATGCTGCACCTGAACC
CACWGAAGCGAAACTCAAAAGAGAAGAAAGCAAACCAAGAACCTCTCTGATGRCGTTTCTCAGACAAATGGTAA
GCCCCTTACTTCCAGTATAGGAAACCTAAGATACCTAGAGCGGCTTTTGGGAACAATGGGCTCATGCCACAGGT
AGTAGGAGACATAATTGTAGCTGGTGTGTATGGAATGTGAATGGAATATGGATTGCG

SEQ. ID. No. 3
cc49 1507 bp
GCAGGTTGCTGGGATTGACTTCTTGCTCAATTGAAACACTCATTCAATGGAGACAAAGAGCACTAATGCTTTGT
GCTGATTCATATTTGAATCGAGGCATTGGGAACCCTGTATGCCTTGTTTGTGGAAAGAACCAGTGACACCATCA
CTGAGCTTCCTAAAAGTTCGAAGAAGTTAGAGGACTATACACTTTCTTTTGAACTTTTATAATAAATATTTGCT
CTGGTTTTGGAACCCAGGACTGTTAGAGGGTGAGTGACAGGTCTTACAGTGGCCTTAATCCAACTCCAGAAATT
GCCCAACGGAACTTTGAGATTATATGCAATCGAAAGTGACAGGAAACATGCCAACTCAATCCCTCTTAATGTAC
ATGGATGGCCAAGAGTGATTGGCAGCTCTCTTGCCAGTCCGATGGAGATGGAGATGCCTTGTCAATGAAAGGGC
CCNCTGTTGTCAATTCCGAGCTACACAAAGAAAAAATGTCAATCCGAATCGAGGGGAATATGCCCTTGGATTG
CATGTTCTGCAGCCAGACCTTCACACATTCAGAAGACCTTAATAAACATGTCTTAATGCAACACCGGCCTACCC
TCTGTGAACCAGCAGTTCTTCGGGTTGAAGCAGAGTATCTCAGTCCGCTTGATAAAAGTCAAGTGCGAACAGAA
CCTCCCAAGGAAAAGAATTGCAAGGAAAATGAATTTAGCTGTGAGGTATGTGGGCAGACATTTAGAGTCGCTTT
TGATGTTGAGATCCACATGAGAACACACAAAGATTCTTTCACTTACGGGTGTAACATGTGCGGAAGAAGATTCA
AGGAGCCTTGGTTTCTTAAAAATCACATGCGGACRCATAATGGCAAATCGGGGGCCAGAAGCAAACTGCAGCAA
GGCTTGGAGAGTAGTCCAGCAACGATCAACGAGGTCGTCCAGGTGCACGCGGCCGAGAGCATCTCCTCTCCTTG
CAAAATCTGCATGGTTTGTGGCTTCCTATTTCCAAATAAAGAAAGTCTAATTGAGCACCGCAAGGTGCACACCA
AAAAAACTGCTTTCGGTACCAGCAGCGCGCAGACAGACTCTCCACAAGGAGGAATGCCGTCCTCGAGGGAGGAC
TTCCTGCAGTTGTTCAACTTGAGACCAAAATCTCACCCTGAAACGGGGAAGAAGCCTGTCAGATGCATCCCTCA
GCTCGATCCGTTCACCACCTTCCAGGCTTGGCAKCTGGCTACCAAAGGAAWAGTTGCCATTTGCCAAGAAGTGA
AGGAATTGGGGCAAGAAGGGAGCACCGACAACGACGATTCGAGTTCCGAGAGGAGCTTGGAGAAACAAATAAG
AACCATTGTGCAGGCCTCTCGCAAGAGAAAGAGAAGTGCAAACACTCCCACGGCGAAGCGCCCTCCGTGGACGC
GGATCCCAAGTTACCCAGTAGCAAGGAGAAGCCCACTCACTGCTCCGAGTGCGGCAAAGCTTTCAGAACCTACC
ACCAGCTGGTCTTGCACTCCAGGGTCC
```

SEQUENCE LISTING

SEQ. ID. No. 4
cc43 2605 bp
CAAGCTCGAAATTAACCCTCACTAAAGGGAACAAAAGCTGGAGCTCCACCGCGGTGGCGCCCGCTCTAGAACTA
GTGGATCCCCCGGGCTGCAGGAATTCGGCACGAGCTGGGCTACTACGATGGCGATGAGTTTCGAGTGGCCGTGG
CAGTATCGCTTCCCACCCTTCTTTACGTTACAACCGAATGTGGACACTCGGCAGAAGCAGCTGGCCGCCTGGTG
CTCGCTGGTCCTGTCCTTCTGCCGCCTGCACAAACAGTCCAGCATGACGGTGATGGAAGCTCAGGAGAGCCCGC
TCTTCAACAACGTCAAGCTACAGCGAAAGCTTCCTGTGGAGTCGATCCAGATTGTATTAGAGGAACTGAGGAAG
AAAGGGAACCTCGAGTGGTTGGATAAGAGCAAGTCCAGCTTCCTGATCATGTGGCGGAGGCCAGAAGAATGGGG
GAAACTCATCTATCAGTGGGTTTCCAGGAGTGGCCAGAACAACTCCGTCTTTACCCTGTATGAACTGACTAATG
GGGAAGACACAGAGGATGAGGAGTTCCACGGGCTGGATGAAGCCACTCTACTGCGGGCTCTGCAGGCCCTACAG
CAGGAGCACAAGGCCGAGATCATCACTGTCAGCGATGGCCGAGGCGTCAAGTTCTTCTAGCAGGGACCTGTCTC
CCTTTACTTCTTACCTCCCACCTTTCCAGGGCTTTCAAAAGGAGACAGACCCAGTGTCCCCAAAGACTGGATC
TGTGACTCCACCAGACTCAAAAGGACTCCAGTCCTGAAGGCTGGGACCTGGGGATGGGTTTCTCACACCCCATA
TGTCTGTCCCTTGGATAGGGTGAGGCTGAAGCACCAGGGAGAAAATATGTGCTTCTTCTCGCCCTACCTCCTTT
CCCATCCTAGACTGTCCTTGAGCCAGGGTCTGTAAACCTGACACTTTATATGTGTTCACACATGTAAGTACATA
CACACATGCGCCTGCAGCACATGCTTCTGTCTCCTCCTCCTCCCACCCCTTTAGCTGCTGTTGCCTCCCTTCTC
AGGCTGGTGCTGGATCCTTCCTAGGGGATGGGGAAGCCCTGGCTGCAGGCAGCCTTCCAGGCAATATGAAGAT
AGGAGGCCCACGGGCCTGGCAGTGAGAGGTGTGGCCCCACACCGATTTATGATATTAAAATCTCAACTCCCAAA
AAAAAAAAAAAAAAACTGAGACTAGTTCTCTCTCTCTCGAGAACTAGTCTCGAGTTTTTTTTTTTTTTTTTT
TTTTTTTTTTTTTTTTTTTTTGGCTTTAAGGATTTATTTATTGTTTCCTCTTTACAGTGTCCACTTTTCTCTAC
TTAATACTACTTTCCAGTCTCAGAAGCCCAGAGGGAAAAAAAAAAGACCATGAATCTTCCTCTCCCAGATTAAA
GTACACACTTTGGAAAACAGATTGAAAACCTTTCTGAAAAAAGTTGACTGAAACTCCAAACCAACATGCCATA
TTGTTGATGTTGCTCATGAAATTGTTAAAAACCTGTTCTAGATAAAGAACAGTCTCAAGTTTTTGTACAGCCT
ACACATAGTACAAGGGTCCCCTATGATGATTCTTCTGTAGGACGAAATAATGTAATTTTTTCAGTTTCTGGTTT
ATAACTCTCTCGATCTCAGAGTTGACTGATTAAAACACCTACTCATGCAACAGAGAATAAAGCACTCATATTTT
TATAAATTATATGGACCAAACTATTTTGGAAATCTTATCTATTGGAGACACAATATGCTGGACTAAAGCAATAA
TTATTTTATTCTCAATGTCTGTGCTAACCTCAATGACTTAGAATGCTTTGCTATATTTTGCCTCTATGCCTCAA
CCACACTGGCTTTCTTTTAGCTCTTGAACAAGCCA
AACTGCTTCCTGCCTCAGGACCAGATATTTTGGGACTTCTCTTAAGAATTCTATTTCCTTAATTCTTTATCTGG
GTAACTTAGTTTTATCCAACACTTCAGATCCTGCCGTAAAAACTCTTCTTATAGAAGCCTGTCATGACACTGTC
TCTCTTCTCCAACATACTCACCAGCACACATGTAGACTAGATTAGAACCTCCTGTTTTTCTTTTTCATACTTTT
CTCTATCATGCTTCCCTCCATTATAATATTTTTATTATGTGTGTGAATGTCTGCCCCAAGTCAGTTTCCTCACT
AAACTATAAACTCCGTAAAGCTGGGATCCTTCCAATTTTGATCACCCACTTAGTACAGTAGGAACACAGTAAAGA
TTCAATTGGTATTTGTGGAATGAATGAATGAATTGTTTGCTAGTAAAGTCTGGGGGAACCCAGGTGAGAAGAG
CCTAGAAAGCAGGTCGAATCCAAGGCTAGAATAGACTTAGTGTTACTCAAGAAAGGGTAGCCTGAAAATAAAGGT
TCAAATTATAGTCAAGAATAGTCAAGACATGGGCAAGACAAGAGTGCTGCTCGTGCCGAATTCGATATCAAGCT
TATCGATACCGTCGACCTCGAGGGGGGGCCCGGTACCCAATTCGCCCTATAGTGAGTCGTATTACAATTCACTG
GCCGTCGTTTTACAACGTCGTGACTGGGAAAACCCTGGCGTTACCCAACTTAAT

SEQ. ID. No. 5
41.1 1288 bp
GAGGGCAGCGAGAAGGAGAAACCCCAGCCCCTGGAGCCCACATCTGCTCTGAGCAATGGGTGCGCCCTCGCCAA
CCACGCCCCGGCCCTGCCATGCATCAACCCACTCAGCGCCCTGCAGTCCGTCCTGAACAATCACTTGGGCAAAG
CCACGGAGCCCTTGCGCTCACCTTCCTGCTCCAGCCCAAGTTCAAGCACAATTTCCATGTTCCACAAGTCGAAT
CTCAATGTCATGGACAAGCCGGTCTTGAGTCCTGCCTCCACAAGGTCAGCCAGCGTGTCCAGGCGCTACCTGTT
TGAGAACAGCGATCAGCCCATTGACCTGACCAAGTCCAAAAGCAAGAAAGCCGAGTCCTCGCAAGCACAATCTT
GTATGTCCCCACCTCAGAAGCACGCTCTGTCTGACATCGCCGACATGGTCAAAGTCCTCCCCAAAGCCACCACC
CCAAAGCCAGCCTCCTCCTCCAGGGTCCCCCCATGAAGCTGGAAATGGATGTCAGGCGCTTTGAGGATGTCTC
CAGTGAAGTCTCAACTTTGCATAAAAGAAAAGGCCGGCAGTCCAACTGGAATCCTCAGCATCTTCTGATTCTAC
AAGCCCAGTTTGCCTCGAGCCTCTTCCAGACATCAGAGGGCAAATACCTGCTGTCTGATCTGGGCCCACAAGAG
CGTATGCAAATCTCTAAGTTTACGGGACTCTCAATGACCACTATCAGTCACTGGCTGGCCAACGTCAAGTACCA
GCTTAGGAAAACGGGCGGGACAAAATTTCTGAAAAACATGGACAAAAGGCCACCCCATCTTTTATTGCAGTGACT
GTGCCTCCCAGTTCAGAACCCCTTCTACCTACATCAGTCACTTAGAATCTCACCTGGGTTTCCAAATGAAGGAC
ATGACCCGCTTGTCAGTGGACCAGCAAAGCAAGGTGGAGCAAGAGATCTCCCGGGTATCGTCGGCTCAGAGGTC
TCCAGAAACAATAGCTGCCGAAGAGGACACAGACTCTAAATTCAAGTGTAAGTTGTGCTGTCGGACATTTGTGA
GCAAACATGCGGTAAAACTCCACCTAAGCAAAACGCACAGCAAGTCACCCGACACCATTCACAGTTTGTAACA
GACGTGATGAAGAATAGCTCTGCAGGACGAATGCCTTAGTTTCCACTTTCCAGCCTGGATCCCCTCACACTGA
ACCCTTCTTCGTTGCACCATCCTGCTTCTGACATTGAACTCATTGAACTCCTCCTGACACCCTGGCTCTGAGAA
GACTGCCAAAAAAAAAAAAAAAAAAAATTC

SEQ. ID. No. 6
GCAP 2820 bp
ATCCTAAGACGCACAGCCTGGGAAGCCAGCACTGGGGAAGTGGTGCTGAGGGATGTGGGTCACTGGGGTGAAGG
TGGAGCTTTCAGGGTCTCCCGTCAATGCAGCTGAGTTTTCTTTGGCAGGGAATTTACCAGCTGAAGAAAGCCTG
CCGGCGAGAGCTACAAACTGAGCAAGGCCAGCTGCTCACACCCAGGAGGACAGGATCTTCCTCCTGG
TGGATGAGAATGGAGATGGTAAGAGGGGCAGAGATGGGGAGAGTGCTGTCCACTCTGCATCATCGCCACTTTCT
GGCCGCACGTCCTTGGGCAAGGCCCTCCACCTTCCAACCCTGGGGTCCTCATCTGTGAGAAGGCTGTGGAGAAG
ATGTCATGAACTAACAAAGGGACTCATGAGCACGTGTTTGTAGGAGTGACTAAAAGTCCTACAGGAGTTGCTGA
TGGAGGCCAGGCACGCAGAATAGAAAGAATAGGAACTTTGGAGTCAGGCAGGGAGTGATATATTGAGCTTCTCG
TCCTAGTCTCAATTTCCTCATCTGGAAAATGGGGATAATAATAGTGGTTGAGAGGAATGAAATAGGATAATGTGT
TTAAGAGCAGGCATAGGGTAGACCTCCATTCAGGCTGCTTGGGCTTTCCTCCCTGTAGCCCAAAGCCCAGCCTC
AGGGCTATGTGGGAGAGAGCTGGCTTGGAATACACACTTGAGCCCTCCAGCTCTCAGCTCCACCCAGCATT
TCCGTGGTACCATGCGCAAAAGTAAAACTTCAATTCATCAGCAAAGAAAGCCCCTTAAAGGTGGCAGGAGACTC
CTGGAGATTCAGACACCTGACAAGCCGCAAGCTTGAGGTCTGAGACTGCAGGATAGTTGGCATAAGACGTGTAG
GCGCATCCTGGGAGCGAGGTCTCTCCTCCTGCCCCCAGACCCAGGTCTCCCCTTCTTCTACATGACCACCTCTC
CTCCCCCTTGCTCAGGCCAGCTGTCTCTGAACGAGTTTGTTGAAGGTGCCCGTCGGGACAAGTGGGTGATGAAG

```
ATGCTGCAGATGGACATGAATCCCAGCAGCTGGCTCGCTCAGCAGAGACGGAAAAGTGCCATGTTCTGAGGAGT
CTGGGGCCCCTCCACGACTCCAGGCTCACCCAGGTTTCCAGGGTAGTAGGAGGGTCCCCTGGCTCAGCCTGCTC
ATGCCCACTCTTCCCCTGGTGTTGACTTCCTGGCACCCCTGTGCAGGGCTGAGTGGGGATGGGGAAGGGCTGC
TGGGTTTGAAGTGGCCAACAGGGCATAGTCCATTTTGGAGGAGTCCCTGGGATGGTGAAGGGAATTCAGTTACT
TTTCCTGTTCAGCCGCTCCTGGGAGGACTGTGCCTTGGCTGGGTGGTTGTGGGGCTCCCACAGTTTCTGGGTGT
TCTCAGTTGGAAGCAAGAGCCAACTGAGGGGTGAGGGTCCCACAGACCAAATCAGAAATGAGAACACAAAGACT
GGTAGGAGGCAGGGGTGGGAGGGTGTTGAGACTGAAGAAAAGGCAGGAGTTGCCGGGCACGGTGGCTCACGCCT
GTAATCCCAGCACTTTGGGAGGCCGAGGCGGGCAGATCACGAGGTCAGGAGATCGAGACCATCCTGGCTAACAC
GGGGTGAAACCCCGTCTCTACTAAAAATACAAAAAATCAGCCGGGTGAGGTGGCGGGCGCCTGTAGTCCCAGCT
ACTCAGGAGGCTGAGGCAAGAGAATGGCGTGAACCCCAGGGGGCCGAGCCTACAGTGAGCCGAGATTGCGCCAC
TGCACTCCAGCCTGGACGACAGTGAGACTCCGTCTCAAAAAAAAAAAAGAAAGAAAAAGAAAAGGCAGGAGTTT
TGGGGGGCAGGGGGCAGCAATAATTCTATAACTTCCGGGATGCTGAGGGGCGTTCATGGGGAGGACCCTGGCCT
CCTCCTCCCCAAGGCATCCTCACCAGTGGTGTCAACAGGAAAATGGCAGCAAATACGCTGCAGGCTGTGGTCT
TTCTGCCTTTGAAAGGGTCAGCTGTACTTAAAGGGACTGTTTCAGCTCTGCCTGGGTGCTGCTCTGGGACCCCC
TGCTGCCAACCCACCACTCCCCCAACAATCCTCTCTTTCCATCCATATCCCCCAGTATGGACCTTCCACAACTC
CCAGCCATAAGCTGAATGTTTCTCTTTAAAGGATGGAGAAAACTTCTGTCTGTCTGGCAAGAATTGGGGGAC
TGTTGACTGGGATTGTGGGCTGGGCTTGGCTTCTAACTGCTGTGTGACCCAAGCAGCCACTTCTCCTCCCTAA
CCTTGGTTATGTCTTGGCAGCACAGTGAGCAGGTCGGACTAGGCGAACAGTTTTGGATTATTGTGTTTTTAGAT
GTGGAATTATTTTTTGTTATATAAACTCTTATGTGTAACCCCAATATAGAAACTAGATTAAAAGGGAGTCTCTC
TGGTTGAAAGGGGAGCTGAGTACCCTCTGGAACTGGAGGCACCTCTGAAAAAAGCAAACTGAAAACCAGTGCCC
TGGGTCACTGTTACTCCTATAAGACAGTTTAAAGTGAGACCTGGAAAAACATTTGCTTTACCTTGAATAGATAG
GTTTTTATGTTGGTATATAAGAAATAAAACTAACCTATTAACCCTGAGACTTTACAGGTGTGTTATTTCATATG
ATAGTCATATAAATTTCCTTTAGACATCAATTTTAGGTAAAAAATAATTGATTAGAAAATATTGGCCAGGTG
CAGCAGCTCACACCTGCAATCCCAGGACTTTGGGAGGCCGAGGCGGGTGGATCACCTGAGGTCAGGGGTTCAAG
ACCAGCCTG

SEQ. ID. No. 7
1b4 1205 bp
GCGCGCGTGAGTCCGCCCCCCCAGTCACGTGACCGCTGACTCGGGGCGTTCTCCACTATCGCTTACCTACCTCC
CTCTGCAGGAACCCGGCGATATGGCTGCCGCTGTGCCCCGCGCCGCATTTCTCTCCCCGCTGCTTCCCTTCTCC
TGGGCTTCCTGCTCCTCTCCGCTCCGCATGGCGGCAGCGGCCTGCACACCAAGGCGCCCTTCCCCTGGATACGG
TCACTTTCTACAAGGTCATTCCCAAAAGCAAGTTCGTCTGGTGAAGTTCGACACCCAGTACCCCTACGGTGAGA
AGCAGGATGAGTTCAAGCGTCTTCTGAAAACTCGGCTTCCAGCGATGATCTCTTGGTGGCAGAGGTGGGGATCT
CAGATTATGTGACAAGCTGAACATGGAGCTGAGTGAGAAATACAAGCTGGACAAAGAGAGCTACCCATCTTCTA
CCTCTTCCGGGATGGGGACTTTGAGAACCCAGTCCCATACACTGGGGCAGTTAGGTTGGAGCCATCCAGCGCTG
GCTGAAGGGGCAAGGGGTCTACCTAGGTATGCCTGGTGCCTGCCTGTATACGACGCCCTGGCCGGGGAGTTCAT
CAGGGCCTCTGGTGTGGAGGCCGCCAGGCCCTCTTGAAGCAGGGGCAAGATAACCTCTCAAGTGTGAAGGAGAC
TCAGAAGAGTGGGCCGAGCAATACCTGAAGATCATGGGGAAGATCTTAGACCAAGGGGAGCACTTCCAGCATCA
GAGATGACACGGATCGCCAGGCTGATTGAGAAGAACAAGATGAGTGACGGCAGAAGGAGGAGCTCCAGAAGAGC
TTAAACATCCTGACTGCCTTCCAGAAGAAGGGGGCCGAGAAAGAGGAGCTGTAAAAAGGCTGTCTGTGATTTTC
CAGGGTTTGGTGGGGGTAGGGAGGGGANAGTTAACCTGCTGGCTGTGANTCCCTTGTGGAATATAAGGGGGYMS
KGGGAAAAGWGGTACTAACCCACGATTCTGAGCCCTGAGTATGCCTGGACATTGATGCTAACATGACCATGCTT
GGGATGTCTCTAGCTGGTCTGGGGATAGCTGGAGCACTTACTCAGGTGGCTGGTGAAATGACACCTCAGAAGGA
ATGAGTGCTATAGAGAGGAGAGGAGTGTACTGCCCAGGTCTTTGACAGATGTAATTCTCATTCAATTAAAGT
TTCAGTGTTTTGGTTAAGTGG

SEQ. ID. No. 8
20sa7 456 bp
GAAATCAGAAGTTTAATATGACACAATTAAATATATTTGTATATCTCACACCGGAGNTTCTCTTCAAACATAAG
GAGTTAGAAATTACAAGTAGGCATATGCTTCCTATATTCAGATAAATTCATTTCGATTAATTAAATTCCAGATA
GAGAGAAGTAATTTTCGGAAAAGAAATGATAGCTATATTAAAGCAGATATTCATTACAATACCATGTAGAGACA
TAAGCAATATTTTGGCATCATTCTGTCCGCTCAGTAGGCCGTGTTCCCTCTGGTAGGGCCTTTGGAGAGTACCA
TCTATCTAAGATGGAGGAATGCTGTGGGAAGGGCGGGATGGAGGTGCGTTTTCTACGCTGAACCCCACACAGGA
AATCTGCAGCCCACACAGCTGCCTCTGCGCCGCCTTCCATGTGATCATCCTGGTCAATGAAGTGAATTGTCCTA
TTTCNGGGGGT

SEQ. ID. No. 9
Genomic Sequence Encoding ZABC1
CCATCATATTTCTTATTTTTTGGCGGAGAGGGGAGACTTGCTCTGTTGCCCAGGCTGGACCAGTGGTGCGATCT
TGGCTCACTGCAACCTCCACCTCCTGGGTTCAAGTGATTCCCAAATAGCTGGGATTACAGGTGTGTATTACCATGC
CCAGCTAATTTTGTATTTTTAGCAGATAAGGGGTTTCACCATGTTGGCCAGGCTGGTCTCCAACTCCTGGCCTCA
TGTGATCCACCCACTTCGGCTTCCCAAAGCATTGGGAGTATAGGTGTGAGCCACTATACCCGTCCTCCACATCATAT
TTCTAATCCCGAGACTGTAGAGCTGGTGTCTCTTTTTCTAAAGGATGTCAGTAGAGAAGTGGAGTTCCCCAAATT
ACAGTTTCACGTATTAGTCAAGTTTCTAAAATACAGTAATAATGTTGAGAGCTGACATAGGGACTAACTTGGTTTT
TTTTTTTTTTTTTTTTCAAATTCTCACTGAACTTTGATTTTGCTAAATAAGGACATTAAAAAAAAAAACCAAAA
AACTCCACTATTGCCTATTGCCACTATTTGATTTTTTAAAAAATAAGNCTATTTTAGCATCTAAAAGTAGGAAGGA
CCTCAAATAAATGAGTCTTTGTTCTTGGCCAGGGAAAACAGCTGTGTCAGAATTTGATAACTGTTTTTCTAGGGTA
TGTGCTGTTATTCAGTTAAAACCTTGCCTGGGACGCTAGCATTCAGTAAATACTTGTTGAATAAGCAAATGAAACT
TAAGCTTCTATGTATAGAAACCTAAGTCACTTCACATTCTGATTAGCAGAGTAATTGAATATTCTTTTCAATGTGT
AGCTCTATCCCCAGAACCACAGAATATTGGAACTGTAAAGGCCATCCTATAGTTTAACCAACTGCGTTAAATAGAT
AATAGAAGTGTGGTATGTGGCAGTGACAACTTGAAGGTTGTGACTAGAACTCGGGTCTCTGGAGTGTTCTATTA
TATCACACCAAGCTGGTCACCAGCCCATGTGTTGATCCTCCATTGTGATAGCAACAAAGAAAAGACTTCAGGACAT
TCTTTCCTTTACCCTAATCCTTGATCTGCAGTCTTATTTAGAAAAGCTTAATGTTAAAGATCTAGTTTATTCAAAA
CTAAAGATAACAAGGAGTATGAGAATTTCTATTTCGGAGTGTAAAGGAGGAGATGTTCCTTGGCTTCTCTGAGCC
TGCAGGCCTTCCTTGCTCTTTAAGGAAGTAGAGAGGGAGGAAAGTAAAGTATGCTTTTGTTTTTTAAGGTTACT
TTGCTGGGAGTAGTTTGCATGCCTTTTGGTTTTCTTGGGTGGAATTAACTGACTTAAGTTTTAAGTAGTTGGGACT
ATTTAAAAACAATGCCTATCCAATGTTTGCCATAAAGGCAGAGGGTATTGGCTTTAGAAGTTAATTCTTCTCCAGG
```

SEQUENCE LISTING

```
AGTGAAAATTAGCTTCTAAACCAGAAGCAGCAGAGCTAAATAAAGTAATTTTCCACCTGGCCAGTGCATGATGTGA
AAGGTAGATTAAAAAAATGAGAGGGCCCATTTTCTGATGAAAGACTAAGCCATGTTGAAACAGCCCTGTTGAGGAT
TTTATTTTAAATCTATACATTCACAAAGGAGCTTTGTGTATGTCTTTCCCTATTTGTTGTTTGGACTAGGAAGCCC
CACCCAGTGCTTGTTGAAGGCAGAAAGTCGTTGAAAGCAAGCTGGGATTTGAACAGTGGATTGAGGTTTCGAATAT
CCAGTGAACCAAATATATCAGGGTTCCCCTGGCCAAGATGAGTGACCATTCTGAGGTGTTAAGTATTTCTTGAAT
GGGGATTTTAGGAAAAGTTTCTGTATTTCTGTGCTCATTTTGTTGACCTCTGTATGTGCAAAATCTCTAAGGGGGT
GTTTGGGCACTTAGATTTCTTGGATGCAGATTTGTTTGTATATGAAACAAATTTTAAATTGTTTTGTATACACTGG
ATTTAAAATAGTTTACTAAAGTGTTTTAATTTTTTCATCTTAATTTTCACAGTTCTTATAGTCTTTAGATTTAGGG
AGGCTGTTGATGGCATCCACATGTGCATTTTAGTGGCATTTAAAATGTATTCAGCTGAATTTAACAATTTCTGACC
TAAAACTTGACATTTTAGATTTAAGTCGGTAAAGCACTGATTTAAACTGGATTTTAACTGGATGAAATTCTGATTT
AATAAGTGTACTGACTGGATAAAATGCCAATGATTTAATTAACAAGCACGTTTAACAGGATGCCCTATATATTAGT
TAAAAGTGAAGCAATTGAATTAGGTACCTTCTCTGCTGCGTGGAAAAGACCGTATGACTCACCCACACCAGCCTTC
TCTTCGCTCTGAGTGTAGCTAACCGTTTCTGTTTTTTTCCTCTAGGGTTTGGAAATCCCTTGTCTCCAGGTTGCT
GGGATTGACTTCTTGCTCAATTGAAACACTCATTCAATGGAGACAAAGAGAACTAATGCTTTGTGCTGATTCATAT
TTGAATCGAGGCATTGGGAACCCTGTATGCCTTGTTTGTGGAAAGAACCAGTGACACCATCACTGAGCTTCCTAAA
AGTTCGAAGAAGTTAGAGGACTATACACTTTCTTTTGAACTTTTATAATAAATATTTGCTCTGGTTTTTGGAACCC
AGGGCTGTTAGAGGGGTGAGTGACAAGTCTTACAAGTGGCCTTATTCCAACTCCAGAAATTGCCCAACGGAACTTT
GAGATTATATGCAATCGAAAGTGACAGGAAACATGCCAACTCAATCCCTCTTAATGTACATGGATGGGCAGAAGT
GATTGGCAGCTCTCTTGGCAGTCCGATGGAGATGGAGGATGCCTTGTCAATGAAAGGGACCGCTGTTGTTCCATTC
CGAGCTACACAAGAAAAAAATGTCATCCAAATCGAGGGGTATATGCCCTTGGATTGCATGTTCTGCAGCCAGACCT
TCACACATTCAGAAGACCTTAATAAACATGTCTTAATGCAACACCGGCCTACCCTCTGTGAACCAGCAGTTCTTCG
GGTTGAAGCAGAGTATCTCAGTCCGCTTGATAAAAGTCAAGTGCGAACAGAACCTCCCAAGGAAAAGAATTGCAAG
GAAAATGAATTTAGCTGTGAGGTATGTGGGCAGACATTTAGAGTCGCTTTTGATGTTGAGATCCACATGAGAACAC
ACAAAGATTCTTTCACTTACGGGTGTAACATGTGCGGAAGAAGATTCAAGGAGCCTTGGTTTCTTAAAAATCACAT
GCGGACACATAATGGCAAATCGGGGGCCAGAAGCAAACTGCAGCAAGGCTTGGAGAGTAGTCCAGCAACGATCAAC
GAGGTCGTCCAGGTGCACGCGGCCGAGAGCATCTCCTCTCCTTACAAAATCTGCATGGTTTGTGGCTTCCTATTTC
CAAATAAAGAAAGTCTAATTGAGCACCGCAAGGTGCACACCAAAAAAACTGCTTTCGGTACCAGCAGCGCGCAGAC
AGACTCTCCACAAGGAGGAATGCCGTCCTCGAGGGAGGACTTCCTGCAGTTGTTCAACTTGAGACCAAAATCTCAC
CCTGAAACGGGGAAGAAGCCTGTCAGATGCATCCCTCAGCTCGATCCGTTCACCACCTTCCAGGCTTGGCAGCTGG
CTACCAAAGGAAAAGTTGCCATTTGCCAAGAAGTGAAGGAATCGGGGCAAGAAGGGAGCACCGACAACGACGATTC
GAGTTCCGAGAAGGAGCTTGGAGAAACAAATAAGGGCAGTTGTGCAGGCCTCTCGCAAGAGAAAGAGAAGTGCAAA
CACTCCCACGGCGAAGCGCCCTCCGTGGACGCGGATCCCAAGTTACCCAGTAGCAAGGAGAAGCCCACTCACTGCT
CCGAGTGCGGCAAAGCTTTCAGAACCTACCACCAGCTGGTCTTGCACTCCAGGGTCCACAAGAAGGACCGGAGGGC
CGGCGCGGAGTCGCCCACCCATGTCTGTGGACGGGAGGCAGCCGGGGACGTGTTCTCCTGACCCTCGCCGCCCTCTG
GATGAAAATGGAGCCGTGGATCGAGGGGAAGGTGGTTCTGAAGACGGATCTGAGGATGGGCTTCCCGAAGGAATCC
ATCTGGGTAAGCTGCCCTGTCTCCGTCCCGTGCTGTTCCGCCTGTGTCTGTCTGTCTCCCCGTCTCCCCCTCTCTA
TTCCCATCTCCAGACAACGCTGGCCAGGAATGGGGTTTGGAGAGCCAGAGTCAAGTCCAGGCTCTTTTTGGTATCA
CTCTGTGTAAGTCATTTAACCTCTCAGGGCCTTAATTTTCTCATTTCTGTAATAACAGGGTTGAGTTAAGAGGTCT
CCTTGTTCTGAAAATATATATATATTTTTTAAACGTGTATCGTTTTGCTCACAAAACACACTTTAAAAAAAAAATA
ACTTGTGCATCCAGCCCAAATGCACTGCTTCTTAACTGGGGCGATTTTGTTCCCAATCAGTATCTGGCAATGTCTG
GAGGCATTTTGGTTGTCATACTGTGTGTGTGGGTGTGCCTGCTGGCATCCAGTGGGCAGAGGCCAGGGACACTGCT
CAGCATGGTACAGTGCACAGGACAGCCCCATCATCAAAGAATTATCTGGTCCCAAATGTCAATAGTTTGAGCATTG
AGAGACCCTAGCCTTCACTTAAGTTTTTCTGGCGTTCCTGATCTTTTTCTGTAGTGAATTTCTAGTGGCCATAAAA
GGTACTGGGAGTGATCAACTAGAGCCAGGAATATTATTTGGGCAGCCGTTTGGTGCTGTCCAAAACCTTGTCCTTT
CTGTCTGGCAAGCTAGTATCCATTTATAGGTACCTCAGGAACCCAAATGATTTGTCATAAAATACAAGGAATGTGA
GCACACTGAAGACATTTTTAAGAAGGCTCATTTGCTCAGCAGAATTTTCAGTGTACTAGTGGCATTTATAGAAAGA
GAAGGTGATCACTGAAGGCATGCTCACATAATATTCCTGAGCCCTGGTGGGCGTTATCTAGGGCAAAGGATTCCAC
CTGTGTTTGGAGTTGCGCCCATCCTCACTGTAGCCAGAGCTTCTCCTATCAGAGTTTAGTATTTTGTTTGAATAGA
GGATCTTGCTGCTTAAAACAGTTGAAAAGACCCTGATGGGCAGGCCGTAATTGACAAGCGAATGATGGGAACATGA
ATCGGTCTTAGGGAAGCATCTGTCAAAGTGGTCCTTGGTTAAAACAAGTGCCTCCTCCTCTCAGTGTCACTTGATT
GTGTGCTTGAATTCTTCGGAAAACTGGGTGTATGAGACCCACGATGAATTTGCCCACACGATTGATTGGACTCTTC
CTTCACCTGCTCTTCAGCCAGTGCCAGTTCCTTTTCTGATCATGTGATTGACGTGAGAACTGTAGTCTGTATATCA
AATCTTTAGAATGTTTTTGAGTTTCCTGGGACACAGGAAACCCAGCACTTAGCATACTACAAATCTAATGTCTTAA
TGGCATCATAAAAAGAGGCTTTAAACACAGACTCCAGTTAGCTAAGTGGTTTCTGCTAGTGCCGGTACTGTTGCAG
GGGCCCTGTGAGATGCCCCAGTTCCTGAAAGAAATGAAAAGGCCAGTTACCGGTAGGTGGTGTGGAAAACATGGG
CTAGATCATCAGGCAGGACAGAATGCCTGGCTGTGGGTGGGAGCACCCCAGCTTGGCGTTGAGTTCTGGTTCTACC
ACTGCGTTGTTTTGTGACCAATTATGAGTTGCTTAACCTTTCTTTGCTACTATTTCCCTGTTTGCAAAATGGTTCA
TTGACCCCTGTCTTCCACCTCCCAAGGACAATTTCAACAGCCTArrTGTAAAAAGATCACAGTCCTTTAAAAAATA
TAACTGTAAAGTCAGAGGTGATGCTTGAAAGAGCAGGAACCAGGTAGATGTGGAAATGTCATGTCCTTTGTTCTAA
AGAAAAGGCATTTCATAGCTTTTTGGATATGACGCAACATACCATAAATCCTGACACATAGTTGGGAGTCGGAAAT
TGCAACAACGCCCAGTTATAAACCCAGCTAGTTTGGGTATGATTGTAAGAAAAAAAGATCTGGCCATTCTGTATTTG
GGGAATTGATTTTCCTAAACTTATATTATCTTAGTAGTCTAGATTTATCATATTGTACTATCATCCTGGCTTTTTT
AAGACTTAAGAAGATCAAGTAAATTTTTTTTCTTTCTTTAGACACTATATAGATCATCAAGGGTGTCTGTCTTAC
AGGTGGATAGTGATATGATCTACAGTGAGGGGACATTTATTTAAAACTTAAACATTCATGTGTTTTGGGGGTGGTA
TTTTAACGGCAGCACCTCTGATTGTCTTTTGGAGGGCTGGTGTGTGTTTGAAGTTCTGTCCTCCTTCCAGTGGACT
CTAACTTCTCCTGATGCACGTGAGACACATTGTCCTATTGTCCTGCAGAAACTAAAGCCAAACACTGTCATCTGGG
GACAGGTTTTCATTTGTCAGATCTCTTTCGCCCACATGAGTGTTTGTGGACAATACAGCCTGCTTTCCAAAACTTT
GCTAAATTTTGACAGACTTTCCTAGGTGCTTGCCCAATGCCAGACTTTCTTTTCTGTTGAAGATTAAGTTGTGCTT
GCTGCCCTCTAGTGGTCAGTTGTTTAATCCTAACCTTAAACGGCTTATTTTTCCCCTGGTGGTTGGGAAGTTGACG
GTTTGTAATTGGCTCATTTTTCTAAATTATTCTGAAGAAGATAATTTTTCCCGCCAGTATGTATGTCCACCTTCAG
TTTGCCAGATCCTGCCTGCTCAGAGACACTGAGAACCGGAAGCTGCCCGGGCAATTCAGTCTATGAAATGATCTTT
CTTGTGATTAAGGCAAACGAAGAACTGAATGTTTAATAGTGTACTCTGCTGTACCCAGAAAAAAACAAAACAAAAT
CATGTTATAACACTCTAAAACTTCAAACAACCTCCAACAGCATTTGGTGTGTGTCTAGCCGTTTTGTTCAACCCG
ATGTTATATAAAAGAATTTTTTCATGCTTTCCAAAAATGTTTATGTCAAGAATATTTAAGTCAGCATGCCTTATTC
AGGTACTTCAGCTACCTTCTTATATAAATATTTTTGTTTTTCCTTTAAGATAAAAATGATGATGGAGGAAAAATAA
AACATCTTACATCTTCAAGAGAGTGTAGTTATTGTGGAAAGTTTTTCCGTTCAAATTATTACCTCAATATTCATCT
CAGAACGCATACAGGTAAAGAACTTTTATTTTTTTAACCATGCATTAGTTAAATTATGTAGTTATCTAATTTTTTT
```

GTTGTTGTTGTTCAGATACTCTGCCAGATCCTTGGACTAGCTTAAGGATAAATATGTAGCATGTTGATTGCAGTGG
TTATTTTTATTCTTTTAGTGCCATTGTAACTTGAGCCATTGTTCTTATTTGCAGTTCATTTCTTTTCTTTCTTTTT
TGTTTTTTGAGACGGAGTCTTGCTCTGTCACCTCGGCTGGAGTGCAGTGGTGCAATTTCGGCTCACTGCAGCCTCC
ACCTCCCTGGTTCAAGCAATACTCCTGCCTCAGCCTCCCCAGTAGTTGGGATTACAGGTACCTGCCACCACACCCG
GCTAATTTCTGTATTTTTAGTAGAGATGGGGTTTCACCATGCTGGCCAGGCTGGTTTCGAACTCCTGACCTCAAGT
GATCCGCTCACCTTGGCCTCCCATAGTGTTGGCCTCCCATAGTGCTGGGATTACAGGCGTGAGCCACCGCGCCCGG
ACAAAGTTCATTTGTTTAGTTTATGACTGCTATGTCCTGACTCTTATCTTATTAAAAGCTACAGTATTTTAAAATG
CTGCATCTTATGTCTTTATGATTGAGAATGAAATGAGAATCTATTTAGTAGTCTTGAGATTGTGAAAGGAGCTATG
ACATCATGATGTAGGAGCTGCGTAGATTTGAAATTTCATCTCTTCCACTTACTATCTGTGCACCCTTGGGCAAGT
TATTTAACCTTTTTGTGCTTTTAGTTTTCTTTGCTGTAAAAGTAGAATAATACATATTTCCCTAGGGCTGTTAGGA
AGATTAAATAAGTTAGAAGTGTTGCTGTTAATTTTTCTATTGAAGATAGGCATTCATAATTTCAAATATTCATTAC
AGTAAGGATGATAAAGAACTGATGAGAAATCCTATGTGATAGTAGATCGAGAAAGCAAAAGGAGGAAAGAAGCCTG
TTTTCTTAATAAATAGATATTTGATCTATTTCAGTGCTTTTCATACACTTCTATAATAAAGTGCCATTTCTTGCCT
TAGGTGAAAAACCATACAAATGTGAATTTTGTGAATATGCTGCAGCCCAGAAGACATCTCTGAGGTATCACTTGGA
GAGACATCACAAGGAAAAACAAACCGATGTTGCTGCTGAAGTCAAGAACGATGGTAAAAATCAGGACACTGAAGAT
GCACTATTAACCGCTGACAGTGCGCAAACCAAAAATTTGAAAAGATTTTTTGATGGTGCCAAAGATGTTACAGGCA
GTCCACCTGCAAAGCAGCTTAAGGAGATGCCTTCTGTTTTTCAGAATGTTCTGGGCAGCGCTGTCCTCTCACCAGC
ACACAAAGATACTCAGGATTTCCATAAAAATGCAGCTGATGACAGTGCTGATAAAGTGAATAAAAACCCTACCCCT
GCTTACCTGGACCTGTTAAAAAAGAGATCAGCAGTTGAAACTCAGGCAAATAACCTCATCTGTAGAACCAAGGCGG
ATGTTACTCCTCCTCCGGATGGCAGTACCACCCATAACCTTGAAGTTAGCCCCAAAGAGAAGCAAACGGAGACCGC
AGCTGACTGCAGATACAGGCCAAGTGTGGATTGTCACGAAAAACCTTTAAATTTATCCGTGGGGGCTCTTCACAAT
TGCCCGGCAATTTCTTTGAGTAAAAGTTTGATTCCAAGTATCACCTGTCCATTTTGTACCTTCAAGACATTTTATC
CAGAAGTTTTAATGATGCACCAGAGACTGGAGCATAAATACAATCCTGACGTTCATAAAAACTGTCGAAACAAGTC
CTTGCTTAGAAGTCGACGTACCGGATGCCCGCCAGCGTTGCTGGGAAAAGATGTGCCTCCCCTCCCTAGTTTCTGT
AAACCCAAGCCCAAGTCTGCTTTCCCGGCGCAGTCCAAATCCCTGCCATCTGCGAAGGGGAAGCAGAGCCCTCCTG
GGCCAGGCAAGGCCCCTCTGACTTCAGGGATAGACTCTAGCACTTTAGCCCCAAGTAACCTGAAGTCCCACAGACC
ACAGCAGAATGTGGGGGTCCAAGGGGCCGCCACCAGGCAACAGCAATCTGAGATGTTTCCTAAAACCAGTGTTTCC
CCTGCACCGGATAAGACAAAAAGACCCGAGACAAAATTGAAACCTCTTCCAGTAGCTCCTTCTCAGCCCACCCTCG
GCAGCAGTAACATCAATGGTTCCATCGACTACCCCGCCAAGAACGACAGCCCGTGGGCACCTCCGGGAAGACTA
TTTCTGTAATCGGAGTGCCAGCAATACTGCAGCAGAATTTGGTGAGCCCCTTCCAAAAGACTGAAGTCCAGCGTG
GTTGCCCTTGACGTTGACCAGCCCGGGGCCAATTACAGAAGAGGCTATGACCTTCCCAAGTACCATATGGTCAGAG
GCATCACATCACTGTTACCGCAGGACTGTGTGTATCCGTCGCAGGCGCTGCCTCTCCCAAACCAAGGTTCCTGAGCTC
CAGCGAGGTCGATTCTCCAAATGTGCTGACTGTTCAGAAGCCCTATGGTGGCTCCGGGCCACTTTACACTTGTGTG
CCTGCTGGTAGTCCAGCATCCAGCTCGACGTTAGAAGGTATTGCATGAGGGGCGTCGTGTTTAAATGGCTGCCTAC
AGTGATTAATAGCTAATCCAGGCATTCTCAGTGGAGATGGTACCACTCCCAAGGGTGGGGGGTAGGCAGCCAGAAG
TTCTTGGGGGTCACAGAGAGAAGCATTCTTAGATACGGCAGTGGTTTGTGGTCCTCCAAAGCCTTACTTAACTCTGT
GGGTTTAACTCTTAACCCTGTGTATTTTATTCTTTTGATTTGTTTAGTCTTACTTTATTTTTAGAGAAAGGGTCTT
GCTCCGTCATCTAGATTGGAGTGCAGCGGTGTAATCATAGCTTACTGTAGTCTTGAATTCCTGAGTTCAAGAGATC
CTTCTGCCTCAGCTTCCCAGGTAGCTGAGACTATATGTGCTGCTACCATGCACAGCTGATTTTTAAATTTTTTTG
TAGAGATGGAGTTGCCCAGGCTGGTCTTGAACTCCTGGCCTGAGGTGATCCTCCTGCGTTGACCTCCCAAGTATCT
TAGACTACAGATGCACTCCACCACGCTTG

SEQ. ID. No. 10
ZABC1 Open reading frame
ATGCAATCGAAAGTGACAGGAAACATGCCAACTCAATCCCTCTTAATGTACATGGATGGGCCAGAAGTGATTGGCA
GCTCTCTTGGCAGTCCGATGGAGATGGAGGATGCCTTGTCAATGAAAGGGACCGCTGTTGTTCCATTCCGAGCTAC
ACAAGAAAAAATGTCATCCAAATCGAGGGGTATATGCCCTTGGATTGCATGTTCTGCAGCCAGACCTTCACACAT
TCAGAAGACCTTAATAAACATGTCTTAATGCAACACCGGCCTACCCTCTGTGAACCAGCAGTTCTTCGGGTTGAAG
CAGAGTATCTCAGTCCGCTTGATAAAAGTCAAGTGCGAACAGACCTTCCAAGGAAAAGAATTGCAAGGAAAATGA
ATTTAGCTGTGAGGTATGTGGGCAGACATTTAGAGTCGCTTTTGATGTTGAGATCCACATGAGAACACACAAAGAT
TCTTTCACTTACGGGTGTAACATGTGCGGAAGAAGMTTSRRSSAGCCTTGGTTTCTTAAAAATCACATGCGGACAC
ATAATGGCAAATCGGGGGCCAGAAGCAAACTGCAGCAAGGCTTGGAGAGTAGTCCAGCAACGATCAACGAGGTCGT
CCAGGTGCACGCGGCCGAGAGCATCTCCTCTCCTTACAAAATCTGCATGGTTTGTGGCTTCCTATTTCCAAATAAA
GAAAGTGCTAATTGAGCACCGCAAGGTGCACACCAAAAAAACTGCTTTCGGTACCAGCAGCGCGCAGACAGACTCTC
CACAAGGAGGAATGCCGTCCTCGAGGGAGGACTTCCTGCAGTTGTTCAACTTGAGACCAAAATCTCACCCTGAAAC
GGGGAAGAAGCCTGTCAGATGCATCCCTCAGCTCGATCCGTTCACCACCTTCCAGGCTTGGCAGCTGGCTACCAAA
GGAAAAGTTGCCATTTGCCAAGAAGTGAAGGAATCGGGGCAAGAAGGGGCACCGACAACGACGATTCGAGTTCCG
AGAAGGAGCTTGGAGAAACAAATAAGGGCAGTTGTGCAGGCCTCTCGCAAGAGAAAGAGAAGTGCAAACACTCCCA
CGGCGAAGCGCCCTCCGTGGACGCGGATCCCAAGTTACCCAGTAGCAAGGAGAAGCCCACTCACTGCTCCGAGTGC
GGCAAAGCTTTCAGAACCTACCACCAGCTGGTCTTGCACTCCAGGGTCCACAAGAAGGACCGGAGGGCCGGCGCGG
AGTCGCCCACCATGTCTGTGGACGGGAGGCAGCCGGGACGGTGTTCTCCGACCTCGCCGCCCCTCTGGATGAAAA
TGGAGCCGTGGATCGAGGGGAAGGTGGTTCTGAAGACGGATCTGAGGATGGGCTTCCCGAAGGAATCCATCTGGAT
AAAAATGATGATGGAGGAAAAATAAAACATCTTACATCTTCAAGAGAGTGTAGTTATTGTGGAAAGTTTTTCCGTT
CAAATTATTACCTCAATATTCATCTCAGAACGCATACAGGTGAAAAACCATACAAATGTGAATTTTGTGAATATGC
TGCAGCCCAGAAGACATCTCTGAGGTATCACTTGGAGAGACATCACAAGGAAAAACAAACCGATGTTGCTGCTGAA
GTCAAGAACGATGGTAAAAATCAGGACACTGAAGATGCACTATTAACCGCTGACAGTGCGCAAACCAAAAATTTGA
AAAGATTTTTTGATGGTGCCAAAGATGTTACAGGCAGTCCACCTGCAAAGCAGCTTAAGGAGATGCCTTCTGTTTT
TCAGAATGTTCTGGGCAGCGCTGTCCTCTCACCAGCACACAAAGATACTCAGGATTTCCATAAAAATGCAGCTGAT
GACAGTGCTGATAAAGTGAATAAAAACCCTACCCCTGCTTACCTGGACCTGTTAAAAAAGAGATCAGCAGTTGAAA
CTCAGGCAAATAACCTCATCTGTAGAACCAAGGCGGATGTTACTCCTCCTCCGGATGGCAGTACCACCCATAACCT
TGAAGTTAGCCCCAAAGAGAAGCAAACGGAGACCGCAGCTGACTGCAGATACAGGCCAAGTGTGGATTGTCACGAA
AAACCTTTAAATTTATCCGTGGGGGCTCTTCACAATTGCCCGGCAATTTCTTTGAGTAAAAGTTTGATTCCAAGTA
TCACCTGTCCATTTTGTACCTTCAAGACATTTTATCCAGAAGTTTTAATGATGCACCAGAGACTGGAGCATAAATA
CAATCCTGACGTTCATAAAAACTGTCGAAACAAGTCCTTGCTTAGAAGTCGACGTACCGGATGCCCGCCAGCGTTG
CTGGGAAAAGATGTGCCTCCCCTCTCAGTTTCTGTAAACCCAAGCCCAAGTCTGCTTTCCCGGCGCAGTCCAAAT
CCCTGCCATCTGCGAAGGGGAAGCAGAGCCCTCCTGGGCCAGGCAAGGCCCCTCTGACTTCAGGGATAGACTCTAG
CACTTTAGCCCCAAGTAACCTGAAGTCCCACAGACCACAGCAGAATGTGGGGGTCCAAGGGGCCGCCACCAGGCAA

```
CAGCAATCTGAGATGTTTCCTAAAACCAGTGTTTCCCCTGCACCGGATAAGACAAAAAGACCCGAGACAAAATTGA
AACCTCTTCCAGTAGCTCCTTCTCAGCCCACCCTCGGCAGCAGTAACATCAATGGTTCCATCGACTACCCCGCCAA
GAACGACAGCCCGTGGGCACCTCCGGGAGAGACTATTTCTGTAATCGGAGTGCCAGCAATACTGCAGCAGAATTT
GGTGAGCCCCTTCCAAAAAGACTGAAGTCCAGCGTGGTTGCCCTTGACGTTGACCAGCCCGGGGCCAATTACAGAA
GAGGCTATGACCTTCCCAAGTACCATATGGTCAGAGGCATCACATCACTGTTACCGCAGGACTGTGTGTATCCGTC
GCAGGCGCTGCCTCCCAAACCAAGGTTCCTGAGCTCCAGCGAGGTCGATTCTCCAAATGTGCTGACTGTTCAGAAG
CCCTATGGTGGCTCCGGGCCACTTTACACTTGTGTGCCTGCTGGTAGTCCAGCATCCAGCTCGACGTTAGAAGGTC
TTGGTGGATGTCAGTGCTTACTCCCCATGAAATTAAATTTTACTTCATCCTTTGAGAAGCGAATGGTGAAAGCTAC
TGAAATAAGCTGTGATTGTACTGTACATAAAACATATGAGGAATCTGCAAGGAACACTACAGTTGTGTAA

SEQ. ID. No. 11
ZABC1 Protein
MQSKVTGNMPTQSLLMYMDGPEVIGSSLGSPMEMEDALSMKGTAVVPFRATQEKNVIQIEGYMPLDCMFCSQTFTH
SEDLNKHYLMQHRPTLCEPAVLRVEAEYLSPLDKSQVRTEPPKEKNCKENEFSCEVCGQTFRVAFDVEIHMRTHKD
SFTYGCNMCGRXXXXPWFLKNHMRTHNGKSGARSKLQQGLESSPATINEVVQVHAAESISSPYKICMVCGFLFPNK
ESLIEHRKVETKKTAFGTSSAQTDSPQGGMPSSREDFLQLFNLRPKSHPETGKKPVRCIPQLDPFTTFQAWQLATK
GKVAICQEVKESGQEGSTDNDDSSEKELGETNKGSCAGLSQEKEKCKHSHGEAPSVDADPKLPSSKEKPTHCSEC
GKAFRTYHQLVLHSRVHKKDRRAGAESPTMSVDGRQPGTCSPDLAAPLDENGAVDRGEGGSEDGSEDGLPEGIHLD
KNDDGGKIKHLTSSRECSYCGKFFRSNYYLNIHLRTHTGEKPYKCEFCEYAAAQKTSLRYHLERHHKEKQTDVAAE
VKNDGKNQDTEDALLTADSAQTKNLKRFFDGAKDVTGSPPAKQLKEMPSVFQNVLGSAVLSPAHKDTQDFHKNAAD
DSADKVNKNPTPAYLDLLKKRSAVETQANNLICRTKADVTPPPDGSTTHNLEVSPKEKQTETAADCRYRPSVDCHE
KPLNLSVGALHNCPAISLSKSLIPSITCPFCTFKTFYPEVLMMHQRLEHKYNPDVHKNCRNKSLLRSRRTGCPPAL
LGKDVPPLSSFCKPKPKSAFPAQSKSLPSAKGKQSPPGPGKAPLTSGIDSSTLAPSNLKSHRPQQNVGVQGAATRQ
QQSEMPPKTSVSPAPDKTKRPETKLKPLPVAPSQPTLGSSNINGSIDYPAHKNDSPWAPPGRDYFCNRSASNTAAEF
GEPLPKRLKSSVVALDVDQPGANYRRGYDLPKYHMVRGITSLLPQDCVYPSQALPPKPRFLSSSEVDSPNVLTVQK
PYGGSGPLYTCYPAGSPASSSTLEGLGGCQCLLPMKLNFTSSFEKRMVKATEISCDCTVHKTYEESARNTTYV SEQ. ID. NO. 12
1b1
GGAAACAGCTATGACCATGATTACGCCAAGCTCGAAATTAACCCTCACTAAAGGGAACAAAAGCTGGAGCTCCACC
GCGGTGGCGGCCGCTCTAGAACTAGTGGATCCCCCGGGCTGCAGGAATTCGGCACGAGGCTCCACCGACAGCCAGG
CACTGGGCAGCACGCACTGGAGACCCAGGACCCTGTGCAGGAGCAGCTCCGGGTGACACGAGGGGACTGAAGATAC
TCCCACAGGGGCTCAGCAGGAGCAATGGGTAACCAAATGAGTGTTCCCCAAAGAGTTGAAGACCAAGAGAATGAAC
CAGAAGCAGAGACTTACCAGGACAACGCGTCTGCTCTGAACGGGGTTCCAGTGGTGGTGTCGACCCACACAGTTCA
GCACTTAGAGGAAGTCGACTTGGGAATAAGTGTCAAGACGGATAATGTGGCCACTTCTTCCCCCGAGACAACGGAG
ATAAGTGCTGTTGCGGATGCCAACGGAAAGAATCTTGGGAAGAGGCCAAACCCGAGGCACCAGCTGCTAAATCTC
GTTTTTTCTTGATGCTCTCTCGGCCTGTACCAGGACGTACCGGAGACCAAGCCGCAGATTCATCCCTTGGATCAGT
GAAGCTTGATGTCAGCTCCAATAAAGCTCCAGCGAACAAAGACCCAAGTGAGAGCTGGACACTTCCGGTGGCAGCT
GGACCGGGGCAGGACACAGATAAAACCCCAGGGCACGCCCCGGCCCAAGACAAGGTCCTCTCTGCCGCCAGGGATC
CCACGCTTCTCCCACCTGAGACAGGGGGAGCAGGAGGGAGAAGCTCCCTCCAAGCCCAAGGACTCCAGCTTTTTGA
CAAATTCTTCAAGCTGGACAAGGGACAGGAAAAGGTGCCAGGTGACAGCCAACAGGAAGCCAAGAGGGCAGAGCAT
CAAGACAAGGTGGATGAGGTTCCTGGCTTATCAGGGCAGTCCGATGATGTCCCTGCAGGGAAGGACATAGTTGACG
GCAAGGAAAAAGAAGGACAAGAACTTGGAACTGCGGATTGCTCTGTCCCTGGGGACCCAGAAGGACTGGAGACTGC
AAAGGACGATTCCCAGGCAGCAGCTATAGCAGAGAATAATAATTCCATCATGAGTTTCTTTAAAACTCTGGTTTCA
CCTAACAAAGCTGAAACAAAAAAGGACCCAGAAGACACAGGGTGCTGAAAAGTCACCCACCACTTCAGCTGACCTTA
AGTCAGACAAAGCCAACTTTACATCCCAGGAGACCCAAGGGGCTGGCAAGAATTCCCAAAGGATGCAACCCATCGGG
GCACACACAGTCCGTGACAACCCCTGAACCTGCAAGGAAGGCACCAAGGAGAAATCAGGACCCACCTCTCTGCCT
CTGGGCAAACTGTTTTGGAAAAAGTCAGTTAAAGAGGACTCAGTCCCCACAGGTGCGGAGGAGAATGTGGTGTGTG
AGTCACCAGTAGAGATTATAAAGTCCAAGGAAGTAGAATCAGCCTTACAAACAGTGGACCTCAACGAAGGAGATGC
TGCACCTGAACCCACAGAAGCGAAACTCAAAAGAGAAGAAAGCAAACCAAGAACCTCTCTGATGGCGTTTCTCAGA
CAAATGTCAGTGAAAGGGGATGGAGGGATCACCCACTCAGAAGAAATAAATGGGAAAGACTCCAGCTGCCAAACAT
CAGACTCCACAGAAAAGACTATCACACCGCCAGAGCCTGAACCAACAGGAGCACCACAGAAGGGTAAAGAGGGCTC
CTCGAAGGACAAGAAGTCAGCAGCCGATGATGAACAAGCAGAAGAGCCAGACGCCAAAGAACCAGCCCAG
TGCACAGAGCAGGCCACGGTGGACACGAACTCACTGCAGAATGGGGACAAGCTCCAAAAGAGACCTGAGAAGCGGC
AGCAGTCCCTTGGGGGCTTCTTTAAAGGCCTGGGACCAAAGCGGATGTTGGATGCTCAAGTGCAAACAGACCCAGT
ATCCATCGGACCAGTTGGCAAACCCAAGTAAACAAATCAGCACGGTTCCCACCAGGTTCTCCTGCCACCAAGATGT
GTTCTCCTTACTCCATCTCCTCCCCAAACACGTCCATGTATATATTCTTCTGACCAGCAAATGAAATTCTGC
CTAGAAATTAAGCCCGAGCTGTTGTATATTGAGGTGTATTATTTACGTCTCTGGTCCAGTCTTTTCTGGCAAATAA
CAGTAAAGATGGTTTAGCAGGTCACCTAGTTGGGTCAGAAGAGTCGATGATCACCAAGCAGGAAAGGGAGGGAATA
GAGGAATGTGTTCGGGTTAAGTGATGAAAATGGCAGTGGTGGCCGGGCGTGGTGGCTCTCGCCTGTAATCTCAGCA
CTTTGGGAGGCCGAGGCAGGTGGATCACCTGAGGTCAGGAGTTCAAGACCAGCCTGGCCAACATCATGAAACCCCG
TCTCTACTAAAAATACAAAAATTAGCCAGGCATGGTGGCACACACCTGTAGTCCCAGCTACTCGGGAGCCCAACGC
ACGAGAACCGCTTGTACCCAGGAGGTGGAGGTTGCAGTGAGCCGAAGTTGCACCATTGCACTCCACCCTGGGCGAC
AGAGCAAGATTCTATCAAAAAAAAAAGGCAGTGGCAAGTAAGTTATAGAAGAGAAATGCTGCTAGAAGGAATTAAG
CGTTGTAGTAAACGCGTGCTCATCCTCTAAGCTTGAAGAAGGGAGACGAAAATCCATTTGTTTAAATTCACATCTC
AAGGAGGGAGAACCCGGGCTGTGTTGGGTGGTTGCCAATTTCCTAGAACGGAATGTGTGGGGTATAGAAAAAGGAA
TGAATAAGCGTTGTTTTTCAAATAGGGTCCTTGTAAGTTATTGATGAGAGGGAAAAGATTGACTGGGGAGGGCTTA
AAATGATTTGGGAAAACAATTGCTTTTGAGGCTCAGTGACAACGGCAAAGATTACAACTTAAAAAAAAAAAAAAAA
AAACTCGAGACTAGTTCTCTCTCTCTCGTGCCGAATTCGATATCAAGCTTATCGATACCGTCGACCTCGAGGGG
GGGCCCGGTACCCAATTCGCCCTATA SEQ. ID. NO. 13
Genomic Sequence from BAC clone 97
Filtered query sequence:
>query_seq
TGTGATATTGATTCATGCCCTCTTGCACCTTGCCAAACATCACACGCTTG
CCATCCAGTCCACTCGATTTTGGCAGTGCAGATGAAAAACTGGGAACCAT
```

SEQUENCE LISTING

```
TTGTGTTGAGTCCAGCAAGATGCCAGGACCTGCATGTTTCAGAACGAAGT
TCTTCATCATCCAATTTCTCCCTGTATATGGGCTTACCACNACTGCCGTT
AAGTCGTGTNAAGTCACCACTCAGGTACATAATGGAATAATTCTGCAAAG
GCAGGAGNCACTTTCTCTCCAGTGCTCAGACCATGAAAGTTTTCTGATGT
CTTTGGAACTTTGTCTGCAAATAGCTCGAAGGAGACATGGCCTAAAGGCT
CGCCATCTGCGGTGATATTGNAACATGGTAGGGCTGACCGTGGCTGTGGC
CATGACTTTTTAGANTNNNNNNNNNNNNNNNNNNNNNNNNNNNNNNNNNN
NNNNNNNNNNNNNNNNNNNNNNNNNNNNNNNNNNNNNNNNNNNNNNNNNN
NNNNNNNNNNNNNNNCCCAATGCGGGACAGAGAATCNAAGAAACTGTATTA
GGGAAAGGGTCCTGAGTTTATGCCAAAGTTTCCCAGATTGGTTTCCATTG
AAACGTAGCTCTGTGAGATACCATCAGGTGTTATGTGAAGAAATGTCTGT
GTAGTCAAATATGTTTGAGTGAGTGAGCCTGAGCTGAGCAAGACTTTACT
GCAAGACTTCCCATCTTCTGTCCCTTTTTATGCTAATGGGTAACACAAAC
TCCAAAAGTGGGGTGTACAGCATGAGGCATTAACAAAAATTTATTGGACC
CCACACACNNNNNNNNNNNNNNNNNNNNNNNNNNNNNNNNNNNNNNNNNN
NNNNNNNNNNNNNNNNNNNNNNNNNNNNNNNNNNNNNNNNNNNNNNNNNN
NNNNNNNNNNNNNNNNNNNNNNNNNNNNNNNNNNNCTCTC

SEQ ID NO 14
gb|M19533|RATCYCA Rat cyclophilin mRNA, complete cds.
Length = 743
Minus Strand HSPs:

Score = 418 (115.5 bits), Expect = 1.5e-58, Sum P(5) = 1.5e-58
Identities = 96/112 (85%), Positives = 96/112 (85%), Strand = Minus/Plus
S = rat CYCLOPHILLIN; q= SEQ ID NO 13.

Query:  372 TNCAATATCACCGCAGATGGCGAGCCTTTAGGCCATGTCTCCTTCGAGCTATTTGCAGAC   313
                |   ||||| || |||||||||| || ||   |||  |||||||| ||||||||||
Sbjct:   64 TTCGACATCACGGCTGATGGCGAGCCCTTGGGTCGCGTCTGCTTCGAGCTGTTTGCAGAC   123

Query:  312 AAAGTTCCAAAGACATCAGAAAACTTTCATGGTCTGAGCACTGGAGAGAAAG   261
                ||||||||||||||| |||||||||||| || |||||||||||| ||||||
Sbjct:  124 AAAGTTCCAAAGACAGCAGAAAACTTTCGTGCTCTGAGCACTGGGGAGAAAG   175

Score = 236 (65.2 bits), Expect = 1.5e-58, Sum P (5) = 1.5e-58
Identities = 52/58 (89%), Positives = 52/58 (89%), Strand = Minus/Plus Query:  117 TGCTGGACTCAACACAAATGGTTCCCAGTTTTTCATCTGCACTGCCAAAATCGAGTGG   60
                ||||||||  |||||||||||||||||||||| ||||||||||||| |  |||||
Sbjct:  348 TGCTGGACCAAACACAAATGGTTCCCAGTTTTTTATCTGCACTGCCAAGACTGAGTGG   405

Score = 177 (48.9 bits), Expect = 1.5e-58, Sim P(5) = 1.5e-58
Identities = 41/48 (85%), Positives = 41/48 (85%), Strand = Minus/Plus Query:   60 GACTGGATGGCAAGCGTGTGATGTTTGGCAAGGTGCAAGAGGGCATGA   13
                |  |||||||||||||| |||| | ||||| |||||| ||||  |||||||
Sbjct:  404 GGCTGGATGGCAAGCATGTGGTCTTTGGGAAGGTGAAAGAAGGCATGA   451

Score = 154 (42.6 bits), Expect = 1.5e-58, Sum P(5) = 1.5e-58
Identities = 34/38 (89%), Positives = 34/38 (89%), Strand = Minus/Plus Query:  153 AGAACTTCGTTCTGAAACATGCAGGTCCTGGCATCTTG   116
                |||||||| | ||||| ||| |||||||||||||||||
Sbjct:  299 AGAACTTCATCCTGAAGCATACAGGTCCTGGCATCTTG   336

Score = 86 (23.8 bits), Expect = 1.5e-58, Sum P(5) = 1.5e-58
Identities = 22/28 (78%), Positives = 22/28 (78%), Strand = Minus/Plus Query:  256 TCCTGCCTTTGCAGAATTATTCCATTAT   229
                ||||  |  ||  ||||||||||||||  ||
Sbjct:  193 TCCTCCTTTCACAGAATTATTCCAGGAT   220
```

The invention claimed is:

1. A method of assaying for a prognostic indicator of breast cancer, the method comprising determining overexpression of the ZABC1 gene in a biological sample suspected of containing cancer cells, wherein overexpression of the ZABC1 gene, relative to normal tissue, indicates a poor prognosis, and wherein the method comprises determining ZABC1 protein level using an immunoassay that utilizes an antibody that specifically binds ZABC1.

2. The method of claim 1 wherein the biological sample is a human biological sample, and the ZABC1 gene encodes SEQ ID NO:11.

3. The method of claim 1, wherein the immunoassay comprises a radioimmunoassay.

4. The method of claim 3, wherein the biological sample is a human biological sample, and the ZABC1 protein comprises SEQ ID NO:11.

5. The method of claim 1, wherein the biological sample is a sample obtained from breast.

6. The method of claim 1, where the biological sample comprises a solid tumor.

7. The method of claim 1, where the biological sample comprises a clinical sample selected from the group consisting of an aspiration, a tissue section, and a needle biopsy.

8. The method of claim 1, wherein the immunoassay comprises an enzyme-linked immunosorbent assay.

9. The method of claim 1, wherein the immunoassay comprises an immunofluorescent assay.

* * * * *